United States Patent [19]

Kamiya et al.

[11] 4,203,897

[45] May 20, 1980

[54] PENAM DERIVATIVES

[75] Inventors: Takashi Kamiya, Suita; Tsutomu Teraji; Masashi Hashimoto, both of Toyonaka; Osamu Nakaguti, Nagaicho-higashi; Teruo Oku, Kyoto, all of Japan

[73] Assignee: Fujisawa Pharmaceutical Company, Limited, Osaka, Japan

[21] Appl. No.: 32,293

[22] Filed: Apr. 23, 1979

Related U.S. Application Data

[62] Division of Ser. No. 867,623, Jan. 6, 1978, which is a division of Ser. No. 648,491, Jan. 12, 1976, Pat. No. 4,084,049, which is a division of Ser. No. 407,962, Oct. 19, 1973, Pat. No. 3,954,732.

[30] Foreign Application Priority Data

| Nov. 8, 1972 | [JP] | Japan | 47-112348 |
| Dec. 12, 1972 | [JP] | Japan | 47-1201 |
| Dec. 12, 1972 | [JP] | Japan | 47-128657 |
| Dec. 20, 1972 | [JP] | Japan | 47-128659 |
| Dec. 22, 1972 | [JP] | Japan | 47-2270 |
| Aug. 1, 1973 | [JP] | Japan | 48-87108 |

[51] Int. Cl.² ............................. C07D 499/44
[52] U.S. Cl. ..................... 260/239.1; 424/271; 260/239 A; 424/246; 544/16
[58] Field of Search ............................. 260/239.1

[56] References Cited

U.S. PATENT DOCUMENTS

| 3,578,660 | 5/1971 | Cooper | 544/16 |
| 3,660,396 | 5/1972 | Wright | 260/243 C |
| 3,708,480 | 1/1973 | Webber et al. | 544/16 |
| 3,719,672 | 2/1973 | Heussler et al. | 260/243 C |
| 3,780,028 | 12/1973 | Naito et al. | 260/243 C |
| 3,792,995 | 2/1974 | Ochiai et al. | 260/243 C |
| 3,799,938 | 3/1974 | Heussler et al. | 544/16 |
| 3,814,754 | 6/1974 | Jackson | 260/243 C |
| 3,883,517 | 5/1975 | Heussler et al. | 544/16 |
| 3,923,795 | 12/1975 | Spry | 260/243 C |
| 3,926,972 | 12/1975 | Lowe | 260/243 C |

*Primary Examiner*—Nicholas S. Rizzo
*Attorney, Agent, or Firm*—Oblon, Fisher, Spivak, McClelland & Maier

[57] ABSTRACT

A compound of the general formula:

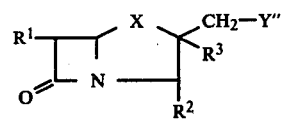

wherein $R^1$ is amino or a conventional, pharmaceutically acceptable acylamino, $R^2$ is carboxy or a conventionally protected carboxy, X is —S— or

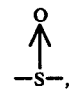

$R^3$ is lower alkyl and Y″ is a residue of a strong nucleophile selected from the group consisting of azido, thiocyanato, lower alkyanoylthio and piperidinothiocarbonylthio.

4 Claims, No Drawings

PENAM DERIVATIVES

This is a division, of application Ser. No. 867,623, filed Jan. 6, 1978, which is a Divisional of Ser. No. 648,491 filed Jan. 12, 1976, now U.S. Pat. No. 4,084,049 which is a Divisional of Ser. No. 407,962, filed Oct. 19, 1973, now U.S. Pat. No. 3,954,732.

This invention relates to antibacterially active Penam and Cepham derivatives and processes for the preparation thereof.

The processes included in this invention are shown in the following scheme:

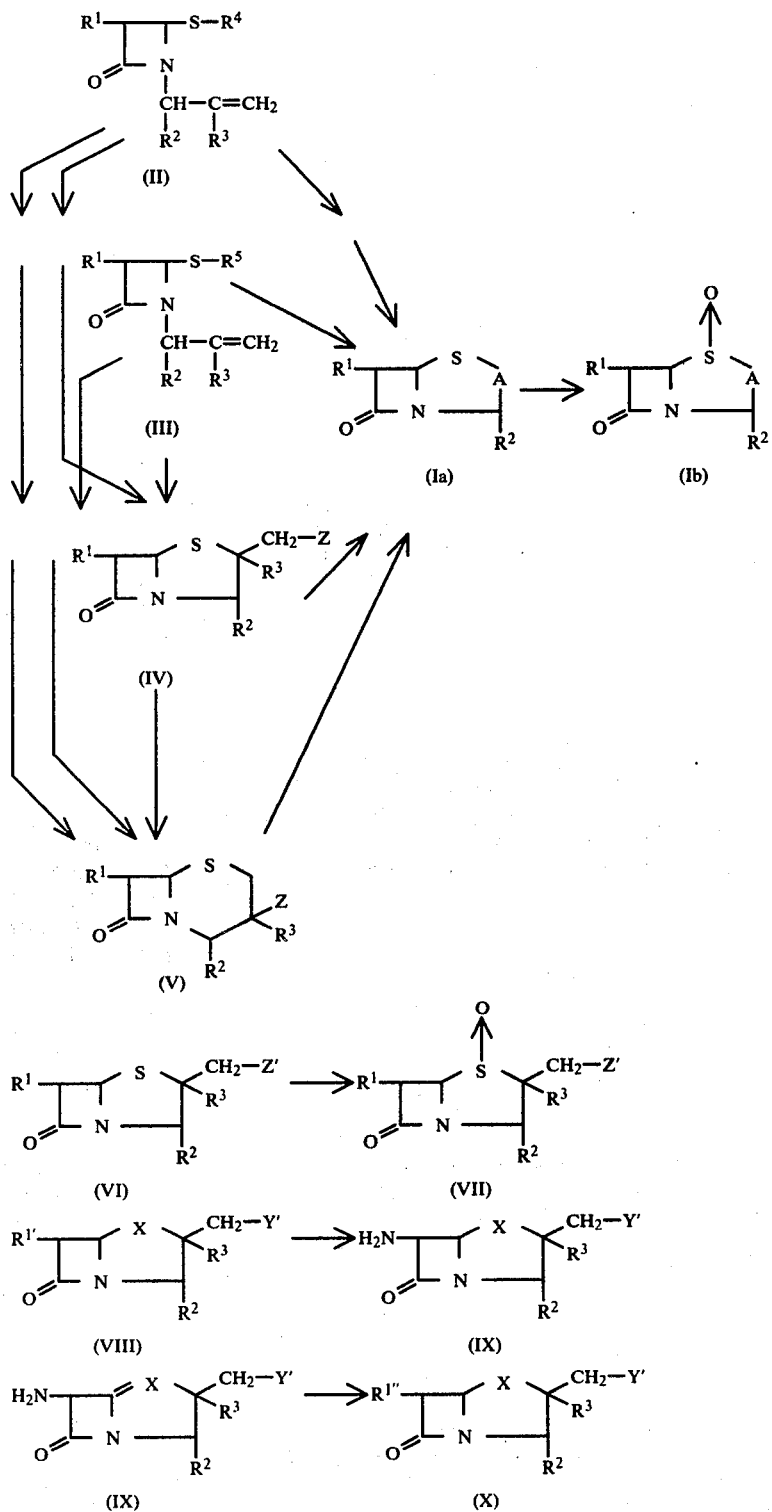

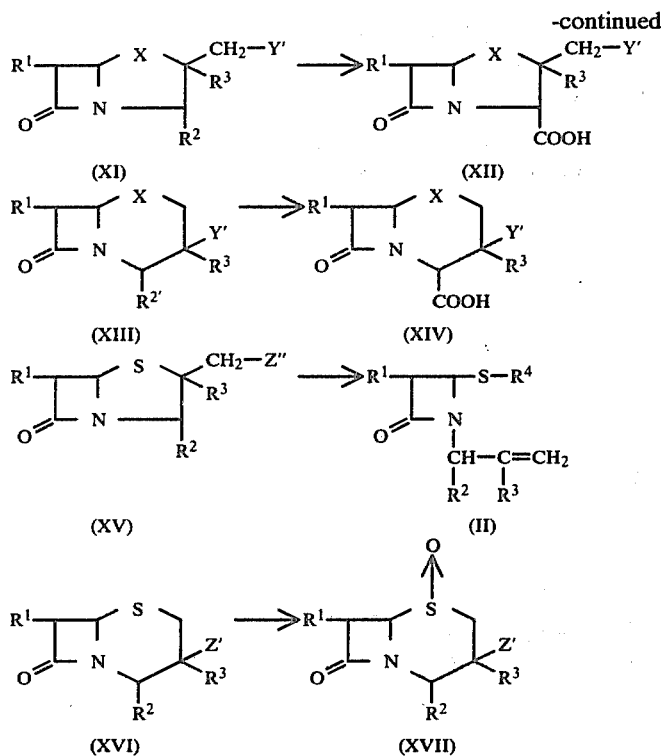

Wherein $R^1$ is amino or a substituted amino, $R^2$ is carboxy or a conventionally protected carboxy, $R^3$ is lower alkyl, $R^4$ is a residue of a thiol compound $HR^4$, $R^5$ is amino or a residue of an amine, X is —S— or

Y is a residue of a nucleophile, Z is a group convertible into a residue of a nucleophile, $R^{1'}$ is a protected amino, $R^{1''}$ is acylamino, $R^{2'}$ is a protected carboxy, Y' is halogen or a residue of a nucleophile, Z' is halogen, Z'' is a residue of an acid and A is a group of the formula:

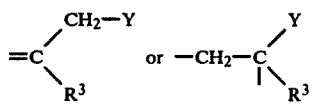

in which $R^3$ and Y are each as defined above.

The compounds (II) to be used as the starting compounds in the processes of this invention may be prepared by reacting the corresponding 2-methyl-2-lower alkyl-6-substituted-penam-3-carboxylic acid-1-oxide compound with the corresponding thiol compound, and the compounds (III) to be used as the starting compounds may be prepared by reacting the corresponding compounds (II) with ammonia or the corresponding amine.

In the above and subsequent description, the term "a substituted amino" for $R^1$ means suitable conventional, pharmatically acceptable substituted amino groups which include;

suitable substituted amino groups include hydrazino, mono(or di)-(lower)alkylamino, mono)or di)-(lower)alkenylamino, lower alkylideneamino, ar(lower)alkylideneamino, acylamino and amino group substituted with other amino protecting groups than the acyl groups;

suitable lower alkyl groups in the mono(or di)-lower alkylamino include methyl, ethyl, propyl, isopropyl, butyl, etc.;

suitable lower alkenyl groups in the mono(or di)-(lower)-alkenylamino include allyl, 2-butenyl, etc.;

suitable lower alkylidene groups in the lower alkylideneamino include ethylidene, propylidene, butylidene, etc.;

suitable ar(lower)alkylidene groups in the ar(lower)-alkylidene include benzylidene, phenethylidene, etc.;

suitable acyl groups in the acylamino groups include carbamoyl, aliphatic acyl groups and acyl groups containing an aromatic or heterocyclic ring;

suitable aliphatic acyl groups include saturated or unsaturated, lower or higher alkanoyl groups which may be branched or which may contain a cyclic ring, such as lower or higher aliphatic acyl groups, for example, lower alkanoyl (e.g., formyl, acetyl, propionyl, butyryl, isobutyryl, valeryl, isovaleryl, oxalyl, succinyl, pivaloyl, etc.), higher alkanoyl (e.g., octanoyl, lauroyl, palmitoyl, etc.), lower alkenoyl (e.g., acryloyl, crotonoyl, etc.), lower alkynoyl (e.g., propynoyl, etc.), lower or higher cycloalkanecarbonyl (e.g., cyclopentanecarbonyl, cyclohexanecarbonyl, cycloheptanecarbonyl, etc.), lower or higher cycloalkyl(lower)alkanoyl(e.g., cyclopentylacetyl, cyclohexylacetyl, cycloheptylacetyl, cyclohexylpropionyl, cycloheptylpropionyl, etc.), lower or higher cycloalkadiene carbonyl(e.g., dihydrobenzoyl, etc.), lower or higher cycloalkadienyl (lower-)alkanoyl(e.g., dihydrophenylacetyl, dihydrophenylpropionyl, etc.), etc., and lower or higher aliphatic acyl groups containing a oxygen or sulfur atom, for example, lower alkoxy(lower)alkanoyl (e.g., methoxyacetyl, ethoxyacetyl, methoxypropionyl, etc.), lower alkylthio(lower)alkanoyl(e.g., methylthioacetyl, ethylthioacetyl, methylthiopropionyl, etc.), lower alkenylthio(lower)alkanoyl(e.g., allylthioacetyl, allylthiopropionyl, etc.), lower or higher cycloalkylthio(lower)alkanoyl(e.g., cyclopentylthioacetyl, cyclohexylthiopropionyl, cycloheptylthioacetyl, etc.), lower or higher cycloalkoxy(lower)alkanoyl(e.g., cyclopentyloxyacetyl, cyclohexyloxypropionyl, etc.), lower or higher cycloalkanedienyloxy(lower) alkanoyl(e.g., dihydrophenoxyacetyl, dihydrophenoxypropionyl, etc.), lower or higher cycloalkanedienylthio(lower)alkanoyl(e.g., dihydrophenylthioacetyl, dihydrophenylthiopropionyl, etc.), lower alkoxycarbonyl(e.g., methoxycarbonyl, ethoxycarbonyl, propoxycarbonyl, 1-cyclopropylethoxycarbonyl, isopropoxycarbonyl, butoxycarbonyl, tertiarybutoxycarbonyl, etc.), lower or higher cycloalkyloxycarbonyl (e.g., cyclopentyloxycarbonyl, cyclohexyloxycarbonyl, cycloheptyloxycarbonyl, etc.), lower or higher cycloalkanedienyloxycarbonyl (e.g., dihydrophenoxycarbonyl, etc.);

suitable acyl groups containing an aromatic ring such as benzene, naphthalene and the like, include, for example, arylcarbamoyl (e.g., phenylcarbamoyl, etc.), aryloyl (e.g., benzoyl, toluoyl, naphthoyl, α-methylnaphthoyl, phthaloyl, benzenesulfonyl, tetrahydronaphthoyl, indancarbonyl, etc.), ar(lower)alkanoyl (e.g., phenylacetyl, phenylpropionyl, phenylbutyryl, tolylacetyl, xylylacetyl, naphtylacetyl, tetrahydronaphthylacetyl, indanylacetyl, etc.) and the carbon atom in the alkylmoiety of said ar(lower)alkanoyl group may be replaced with an oxygen or sulfur atom or carbonyl group, for example, aryloxy(lower)alkanoyl(e.g., phenoxyacetyl, phenoxypropionyl, phenoxybutyryl, xylyloxyacetyl, etc.), aryloxycarbonyl (e.g., phenoxycarbonyl, xylyloxycarbonyl, naphthyloxycarbonyl, indanyloxycarbonyl, etc.) ar(lower)alkoxycarbonyl (e.g., benzyloxycarbonyl, phenethyloxycarbonyl, etc.), arylthio(lower) alkanoyl(e.g., phenylthioacetyl, phenylthiopropionyl, etc.), arylglyoxyloyl(e.g., phenylglyoxyloyl, etc.), etc.;

suitable acyl groups containing an heterocyclic ring include, for example, heterocyclic carbonyl or heterocyclic lower alkanoyl; the heterocyclic in the heterocyclic carbonyl or heterocyclic lower alkanoyl; may be saturated or unsaturated, monocyclic or polycyclic, and may contain at least one hetero-atom, such as an oxygen, sulfur, nitrogen atom or the like, for example, unsaturated 3 to 8-membered heteromonocyclic containing a sulphur atom(e.g., thienyl, etc.), unsaturated condensedheterocyclic containing a sulfur atom (e.g., benzothienyl, etc.), unsaturated 3 to 8-membered heteromonocyclic containing an oxygen atom(e.g., furyl, 2(or 4)pyranyl, 5,6-dihydro-2H-pyran-3-yl, etc.), unsaturated 3 to 8-membered heteromonocyclic containing 1 to 4 nitrogen atom(s) (e.g., pyrrolyl, 2(or 3)H-pyrrolyl, 2(or 3)-pyrrolinyl, imidazolyl, pyrazolyl, pyridyl, pyrimidyl, pyrazinyl, pyridazinyl, 1H-tetrazolyl, 2H-tetrazolyl, etc.), saturated 3 to 8-membered heteromonocyclic containing 1 to 2 nitrogen atom(s) (e.g., pyrrolidinyl, imidazolidinyl, piperidino, piperadinyl, etc.), unsaturated condensed-heterocyclic containing 1 to 3 nitrogen atom(s) (e.g., indolyl, isoindoyl, indolizinyl, benzimidazolyl, quinolyl, isoquinolyl, 1(or 2)H-indazolyl, 1(or 2) H-benzotriazolyl, etc.), unsaturated 3 to 8-membered heteromonocyclic containing an oxygen atom(s) and 1 to 3 nitrogen atom(s) (e.g., oxazolyl, isoxazolyl, oxadiazolyl, etc.), saturated 3 to 8 membered heteromonocyclic containing 1 to 2 oxygen atom(s) and 1 to 2 nitrogen atom(s) (e.g., sydnonyl, etc.), unsaturated 3 to 8-membered heteromonocyclic containing a sulfur atom and 1 to 3 nitrogen atom(s) (e.g., thiazolyl, thiadiazolyl, etc.), unsaturated condensed-heterocyclic containing an oxygen atom and 1 to 2 nitrogen atom(s) (e.g., benzoxazolyl, benzoxadiazolyl, etc.), unsaturated condensed-heterocyclic containing a sulfur atom and 1 to 2 nitrogen atom(s) (e.g., benzothiazolyl, benzothiadiazolyl, etc.), etc.; the carbon atom in the lower alkyl moiety in said heterocyclic lower alkanoyl may be replaced with an oxygen or sulfur atom such as heterocyclic lower alkoxycarbonyl, heterocyclic-oxycarbonyl, heterocyclic-oxy(lower)alkanoyl and heterocyclic-thio(lower)alkanoyl;

the carbamoyl, the aliphatic acyl groups and the acyl groups containing an aromatic or heterocyclic ring may have 1 to 10 appropriate substituent(s) such as lower alkyl(e.g., methyl, ethyl, propyl, isopropyl, etc.), lower alkenyl (e.g., 1-propenyl, allyl, etc.), lower or higher cycloalkyl (e.g., cyclopropyl, cyclopentyl, cyclohexyl, cycloheptyl, etc.), lower alkoxy (e.g., methoxy, ethoxy, propoxy, isopropoxy, etc.), lower alkylthio(e.g., methylthio, ethylthio, etc.), aryl(e.g., phenyl, xylyl, tolyl, indanyl, etc.), ar(lower)alkyl(e.g., benzyl, phenethyl, etc.), halogen (e.g., chlorine, bromine, fluorine, etc.), halophenyl(e.g., chlorophenyl, bromophenyl, etc.), halophenoxy(e.g., chlorophenoxy, bromophenoxy, etc.), cyano, lower alkylsulfinyl(e.g., methylsulfinyl, ethylsulfinyl, etc.), lower alkanesulfonyl(e.g., methanesulfonyl, ethanesulfonyl, etc.), lower alkoxycarbonyl(lower)alkoxy (e.g., methoxycarbonylmethoxy, ethoxycarbonylethoxy, 1-cyclopropylethoxycarbonylmethoxy, tertiarybutoxycarbonylmethoxy, etc.), nitro, sulfo, amino, azido, mercapto, carboxy, hydroxy, hydroxyamino, mono(or di) alkylamino (e.g., mino(or di)methylamino, mono(or di)ethylamino, mono(or di)propylamino, mono(or di) isopropylamino, etc.;

when the acyl group has a functional group, such as amino, hydroxy, mercapto, carboxy, etc., the functional group may be protected with an appropriate protective group; suitable protective group for the amino group include any of the conventional protective groups, for example, the acyl groups or other groups than the acyl groups such as trityl, 2-nitrophenylthio, 2,4-dinitrophenylthio, 2-hydroxybenzylidene, 2-hydroxy-5-chlorobenzylidene, 2-hydroxy-1-naphthylmethylene, 3-hydroxy-4-pyridylmethylene, 1-methoxycarbonyl-2-propylidene, 1-ethoxycarbonyl-2-propylidene, 3-ethoxycarbonyl-2-butylidene, 1-acetyl-2-propylidene, 1-benzoyl-2-propylidene, 1-[N-(2-methoxyphenyl)carbamoyl]-2-propylidene, 1-[N-(4-methoxyphenyl) carbamoyl]-2-propylidene, 2-ethoxycarbonylcyclohexylidene, 2-ethoxycarbonylcyclopentylidene, 2-acetylcyclohexylidene, 3,3-dimethyl-5-oxocyclohexylidene (among these, 1-methoxycarbonyl-2-propylidene and 2-ethoxycarbonylcyclohexylidene radicals may be representable as 1-methoxycarbonyl-1-propene-2-yl and 2-ethoxycarbonyl-1-cyclohexenyl radical, respectively), mono or disilyl, etc.;

suitable protective groups for hydroxy or mercapto groups include any of the conventional protective groups for hydroxy or mercapto groups, for example, the acyl groups or other groups than the acyl group such as benzyl, trityl, methoxymethyl, 2-nitrophenylthio, 2,4-dinitrophenylthio, etc.;

suitable protective groups for the carboxy group may be any of those conventional protective groups used for protecting a carboxy group, for example, lower alkyl ester (e.g., methyl ester, ethyl ester, propyl ester, butyl ester, 1-cyclopropylethyl ester, tertiarybutyl ester, etc.), mino(or di or tri)halo(lower)alkyl ester (e.g., chloromethyl ester, 2,2,2-trichloroethyl ester, 3,3-dibromopropyl ester, etc.), aryl ester (e.g., phenyl ester, nitrophenyl ester, indanyl ester, etc.), ar(lower)alkyl ester (e.g., benzyl ester, diphenylmethyl ester, triphenylmethyl ester, p-nitrobenzyl ester, p-bromobenzyl ester, etc.), tri(lower)alkylsilyl ester (e.g., trimethylsilyl ester, triethylsilyl ester, etc.) etc.;

the amino protective group other than an acyl group which is mentioned in the substituted amino group is the same as that which is exemplified as the protective group for the amino radical in the acyl group; particularly suitable acyl groups include:

(1) lower alkoxycarbonyl(e.g., methoxycarbonyl, ethoxycarbonyl, propoxycarbonyl, 1-cyclopropylethoxycarbonyl, butoxycarbonyl, tetiarybutoxycarbonyl, etc.), (2) lower alkylthio(lower)alkanoyl (e.g., 2-methylthioacetyl, 2-methylthioacetyl, 2-ethylthioacetyl, 3-methylthiopropionyl, etc.), (3) lower alkenylthio(lower)alkanoyl (e.g., 2-allylthioacetyl, 3-allylthiopropionyl, etc.)

(4) cyano(lower)alkanoyl (e.g., 2-cyanoacetyl, 3-cyanopropionyl, 4-cyanobutyryl, etc.), (5) phenyl(lower)alkanoyl (e.g., 2-phenylacetyl, 3-phenylpropionyl, 4-phenylbutyryl, etc.), (6) phenoxy(lower)alkanoyl (e.g., 2-phenoxyacetyl, 3-phenoxypropionyl, 4-phenoxybutyryl, etc.), (7) phenylcarbamoyl, (8) phenylglyoxyloyl, (9) phenylthiocarbonyl,

(10) phenyl and amino substituted lower alkanoyl (e.g., phenylglycyl, 3-amino-3-phenylpropionyl, etc.),

(11) phenyl and hydroxy substituted lower alkanoyl (e.g., 2-hydroxy-2-phenylacetyl, 2-hydroxy-3-phenylpropionyl, etc.),

(12) phenyl and lower alkoxycarbonylamino substituted lower alkanoyl (e.g., N-methoxycarbonylphenylglycyl, N-ethoxycarbonylphenylglycyl, N-(1-cyclopropylethoxy)-carbonyl-phenylglycyl, N-tertiarybutoxycarbonylphenylglycyl, 2-(1-cyclopropylethoxy)carbonylamino-3-phenylpropionyl, etc.),

(13) phenyl and trihalo(lower)alkoxycarbonylamino substituted lower alkanoyl (e.g., N-trichloroethoxycarbonylphenylglycyl, 3-trichloroethoxycarbonylamino-3-phenylpropionyl, N-tribromoethoxycarbonylphenylglycyl, etc.),

(14) phenyl and lower alkanoyloxy substituted lower alkanoyl (e.g., 2-formyloxy-2-phenylacetyl, 2-acetoxy-2-phenylacetyl, 3-propionyloxy-3-phenylpropionyl, etc.),

(15) phenyl and semicarbazono substituted lower alkanoyl (e.g., 2-phenyl-2-semicarbazonoacetyl, 2-semicarbazono-3-phenylpropionyl, etc.),

(16) halophenylthiocarbamoyl (e.g., 2-(or 3 or 4-) chlorophenylthiocarbamoyl, 2-(or 3- or 4-)chlorophenylthiocarbamoyl, 2-(or 3- or 4-) bromophenylthiocarbamoyl, etc.),

(17) phthaloyl,

(18) lower alkanoylaminobenzenesulfonyl (e.g., 2-(or 3- or 4-(acetamidobenzenesulfonyl, 2-(or 3- or 4-(propionamidobenzenesulfonyl, etc.),

(19) phenyl and halophenoxy substituted lower alkanoyl (e.g., 2-phenyl-2-[2-(or 3- or 4-(chlorophenoxy]acetyl, 2-phenyl-2-[2-(or 3-or 4-)bromophenoxy]acetyl, etc.),

(20) halophenyl(lower)alkanoyl (e.g., 2-[2-(or 3- or 4-)chlorophenyl] acetyl, 2-[2-(or 3- or 4-)bromophenyl]acetyl, 3-[2-(or 3- or 4-)chlorophenyl]propionyl, etc.),

(21) phenyl(lower)alkoxycarbonyl (e.g., benzyloxycarbonyl, phenethyloxycarbonyl, etc.),

(22) hydroxphenyl and amino substituted lower alkanoyl (e.g., 2-amino-2-[2-(or 3- or 4-)hydroxyphenyl]acetyl, 2-amino-3-[2-(or 3- or 4-) hydroxyphenyl]propionyl, etc.),

(23) hydroxyphenyl and lower alkoxycarbonylamino substituted lower alkanoyl (e.g., 2-methoxycarbonylamino-2-[2-(or 3- or 4-)hydroxy-phenyl]acetyl, 2-(1-cyclopropylethoxy)carbonylamino-2-[2-(or 3- or 4-) hydroxyphenyl]acetyl, 2-tertiarybutoxycarbonylamino-2-[2-(or 3-or 4-)hydroxyphenyl]acetyl, etc.),

(24) phenyl and sulfo substituted lower alkanoyl (e.g., 2-phenyl-2-sulfoacetyl, 3-phenyl-3-sulfopropionyl, etc.),

(25) lower alkoxyphenyl and amino substituted lower alkanoyl (e.g., 2-amino-2-[2-(or 3- or 4-)methoxyphenyl]acetyl, 2-amino-3-[2-(or 3-or 4-)methoxyphenyl]acetyl, etc.),

(26) lower alkoxyphenyl and lower alkoxycarbonylamino substituted lower alkanoyl (e.g., 2-methoxycarbonylamino-2-[2-(or 3- or 4-)methoxyphenyl]acetyl, 2-(1-cyclopropylethoxy)carbonylamino-2-[2-(or 3- or 4-)-methoxyphenyl]acetyl, 2-tertiarybutoxycarbonylamino-2-[2-(or 3- or 4-) methoxyphenyl]acetyl, etc.),

(27) lower alkylthiophenyl and amino substituted lower alkanoyl (e.g., 2-amino-2-[2-(or 3- or 4-)methylthiophenyl]acetyl, 2-amino-3-[2-(or 3- or 4-)ethylthiophenyl]-propionyl, etc.),

(28) lower alkylthiophenyl and lower alkoxycarbonylamino substituted lower alkanoyl (e.g., 2-methoxycarbonylamino-2-[2-(or 3- or 4-)methylthiophenyl]acetyl, 2-(1-cyclopropylethoxy)carbonylamino-2-[2-(or 3- or 4-)methylthiophenyl]-acetyl, 2-tertiarybutoxycarbonylamino-2-[2-(or 3- or 4-)methylthiophenyl]acetyl, 2-tertiarybutoxycarbonylamino-3-[2-(or 3- or 4-)ethylthiophenyl]propionyl, etc.),

(29) lower alkylsulfinylphenyl and amino substituted lower alkanoyl (e.g., 2-amino-2-[2-(or 3- or 4-)methylsulfinylphenyl]acetyl, 2-amino-3-[2-(or 3- or 4-(ethylsulfinylphenyl]propionyl, etc.),

(30) lower alkylsulfinylphenyl and lower alkoxycarbonylamino substituted lower alkanoyl (e.g., 2-methoxycarbonylamino-2-[2-(or 3- or 4-(methylsulfinylphenyl]acetyl, 2-(1-cyclopropylethoxy)carbonylamino-3-[2-(or 3- or 4-)ethylsulfinylphenyl]propionyl, 2-tertiarybutoxycarbonylamino-2-[2-(or 3- or 4-)methylsulfinylphenyl]acetyl, etc.),

(31) lower alkoxycarbonyl(lower)alkoxyphenyl and amino substituted lower alkanoyl (e.g., 2-amino-2-[2-(or 3- or 4-)methoxycarbonylmethoxyphenyl]acetyl, 2-amino-3-[2-(or 3- or 4-)propoxycarbonylmethoxyphenyl]propionyl, 2-amino-2-[2-(or 3- or 4-)tertiarybutoxycarbonylmethoxyphenyl]acetyl, etc.),

(32) lower alkoxycarbonyl(lower)alkoxyphenyl and lower alkoxycarbonylamino substituted lower alkanoyl (e.g., 2-methoxycarbonylamino-2-[2-(or 3- or 4-)methoxycarbonylmethoxyphenyl]acetyl, 2-(1-cycloropylethoxy)carbonyl 3-[2-(or 3- or 4-)ethoxycarbonylmethoxyphenyl] propionyl, 2-tertiarybutoxycarbonylamino-2-[2-(or 3- or 4-)tertiarybutoxycarbonylmethoxyphenyl]acetyl, etc.),

(33) phenyl and thiadiazolylthio(lower)alkanoylamino substituted lower alkanoyl (e.g., N-(1,3,4-thiadiazol-2-yl)thioacetylphenylglycyl, 2-[3-(1,3,4-thiadiazol-2-yl)thiopropionyl]amino-3-phenylpropionyl, etc.),

(34) phenyl and indanyloxycarbonyl substituted lower alkanoyl(e.g., 2-phenyl-2-indanyloxycarbonylacetyl, 3-phenyl-2-indanyloxycarbonylpropionyl, etc.),

(35) dihydrophenyl and amino substituted lower alkanoyl (e.g., 2-amino-2-(2,5-dihydrophenyl)acetyl, 2-amino-3-(2,5-dihydrophenyl) propionyl, etc.),

(36) dihydrophenyl and lower alkoxycarbonylamino substituted lower alkanoyl (e.g., 2-methoxycarbonylamino-2-(2,5-dihydrophenyl)acetyl, 2-(1-cyclopropylethoxy)-carbonylamino-2-(2,5-dihydrophenyl)acetyl, 2-tertiarybutoxycarbonylamino-2-(2,5-dihydrophenyl)-acetyl, 2-tertiarybutoxycarbonylamino-3-(2,5-dihydrophenyl)propionyl, etc.),

(37) 3-halophenyl-5-lower alkylisoxazol-4-ylcarbonyl (e.g., 3-[2-(or 3- or 4-)chlorophenyl]-5-methylisoxazol-4-ylcarbonyl, 3-[2-(or 3- or 4-)bromophenyl]-5-ethylisoxazol-4-ylcarbonyl, etc.),

(38) thienyl(lower)alkanoyl(e.g., 2-(2-thienyl)acetyl, 3-(2-thienyl) propionyl, etc.),

(39) thinyl and amino substituted lower alkanoyl (e.g., 2-amino-2-(2-thienyl)acetyl, 2-amino-3-(2-thienyl)propionyl, etc.),

(40) thienyl and lower alkoxycarbonylamino substituted lower alkanoyl (e.g., 2-metoxycarbonylamino-2-(2-thienyl)acetyl, 2-(1-cyclopropylethoxy)carbonylamino-2-(2-thienyl)acetyl, 2-tertiarybutoxycarbonylamino-2-(2-thienyl)acetyl, 2-tertiarybutoxycarbonylamino-3-(2-thienyl)propionyl, etc.),

(41) tetrazolyl)lower)alkanoyl (e.g., 2-(1H-tetrazol-1-yl)acetyl, 3-(1H-tetrazol-1-yl)propionyl, 4-(1H-tetrazol-1-yl)butyryl, etc.),

(42) thiadiazolyl(lower)alkanoyl, (e.g., 2-(1,2,5-thiadiazol-3-yl) acetyl, 2-(1,3,4-thiadiazol-2-yl)acetyl, 3-(1,2,5-thiadiazol-3-yl) propionyl, etc.),

(43) thiadiazolylthio(lower)alkanoyl (e.g., 2-(1,3,4-thiadiazol-2-ylthio)acetyl, 2-(1,2,5-thiadiazol-3-ylthio)acetyl, 3-(1,3,4-thiadiazol-2-ylthio)propionyl, etc.),

(44) halobenzotriazolyl(lower)alkanoyl (e.g., 2-[4-(or 5- or 6- or 7-)chloro-1H-benzotriazol-1-yl]acetyl, 2-[4-(or 5- or 6- or 7-)bromo-1H-benzotriazol-1-yl]-acetyl, 3-[4-(or 5- or 6- or 7-)fluoro-2H-benzotriazol-2-yl]propionyl, etc.),

(45) lower alkylthiadiazolyloxy(lower)alkanoyl (e.g., 2-(5-methyl-1,3,4-thiadiazol-2-yloxy)acetyl, 2-(4-methyl-1,2,5-thiadiazol-3-yloxy)acetyl, 2-(5-ethyl-1,3,4-thiadiazol-2-yloxy)propionyl, etc.),

(46) dihydropyranyl and amino substituted lower alkanoyl (e.g., 2-amino-2-(5,6-dihydro-2H-pyran-3-yl)acetyl, 2-amino-3-(5,6-dihydro-2H-pyran-3-yl)propionyl, etc.),

(47) dihydropyranyl and lower alkoxycarbonylamino substituted lower alkanoyl (e.g., 2-methoxycarbonylamino-2-(5,6-dihydro-2H-pyran-3-yl)acetyl, 2-(1-cyclopropylethoxy)carbonylamino-2-(5,6-dihydro-2H-pyran-3-yl)acetyl, 2-tertiarybutoxycarbonylamino-2-(5,6-dihydro-2H-pyran-3-yl)acetyl, 2-tertiarybutoxycarbonylamino-3-(5,6-dihydro-2H-pyran-3-yl)propionyl, etc.), and

(48) sydnonyl(lower)alkanoyl (e.g., 2-(sydnon-3-yl)acetyl, 3-(sydnon-3-yl)propionyl, etc.):

the term "a protected amino" for $R^{1'}$ includes acylamino and amino group substituted with other amino protecting groups than the acyl groups as illustrated above:

the term "acylamino" for $R^{1''}$ includes acylamino as illustrated above:

the term "a protected carboxy group" for $R^2$ and $R^{2'}$ includes ester, acid amide, acid anhydride, salt, etc.;

suitable esters include silyl esters, aliphatic esters and esters containing an aromatic or heterocyclic ring;

suitable silyl esters such as tri(lower)alkylsilyl(e.g., trimethylsilyl, triethylsilyl, etc.) esters, etc.;

suitable aliphatic esters include saturated or unsaturated, lower or higher alkyl esters which may be branched or which may contain a cyclic ring, such as lower or higher aliphatic esters, for example, lower alkyl (e.g., methyl, ethyl, propyl, isopropyl, 1-cyclopropylethyl, butyl, tertiarybutyl, etc.) esters, higher alkyl (e.g., octyl, nonyl, undecyl, etc.) esters, lower alkenyl (e.g., vinyl, 1-propenyl, allyl, 3-butenyl, etc.) esters, lower alkynyl (e.g., 3-butynyl, 4-pentynyl, etc.) esters, lower or higher cycloalkyl (e.g., cyclopentyl, cyclohexyl, cycloheptyl, etc.) esters, etc., and lower or higher aliphatic esters containing a nitrogen, sulfur or oxygen atom, for example, lower alkoxy(lower)alkyl (e.g., methoxymethyl, ethoxyethyl, methoxyethyl, etc.) esters, lower alkylthio (lower)alkyl (e.g., methylthiomethyl, ethylthioethyl, methylthiopropyl, etc.) esters, di(lower)alkylamino (e.g., dimethylamino, diethylamino, dipropylamino, etc.) esters, lower alkylidenamino (e.g., ethylideneamino, propylideneamino, isopropylideneamino, etc.) esters, lower alkylsulfenyl(lower)alkyl(e.g., methylsulfenylmethyl, ethylsulfenylmethyl, etc.) esters, etc.;

suitable esters containing an aromatic ring include, for example, aryl (e.g., phenyl, xylyl, tolyl, naphthyl, indanyl, dihydroanthryl, etc.) esters, ar(lower)alkyl (e.g., benzyl, phenethyl, etc.) esters aryloxy(lower)-alkyl (e.g., phenoxymethyl, phenoxyethyl, phenoxypropyl, etc.)esters, arylthio(lower)alkyl(e.g., phenylthiomethyl, phenylthioethyl, phenylthiopropyl, etc.)esters, arylsulfenyl(lower)alkyl(e.g., phenylsulfenylmethyl, phenylsulfenylethyl, etc.), aryloyl(lower)alkyl(e.g., benzoylmethyl, toluoylethyl, etc.), aryloylamino(e.g., phthalimido, etc.)esters, etc.;

suitable esters containing an heterocyclic ring include, for example, heterocyclic esters, heterocyclic lower alkyl esters, etc.;

suitable heterocyclic esters include, for example, saturated or unsaturated, condensed or uncondensed 3 to 8-membered heterocyclic containing 1 to 4 hetero-atom(s) such as an oxygen, sulfur and nitrogen atom (e.g., pyridyl, pyperidino, 2-pyridon-1-yl, tetrahydropyranyl, quinolyl, pyrazolyl, etc.)esters, etc.;

suitable heterocyclic lower alkyl esters include, for example, saturated or unsaturated, condensed or uncondensed 3 to 8-membered heterocyclic containing 1 to 4 hetero-atom(s) such as an oxygen, sulfur and nitrogen atom(e.g., pyridyl, pyperidino, 2-pyridon-1-yl, tetrahydropyranyl, quinolyl, pyrazolyl, etc.)substituted lower alkyl (e.g., methyl, ethyl, propyl, etc.)esters, etc.;

the silyl esters, the aliphatic esters and the esters containing an aromatic or heterocyclic ring may have 1 to 10 appropriate substituent(s) such as lower alkyl(e.g., methyl, ethyl, propyl, isopropyl, butyl, tertiarybutyl, etc.), lower alkoxy(e.g., methoxy, ethoxy, propoxy, isopropoxy, butoxy, tertiarybutoxy, etc.), lower alkylthio(e.g., methylthio, ethylthio, propylthio, etc.), lower alkylsulfinyl(e.g., methylsulfinyl, ethylsulfinyl, propylsulfinyl, etc.), lower alkanesulfonyl(e.g., methanesulfonyl, ethanesulfonyl, etc.), phenylazo, halogen(e.g., chlorine, bromine, fluorine, etc.), cyano, nitro, etc., for example mono(or di or tri)halo(lower)alkyl(e.g., chloromethyl, bromoethyl, dichloromethyl, 2,2,2-trichloroethyl, 2,2,2-tribromoethyl, etc.)esters, cyano(lower)alkyl(e.g., cyanomethyl, cyanoethyl, etc.)esters, mono(or di or tri or tetra or penta)halophenyl(e.g., 4-chlorophenyl, 3,5-dibromophenyl, 2,4,5-trichlorophenyl, 2,4,6-trichlorophenyl, pentachlorophenyl, etc.)esters, lower alkanesulfonylphenyl(e.g., 4-methanesulfonylphenyl, 2-ethanesulfonylphenyl, etc.)esters, 2-(or 3- or 4-)phenylazophenyl esters, mono(or di or tri)nitrophenyl-(e.g., 4-nitrophenyl, 2,4-dinitrophenyl, 3,4,5-trinitrophenyl, etc.)esters, mono(or di or tri or tetra or penta)halophenyl(lower)alkyl(e.g., 2-chlorobenzyl, 2,4-dibromobenzyl, 3,4,5-trichlorobenzyl, pentachlorobenzyl, etc.)esters, mono(or di or tri)nitrophenyl(lower)alkyl-(e.g., 2-nitrobenzyl, 2,4-dinitrobenzyl, 3,4,5-trinitrobenzyl, etc.)esters, mono(or di or tri)(lower)alkoxyphenyl(lower)alkyl(e.g., 2-methoxybenzyl, 3,4-dimethoxybenzyl, 3,4,5-trimethoxybenzyl, etc.)esters, hydroxy and di(lower)alkylphenyl(lower)alkyl(e.g., 3,5-dimethyl-4-hydroxybenzyl, 3,5-ditertiarybutyl-4-hydroxybenzyl, etc.)esters, etc.;

suitable acid amides include, for example, N-lower alkyl acid amide(e.g., N-methyl acid amide, N-ethyl acid amide, etc.), N,N-di(lower)alkyl acid amide(e.g., N,N-dimethyl acid amide, N,N-diethyl acid amide, N-methyl-N-ethyl acid amide, etc.), N-phenyl acid amide, or an acid amide with pyrazole, imidazole, 4-lower alkylimidazole(e.g., 4-methylimidazole, 4-ethylimidazole, etc.), etc.;

suitable acid anhydrides include, for example, an acid anhydride with a di(lower)alkyl phosphate(e.g., dimethyl phosphate, diethyl phosphate, etc.), dibenzylphosphate, phosphoric acid halide(e.g, phosphoric acid chloride, phosphoric acid bromide, etc.), di(lower)alkyl phosphite(e.g., dimethyl phosphite, diethyl phosphite, etc.), sulfurous acid, thiosulfuric acid, sulfuric acid, lower alkyl carbonate(e.g., methyl carbonate, ethyl carbonate, etc.), hydrazoic acid, hydrohalogenic acid-(e.g., hydrochloric acid, hydrobromic acid, etc.), saturated or unsaturated lower aliphatic carboxylic acid-(e.g., pivalic acid, pentanoic acid, isopentanoic acid, 2-ethylbutanoic acid, crotonic acid, valeric acid, propionic acid, etc.), saturated or unsaturated halo(lower)aliphatic carboxylic acid(e.g., chloroacetic acid, 3-chloro-2-pentenoic acid, 3-bromo-2-butenoic acid, etc.), substituted lower aliphatic carboxylic acid(e.g., phenylacetic acid, phenoxyacetic acid, furanacetic acid, thiopheneacetic acid, etc.), aromatic carboxylic acid(e.g., benzoic acid, etc.), or a symmetric acid anhydride, etc.; and suitable acid salts include an acid salt with a metal(e.g., sodium potassium, magnesium, etc.) or an organic amine(e.g., methylamine, diethylamine, trimethylamine, aniline, pyridine, picoline, N,N'-dibenzylethylenediamine, etc.), etc.;

the term "lower alkyl" for $R^3$ means the one having straight, branched or cyclic 1 to 6 carbon chain such as methyl, ethyl, propyl, isopropyl, butyl, tert-butyl, cyclohexyl, etc.:

the "term" a residue of a thiol compound $HR^4$ for $R^4$ means a residue given by omitting the hydrogen atom from a thiol compound $HR^4$;

suitable residues of thiol compounds include a substituted or unsubstituted, aliphatic thiol, aromatic thiol, or heterocyclic thiol compound;

suitable aliphatic thio groups include, for example, lower alkylthio(e.g., methylthio, ethylthio, propylthio, isopropylthio, butylthio, isobutylthio, etc.), lower alkenylthio(e.g., vinylthio, 1-isopropenylthio, 3-butenylthio, etc.), etc.;

suitable substituted aliphatic thio groups include, for example, lower alkoxy(lower)alkylthio(e.g., methoxymethylthio, ethoxymethylthio, etc.), ar(lower)alkylthio(e.g., benzylthio, phenethylthio, xylylmethylthio, etc.), halophenyl(lower)alkylthio(e.g., 4-chlorobenzylthio, 4-bromobenzylthio, etc.), nitrophenyl(lower)alkylthio(e.g., 4-nitrobenzylthio, etc.), mono(or di)-lower alkoxyphenyl(lower)alkylthio(e.g., 4-methoxybenzylthio, 2,4-dimethoxybenzylthio, etc.), halogen and lower alkoxy substituted phenyl(lower)alkylthio(e.g., 2-chloro-4-methoxybenzylthio, etc.), etc.;

suitable aromatic thio groups include arylthio(e.g., phenylthio, xylylthio, tolylthio, naphthylthio, etc.), suitable substituted aromatic thio groups include, for example, mono(or di)halophenylthio(e.g., chlorophenylthio, bromophenylthio, dichlorophenylthio, etc.), nitrophenylthio, mono(or di)-lower alkoxyphenylthio(e.g., methoxyphenylthio, dimethoxyphenylthio, etc.), halogen and nitro substituted phenylthio(e.g., chloronitrophenylthio, etc.), etc.;

suitable heterocyclic groups in the heterocyclic thio groups may contain at least one hetero-atom such as an oxygen, nitrogen, sulfur atom and the like.;

suitable heterocyclic groups include, for example, unsaturated 3 to 8-membered heteromonocyclic containing a sulfur atom(e.g., thienyl, etc.), unsaturated 3 to 8-membered heteromonocyclic containing an oxygen atom (e.g., furyl, etc.), unsaturated 3 to 8-membered heteromonocyclic containing 1 to 4 nitrogen atom(s) (e.g., pyrrolyl, pyridyl, imidazolyl, triazolyl, tetrazolyl, etc.), saturated 3 to 8-membered heteromonocyclic containing 1 to 2 nitrogen atom(s)(e.g., pyrrolidinyl, peperazinyl, piperizinyl, homopiperizinyl, etc.), unsaturated condensed-heterocyclic containing 1 to 3 nitrogen atom(s)(e.g., quinolyl, isoquinolyl, benzimidazolyl, etc.), unsaturated 3 to 8-membered heteromonocyclic containing an oxygen atom and 1 to 3 nitrogen atom(s)-(e.g., oxazolyl, oxadiazolyl, oxatriazol, etc.), unsaturated 3 to 8-membered heteromonocyclic containing a sulfur and 1 to 3 nitrogen atom(s)(e.g., thiazolyl, thiadiazolyl, thiatriazoly, etc.), unsaturated condensed heterocyclic containing an oxygen and nitrogen atom-(e.g., benzoxazolyl, etc.), unsaturated condensed-heterocyclic containing a sulfur and nitrogen atom(e.g., benzothiazolyl, etc.), and suitable substituted heterocyclic groups in the substituted heterocyclic thio groups include, for example, the above mentioned heterocyclic groups are substituted with 1 to 6 appropriate substituent(s) such as lower alkyl radical(e.g., methyl, ethyl, etc.), a lower alkoxy radical(e.g., methoxy, ethoxy, etc.), a halogen atom(e.g., fluorine, chlorine, bromine, etc.), a nitro radical, an aryl radical(e.g., phenyl, tolyl, xylyl, etc.), a substituted aryl radical(e.g., chlorophenyl, nitrophenyl, etc.), an ar(lower)alkyl radical-(e.g., benzyl, phenethyl, etc.) or the like:

the term "a residue of an amine" for $R^5$ includes a residue of primary amine(e.g., a residue of primary aliphatic amine, a residue of primary aromatic amines, etc.) or a residue of secondary amine(e.g., a residue of secondary aliphatic amine, a residue of secondary aromatic amine, a residue of secondary cyclic amine, etc.);

suitable residues of primary aliphatic amine include, for example, lower alkylamino(e.g., methylamino, ethylamino, propylamino, isopropylamino, butylamino, etc.), lower or higher cycloalkylamino (e.g., cyclopentylamino, cyclohexylamino, etc.), etc.;

suitable residue of primary aromatic amine includes, for example, arylamino(e.g., anilino, etc.), ar(lower)alkylamino(e.g., benzylamino, phenethylamino, etc.), etc.;

suitable residue of secondary aliphatic amine includes, for example, di(lower)alkylamino(e.g., dimethylamino, methylethylamino, diethylamino, dipropylamino, dibutylamino, etc.), etc.;

suitable residue of secondary aromatic amine includes, for example, diarylamino(e.g., diphenylamino, etc.), bisar(lower)alkylamino(e.g., dibenzylamino, diphenethylamino, etc.), etc.; and suitable residue of secondary cyclic amine includes, for example, pyrrolidinyl, piperidino, morpholino, 4-methylpiperazinyl, etc.), etc.:

the term "a nucleophile" in the term "a residue of a nucleophile" for Y and Y' includes thiocyanic acid, thiocyanogen, hydrazoic acid, thiourea, aliphatic or aromatic or heterocyclic thiourea, thiosemicarbazide, aliphatic or aromatic or heterocyclic thiomide, aliphatic or aromatic or heterocyclic thiol, aliphatic or aromatic or heterocyclic carboxylic acid, aliphatic or aromatic or heterocyclic thiocarboxylic acid, dithiocarbonic acid ester, aliphatic or aromatic or heterocyclic dithiocarbamic acid, aliphatic or aromatic or heterocyclic amine, aminobenzoic acid, aminobenzenesulfonic acid, cyanic acid, phthalimide, succinimide, aliphatic or aromatic or heterocyclic alcohol, pyrrole, substituted pyrrole, imidazole, triazole, tetrazole or a salt thereof;

suitable aliphatic thioureas include, for example, mono- (or di or tri)lower alkylthiourea(e.g., N-methylthiourea, N,N,N'-triethylthiourea, etc.), mono(or di or di)lower or higher cycloalkylthiourea(e.g., dicyclohexylthiourea, etc.), etc.;

suitable aromatic thioureas include, for example, diarylthiourea(e.g., diphenylthiourea, etc.), lower alkyl and aryl substituted thiourea(e.g., N,N-dimethyl-N'-phenylthiourea, etc.), diar(lower)alkylthiourea(e.g., N,N'-dibenzylthiourea, etc.), lower alkyl and ar(lower)alkyl substituted thiourea(e.g., N-ethyl-N'-benzylthiourea, etc.), etc.;

suitable heterocyclic thioureas include, for example, diheterocyclic thiourea(e.g., N,N-difuryl, thiourea, etc.), lower alkyl and heterocylic substituted thiourea(e.g., N-propyl-N'-pyridylthiourea, etc.), etc.;

suitable aliphatic thioamides include, for example, thio(-lower)alkaneamide(e.g., thioacetamide, thiopropionamide, etc.), etc.;

suitable aromatic thioamides include, for example, thiobenzamide, thioar(lower)alkaneamide(e.g., thiophenylacetamide, etc.), etc.;

suitable heterocyclic thioamides include, for example, thiopyridinecarboxamide, etc.;

suitable aliphatic thiols include, for example, lower alkanethiol(e.g., methanethiol, ethanethiol, propanethiol, isobutanethiol, etc.), amino(lower)alkanethiol-(e.g., aminoethanethiol, etc.), di(lower)alkylamino(-lower)alkanethiol(e.g., dimethylaminopropanethiol, etc.), etc.;

suitable aromatic thiols include, for example, thiophenol, aminothiophenol, dinitrothiophenol, phenyl(-lower)alkanethiol(e.g., phenylmethanethiol, etc.), etc.;

suitable heterocyclic thiols may contain at least one hetero-atom such as an oxygen, nitrogen, sulfur atom and the like in the ring; suitable heterocyclic thiols include, for example, unsaturated 3 to 8-membered heterocyclic thiol containing 1 to 4 nitrogen atom(s) in the ring(e.g., pyrrolethiol, pyrazolethiol, imidazolethiol, lower alkylimidazolethiol such as methylimidazolethiol or dihydroimidazolethiol, pyridinethiol, lower alkylpyridinethiol such as methylpyridinethiol, or tetrazolethiol, lower alkyltetrazolethiol such as methyltetrazolethiol, etc., unsaturated condensed-heterocyclic thiol containing 1 to 3 nitrogen atom(s) in the ring(e.g., indolethiol, etc.), unsaturated 3 to 8-membered heteromonocyclic thiol containing a sulfur atom in the ring(e.g., thiophenethiol, etc.), unsaturated condensed-heterocyclicthiol containing 1 to 3 sulfur atom(s) in the ring(e.g., thianthrenethiol, etc.), unsaturated 3 to 8-membered heterocyclic thiol containing a sulfur atom and 1 to 2 nitrogen atom(s) in the ring(e.g., thiazolethiol, dihydrothiazolethiol, thiadiazolethiol, lower alkylthiadiazolethiol such as methylthiadiazolethiol, or lower alkylthiothiadiazolethiol such as ethylthiothiadiazolethiol, or aminothiadiazolethiol, etc.), unsaturated condensed-heterocyclic thiol containing a sulfur atom and 1 to 2 nitrogen atom(s) in the ring(e.g., benzothiazolethiol, etc.), unsaturated 3 to 8-membered heteromonocyclic thiol containing an oxygen atom in the ring(furanthiol, etc.), unsaturated condensed-heterocyclic thiol containing an oxygen atom and 1 to 2 nitrogen atom(s) in the ring(e.g., benzoxazolethiol, etc.), unsaturated 3 to 8-membered heteromonocyclic thiol containing an oxygen atom and 1 to 2 nitrogen atom(s) in the ring(e.g., oxadiazolethiol, lower alkyloxadiazolethiol such as propyloxadiazolethiol, etc.), etc.;

suitable aliphatic carboxylic acid includes, for example, lower aliphatic carboxylic acid(e.g., acetic acid, propionic acid, etc.); suitable aromatic carboxylic acid includes, for example, benzoic acid, etc.;

suitable heterocyclic acid includes, for example, nicotinoic acid, etc.;

suitable aliphatic thiocarboxylic acids include, for example, thio(lower)alkanoic acid(e.g., thioacetic acid, etc.), etc.;

suitable aromatic thiocarboxylic acids includes, for example, thiobenzoic acid, etc.;

suitable heterocyclic thiocarboxylic acids include, for example, thiopyridinecarboxylic acid, etc.;

suitable dithiocarbonic acid esters include, for example, lower alkyl dithiocarbonate(e.g., methyl dithiocarbonate, ethyl dithiocarbonate, etc.), ar(lower)alkyl dithiocarbonate(e.g., benzyl dithiocarbonate, etc.), etc.;

suitable aliphatic dithiocarbamic acids, include, for example, N-(lower)alkyldithiocarbamic acid(e.g., N-methyldithiocarbamic acid, etc.), N,N-di(lower)alkyldithiocarbamic acid(e.g., N,N-dimethyldithiocarbamic acid, etc.), etc.;

suitable aromatic dithiocarbamic acids include, for example, N-phenyldithiocarbamic acid, etc.;

suitable heterocyclic dithiocarbamic acids include, for example, peperidinodithiocarbamic acid, 4-lower(alkyl)-1-piperazinyldithiocarbamic acid(e.g., 4-methyl-1-piperazinyldithiocarbamic acid, etc.), etc.;

suitable aliphatic amines include, for example, mono(or di)-lower alkylamine(e.g., methylamine, diethylamine, etc.), etc.;

suitable aromatic amines include, for example, aniline, toluidine, nitroaniline, nitrotoluidine, naphthylamine, etc.;

suitable heterocyclic amines include, for example, pyrrolylamine, etc.;

suitable aliphatic alcohols include, for example, lower alkanol (e.g., methanol, ethanol, propanol, isopropanol, butanol, etc.), etc.;

suitable aromatic alcohols include, for example, phenol, ar(lower)alkanol(e.g., benzylalcohol, phenethylalcohol, etc.;

suitable substituted pyrroles include, for example, lower alkylpyrrole(e.g., methylpyrrole, ethylpyrrole, etc.) etc.; and suitable salts of the nucleophile include, for example, metal salt(e.g., sodium salt, potassium salt, etc.), etc.;

the term "a strong nucleophile" in the term "a residue of a strong nucleophile" for Y" means a strong nucleophile given by excluding aliphatic or aromatic or heterocyclic carboxylic acid and aliphatic or aromatic or heterocyclic alcohol from nucleophile illustrated above; and particularly suitable residue of a strong nucleophile include:

(1) thiocyanato,
(2) lower alkanoylthio(e.g., acetylthio, propionylthio, butyrylthio, etc.),
(3) piperidinothiocarbonylthio,
(4) lower alkyl substituted thiadiazolylthio(e.g., 5-methyl-1,3,4-thiadiazol-2-ylthio, 5-ethyl-1,3,4-thiadiazol-2-ylthio, etc.),
(5) lower alkyl substituted imidazolylthio(e.g., 1-methylimidazol-2-ylthio, 1-ethylimidazol-2-ylthio, etc.),
(6) lower alkyl substituted tetrazolylthio(e.g., 1-methyl-1H-tetrazol-5-ylthio, 1-ethyl-1H-tetrazol-2-ylthio, etc.),
(7) benzothiazolylthio,
(8) pyridylthio,
(9) arylamino(e.g., anilino, etc.) and
(10) azide:

the term "halogen" for Y' and Z' means chlorine, bromine, fluorine, etc.:

the term "a group convertible into a residue of a nucleophile" for Z means a group which can be converted into a residue of a nucleophile by reacting with a nucleophile;

suitable group convertible into a residue of a nucleophile includes, for example, a residue of an acid, such as halogen(e.g., chlorine, bromine, fluorine, etc.), acyloxy(e.g., methanesulfonyloxy, benzenesulfonyloxy, toluenesulfonyloxy, etc.), and the like: and the term "a residue of an acid" for Z"" means a group given by omitting a hydrogen atom from an acid, such as halogen(e.g., chlorine, bromine, fluorine, etc.), acyloxy(e.g., methanesulfonyloxy, benzenesulfonyloxy, toluenesulfonyloxy, etc.), and the like.

In the above and subsequent description, the term "lower" means one to six carbon chain and the term "higher" means seven to sixteen carbon chain, which may be branched or may contain a cyclic ring.

The object compound (Ia) in the present invention can be prepared by reacting the compound (II) or the compound (III) or the compound (IV) or the compound (V) with a nucleophile.

Suitable nucleophile used in the present reaction includes, for example, thiocyanic acid, thiocyanogen, hydrazoic acid, thiourea, aliphatic or aromatic or heterocyclic thiourea, thiosemicarbazid, aliphatic or aromatic or heterocyclic thioamide, aliphatic or aromatic or heterocyclic thiol, aliphatic or aromatic or heterocyclic thiocarboxylic acid, dithiocarbonic acid ester, aliphatic or aromatic or heterocyclic dithiocarbamic acid, aliphatic or aromatic or heterocyclic amine, aminobenzoic acid, aminobenzenesulfonic acid, cyanic acid, phthalimide, succinimide, aliphatic or aromatic or heterocyclic alcohol, pyrrole, substituted pyrrole, imidazole, triazole, tetrazole or a salt thereof;

suitable aliphatic thioureas include, for example, mono- (or di or tri)lower alkylthiourea(e.g., N-methylthiourea, N,N,N'-triethylthiourea, etc.), mono(or di or tri)lower or higher cycloalkylthiourea (e.g., dicyclohexythiourea, etc.), etc.;

suitable aromatic thioureas include, for example, diarylthiourea(e.g., diphenylthiourea, etc.), lower alkyl and aryl substituted thiourea(e.g., N,N-dimethyl-N'-phenylthiourea, etc.), diar(lower)alkylthiourea(e.g., N,N'-dibenzylthiourea, etc.), lower alkyl and ar(lower)alkyl substituted thiourea(e.g., N-ethyl-N'-benzylthiourea, etc.), etc.;

suitable heterocyclic thioureas include, for example, diheterocyclic thiourea(e.g., N,N-difuryl, etc.), lower alkyl and heterocyclic substituted thiourea(e.g., N-propyl-N'-pyridylthiourea, etc.), etc.;

suitable aliphatic thioamides include, for example, thio(lower)alkaneamide(e.g., thioacetamide, thiopropionamide, etc.), etc.;

suitable aromatic thioamides include, for example, thiobenzamide, thioar(lower)alkaneamide(e.g., thiophenylacetamide, etc.), etc.;

suitable heterocyclic thioamides include, for example, thiopyridinecarboxamide, etc.;

suitable aliphatic thiols include, for example, lower alkanethiol(e.g., methanethiol, ethanethiol, propanethiol, isobutanethiol, etc.), amino(lower)alkanethiol(e.g., aminoethanethiol, etc.), di(lower)alkylamino(lower)alkanethiol(e.g., dimethylaminopropanethiol, etc.), etc.;

suitable aromatic thiols include, for example, thiophenol, aminothiophenol, dinitrithiophenol, phenyl(lower)alkanethiol(e.g., phenylmethanethiol, etc.), etc.;

suitable heterocyclic thiols may contain at least one hetero-atom such as an oxygen, nitrogen, sulfur atom and the like in the ring;

suitable heterocyclic thiols include, for example, unsaturated 3 to 8-membered heterocyclic thiol containing 1 to 4 nitrogen atom(s) in the ring(e.g., pyrrolethiol, pyrazolethiol, imidazolethiol, lower alkylimidazolethiol such as methylimidazolethiol or dihydroimidazolethiol, pyridinethiol, lower alkylpyridinethiol such as methylpyridinethiol, or tetrazolethiol, lower alkyltetrazolethiol such as methyltetrazolethiol, etc.), unsaturated condensed-heterocyclic thiol containing 1 to 3 nitrogen atom(s) in the ring(e.g., indolethiol, etc.), unsaturated 3 to 8-membered heteromonocyclic thiol containing a sulfur atom in the ring(e.g., thiophenethiol, etc.), unsaturated condensed-heterocyclic thiol containing 1 to 3 sulfur atom(s) in the ring(e.g., thianthrenethiol, etc.), unsaturated 3 to 8-membered heterocyclic thiol containing a sulfur atom and 1 to 2 nitrogen atom(s) in the ring(e.g., thiazolethiol, dihydrothiazolethiol, thiadiazolethiol, lower alkylthiadiazolethiol such as methylthiadiazolethiol, or lower alkylthiothiadiazolethiol such as ethylthiothiadiazolethiol, or aminothiadiazolethiol, etc.), unsaturated condensed-heterocyclic thiol containing a sulfur atom and 1 to 2 nitrogen atom(s) in the ring(e.g., benzothiazolethiol, etc.), unsaturated 3 to 8-membered heteromonocyclic thiol containing an oxygen atom in the ring(e.g., furanthiol, etc.), unsaturated condensed-heterocyclic thiol containing an oxygen atom and 1 to 2 nitrogen atom(s) in the ring (e.g., benzoxazolethiol, etc.), unsaturated 3 to 8-membered heteromonocyclic thiol containing an oxygen atom and 1 to 2 nitrogen atom(s) in the ring(e.g., oxadiazolethiol, lower alkyloxadiazolethiol such as propyloxadiazolethiol, etc.), etc.;
suitable aliphatic thiocarboxylic acids include, for example, thio(lower)alkanoic acid(e.g., thioacetic acid, etc.), etc.;
suitable aromatic thiocarboxylic acids include, for example, thiobenzoic acid, etc.;
suitable heterocyclic thiocarboxylic acids include, for example, thiopyridinecarboxylic acid, etc.;
suitable dithiocarbonic acid esters include, for example, lower alkyl dithiocarbonate(e.g., methyl dithiocarbonate, ethyl dithiocarbonate, etc.), ar(lower)alkyl dithiocarbonate(e.g., benzyl dithiocarbonate, etc.), etc.;
suitable aliphatic dithiocarbamic acids include, for example, N-(lower)alkyldithiocarbamic acid(e.g., N-methyl dithiocarbamic acid, etc.), N,N-di(lower)alkyldithiocarbamic acid(e.g., N,N-dimethyldithiocarbamic acid, etc.), etc.;
suitable aromatic dithiocarbamic acids include, for example, N-phenyldithiocarbamic acid, etc.;
suitable heterocyclic dithiocarbamic acids include, for example, peperidinodithiocarbamic acid, 4-lower(alkyl)-1-piperadinyldithiocarbamic acid(e.g., 4-methyl-1-piperadinyldithiocarbamic acid, etc.), etc.;
suitable aliphatic amines include, for example, mono(or di)-lower alkylamine(e.g., methylamine, diethylamine, etc.), etc.;
suitable aromatic amines include, for example, aniline, toluidine, nitroaniline, nitrotoluidine, naphthylamine, etc.;
suitable heterocyclic amines include, for example, pyrrolylamine, etc.;
suitable aliphatic alcohols include, for example, lower alkanol(e.g., methanol, ethanol, propanol, isopropanol, butanol, etc.), etc.;
suitable aromatic alcohols include, for example, phenol, ar(lower)alkanol(e.g., phenethyl alcohol, etc.), etc.;
suitable substituted pyrroles include, for example, lower alkylpyrrole(e.g., methylpyrrole, ethylpyrrole, etc.), etc.;
suitable salts of the nucleophile include, for example, metal salt(e.g., sodium salt, potassium salt, etc.), etc.

The present reaction is usually carried out in the presence of a solvent such as water, lower alcohol, chloroform, acetic acid, methylenechloride, acetone, acetonitrile, formamide, tetrahydrofuran, dioxane or other any solvent which does not give bad influence to the present reaction.

When the compound (II) is used as a starting compound in the reaction, the present reaction is preferably carried out in the presence of a removing agent of a thiol compound HR$^4$, such as Lewis acid(e.g., sulfuric acid, benzenesulfonic acid, toluenesulfonic acid, polyphosphoric acid, aluminum chloride, titanium chloride, boron fluoride, etc.), cupric oxide, silver nitrate, silver fluoride, silver oxide, silver carbonate, mercuric oxide, mercuric sulfate, mercuric acetate, silver fluoroborate, silver perchlorate, silver isocyanate and the like.

When the compound (III) is used as a starting compound in the reaction, the present reaction is preferably carried out in the presence of Lewis acid such as sulfuric acid, benzenesulfonic acid, toluenesulfonic acid, polyphosphoric acid, aluminum chloride, titanium chloride, boron fluoride and the like.

When the compound (IV) or (V) wherein Z is halogen, is used as the starting compound in the reaction, the present reaction is preferably carried out in the presence of a dehydrohalogenation agent such as silver fluoroborate, silver isocyanate, silver perchlorate, silver acetate and the like.

When water is used as a solvent in the reaction, the present reaction is preferably carried out at around pH7, and when an organic solvent such as formamide is used as a solvent, the present reaction is preferably carried out in the presence of an inorganic base such as alikali metal (e.g., sodium, potassium, etc.), alkaline earth metal (e.g., magnesium, calcium, etc.), hydroxide or carbonate and bicarbonate thereof, and the like, or an organic base such as trialkylamine (e.g., trimethylamine, triethylamine, etc.), pyridine, δ-picoline, 1,8-diazabicyclo-[5,4,0]undecene-7, 1,5-diazabicyclo [4,3,0]none-5-ene, 1,4-diazabicyclo[2,2,2]octane, quarternaryammoniumhydroxide compound and the like.

There is no particular limitation to the reaction temperature, and the present reaction can be sufficiently carried out at room temperature.

The present invention includes, within its scope, the case that the protected carboxy group is changed into the other protected carboxy group or into the free carboxy group during the reaction or post-treating in the present reaction.

According to the process of the present invention, the object compound (Ia), wherein A is the group of the formula:

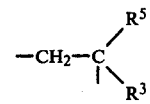

can be also prepared by reacting the compound (III) with a Lewis acid.

This reaction is usually carried out in the presence of a solvent such as methylenechloride, chloroform, benzene, tetrahydrofuran, dimethylformamide or other solvent which does not give bad influence to this reaction.

Suitable Lewis acid used in this reaction includes, for example, boron halide (e.g., boron chloride, boron bromide, boron fluoride, etc.), titanium halide (e.g., titanium chloride, titanium bromide, etc.), zirconium halide (e.g., zirconium chloride, zirconium bromide, etc.), stannic halide (e.g., stannic chloride, stannic bromide, etc.), antimony halide (e.g., antimony trichloride, antimony pentachloride, etc.), bismuth chloride, aluminum halide (e.g., aluminum chloride, aluminum bromide, etc.), zinc chloride, ferric chloride, toluenesulfonic acid, polyphosphoric acid ester, sulfuric acid, trichloroacetic acid, trifluoroacetic acid, zinc sulfate, ferric sulfate, zinc nitrite, ferric nitrite, etc.

There is no particular limitation to the reaction temperature.

The object compound (Ib) and the compound (VII) and the compound (XVII) can be prepared by oxydizing the compound (Ia) and the compound (VI), and the compound (XVI), respectively.

The present oxydizing reaction is carried out under conditions that the —S— group can be changed into the

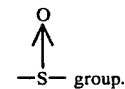 group.

Suitable oxydizing methods to be employed in this reaction are a method using a oxydizing agent, for example, isocyanuroyl chloride, phenyliodododichloride, ozone, inorganic per acid (e.g., periodic acid, persulfuric acid, etc.), organic per acid (e.g., perbenzoic acid, m-chloroperbenzoic acid, performic acid, peracetic acid, chloroperacetic acid, trifluoroperacetic acid, etc.), a metal salt of the inorganic or organic peracid, hydrogen peroxide, etc.

The present invention is preferably carried out in the presence of a compound containing a Group Vb or VIb metal in the Periodic Table, for example, tungstic acid, molybdic acid, vanadic acid, or the like, or an alkali metal (e.g., sodium, potassium, etc.), alkaline earth metal (e.g., calcium, magnesium, etc.), ammonium salt thereof, or vanadium pentoxide.

The present oxydizing reaction is usually carried out in the presence of a solvent such as chloroform, methylenechloride, pyridine, water, tetrahydrofuran, dimethylformamide, dioxane, acetic acid or other solvent which does not give bad influence to the present reaction.

There is no particular limitation to the reaction temperature, and the present reaction is usually carried out at room temperature to under cooling.

The present invention includes, within its scope, the case that the protected carboxy group is changed into the other protected carboxy group or into the free carboxy group during the reaction or post-treating in the present reaction.

The compound (IX) in the present invention can be prepared by subjecting the compound (VIII) to elimination reaction of the protective group of amino.

The present elimination reaction is carried out in accordance with a conventional method such as a method using an acid or hydrazine, reduction, and the like. These methods may be selected depending on the kind of the protective groups to be eliminated. When the protective group is an acyl group, it may also be eliminated by treating with an iminohalogenating agent and then with an iminoesterifying agent, if necessary, followed by hydrolysis. The elimination reaction with the acid is one of the most commonly applied methods for the protective groups such as benzyloxycarbonyl, substituted benzyloxycarbonyl, alkoxycarbonyl, substituted alkoxycarbonyl, aralkoxycarbonyl, adamantyloxycarbonyl, trityl, substituted phenylthio, substituted aralkylidene, substituted alkylidene, substituted cycloalkylidene, etc. Suitable acid in this case is an acid which can be easily distilled off under reduced pressure. Suitable acid includes formic acid, trifluoroacetic acid, benzenesulfonic acid, p-toluenesulfonic acid, and the like.

The acid suitable for the reaction can be selected according to the protected group to be eliminated and other circumstances. When the elimination reaction with the acid may be carried out in the presence of a solvent, such as a hydrophilic organic solvent, water or a mixed solvent thereof. The elimination reaction with hydrazine is commonly applied for, for example, phthaloyl. The reduction is generally applied for, for example, trichloroethoxycarbonyl, benzyloxycarbonyl, substituted benzyloxycarbonyl, 2-pyridylmethoxycarbonyl, etc.

The reduction applicable for the elimination reaction of the present invention may include, for example, reduction using a metal (e.g., tin, zinc, iron, etc.) or a combination of metalic compound (e.g., chromous chloride, chromous acetate etc.) and an organic or inorganic acid (e.g., acetic acid, propionic acid, hydrochloric acid, etc.), and reduction in the presence of a metalic catalyst for catalytic reduction. The metalic catalysts for catalytic reduction include, for example, Raney-nickel, platinum oxide, palladium carbon and other conventional catalysts. The protective group, trifluoroacetyl can be usually eliminated by treating with water in the presence or absence of the base, and halogen substituted-alkoxycarbonyl and 8-quinolyloxycarbonyl are usually eliminated by treating with a heavy metal such as cupper, zinc, etc. When the protective group is acyl, the acyl can be eliminated by reacting with the iminohalogenating agent and then with the iminoetherifying agent, if necessary, followed by hydrolysis. Suitable iminohalogenating agents include, for example, phosphorus trichloride, phosphorus pentachloride, phosphorus tribromide, phosphorus pentabromide, phosphorus oxychloride, thionyl chloride, phosgene, etc. Iminohalogenating reaction temperature is not limitative and the reaction sufficiently proceeds under ambient temperature or cooling. Suitable iminoetherifying agents, with which the resultant in the iminohalogenating reaction is reacted, include an alcohols such as an alkanol (e.g., methanol, ethanol, propanol, isopropanol, butanol, tertiary butanol, etc.) or the corresponding alkanol having alkoxy (e.g., methoxy, ethoxy, propoxy, isopropoxy, buthoxy, etc.) as substituent(s) at the alkyl moiety thereof and a metal alkoxide such as alkali metal alkoxide (e.g., sodium alkoxide, potassium alkoxide, etc.) or alkaline earth metal alkoxide (e.g., calcium alkoxide, barium alkoxide, etc.) derived from the said alcohol. The iminoetherifying reaction temperature is also not limitative and the reaction sufficiently proceeds under ambient temperature or cooling. Thus obtained reaction product is, if necessary, hydrolyzed. The hydrolysis sufficiently proceeds by pouring the reaction mixture to water or a mixture of water and a hydrophilic solvent such as methanol, ethanol, etc. In this hydrolysis, water may contain a base such as alkali metal bicarbonate, trialkylamine, etc. or an acid such as dilute hydrochloric acid, acetic acid, etc. When the protective group is acyl, the acyl can be eliminated by hydrolysis as mentioned above or by other conventional hydrolysis.

The reaction temperature is not limitative and may be suitable selected in accordance with the protective group for amino and the elimination method, and the present reaction is preferably carried out under a mild condition such as under cooling or slightly warming.

The present invention includes the case that the protected carboxy group is changed into the other protected carboxy or into the free carboxy group during the present reaction or post-treating in the present reaction.

Thus obtained compound of (IX) can be converted to a desirable acid addition salt thereof by a conventional method, if necessary.

The compound (X) in the present invention can be prepared by reacting the compound (IX) or a salt thereof with an acylating agent.

Suitable salt of the compound (IX) includes organic acid salt (e.g., acetate, maleate, tartrate, benzenesulfonate, toluenesulfonate, etc.) and inorganic acid salt (e.g., hydrochloride, sulfate, phosphate, etc.), and the like.

As acylating agents in the present reaction, there may be exemplified an aliphatic, aromatic and heterocyclic carboxylic acid, and the corresponding sulfonic acid, carbonic acid ester, carbamic acid and thio acid, and the reactive derivatives of the above acids.

As the reactive derivatives, there may be exemplified an acid anhydride, an activated amide, an activated ester, an isocyanate and an isothiocyanate, etc., and exemplified concretely an acid azide, an mixed acid anhydride with an acid such as dialkylphosphoric acid, phenylphosphoric acid, diphenylphosphoric acid, dibenzylphosphric acid, halogenated phosphoric acid, dialkylphosphorous acid, sulfurous acid, thiosulfuric acid, hydrohalogenic acid (e.g., acid chloride), sulfuric acid, monoalkyl carbonate aliphatic carboxylic acid (e.g., acetic acid, pivalic acid, pentanoic acid, isopentanoic acid, 2-ethylbutyric acid or trichloroacetic acid), aromatic carboxylic acid (e.g., benzoic acid), or symmetrical acid anhydride, an acid amide with pyrazole, imidazole, 4-substitutedimidazole, dimethylpyrazole, triazole or tetrazole, an ester (e.g., cyanomethyl ester, methoxymethyl ester, vinyl ester, propargyl ester, p-nitrophenyl ester, 2,4-dinitrophenyl ester, trichlorophenyl ester, pentachlorophenyl ester, methanesulfonylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or ester with N,N-dimethylhydroxylamine, 1-hydroxy-2-(1H)-pyridone. N-hydroxysuccinimide or N-hydroxyphthalimide).

The above reactive derivative are selected according to the kind of the acid to be used. In the acylating reaction, when free acid is used, there may be preferably added a condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonyldi(2-methylimidazole), pentamethyleneketene-N-cyclohexylimide, diphenylketene-N-cyclohexylimine, alkoxyacetylene, 1-alkoxyl-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, 2-ethyl-7-hydroxybenzisoxazolium salt, 2-ethyl-5-(m-sulfophenyl)-isoxazolium hydroxide intramolecular salt, (chloromethylene)-dimethylammonium chloride, 2,2,4,4,6,6-hexachloro-2,2,4,4,6,6-hexahydro-1,3,5,2,4,6-triazatriphosphorine, or a mixed condensing agent such as triphenylphosphine and a carbon tetrahalide (e.g., carbon tetrachloride, carbon tetrabromide, etc.) or a halogen (e.g., chlorine, bromine, etc.), and the like.

The example of an acyl group to be introduced into the amino group by the above acylating agent may be a group dehydroxylated from each of an aliphatic aromatic and heterocyclic carboxylic acid, and the corresponding sulfonic acid, carbonic acid ester, carbamic acid and thio acid, etc., and more particular acyl group can be the same acyl group as illustrated in the explanation of the acyl group in the acylamino group for $R^1$.

The present acylating reaction is usually carried out in a solvent which does not give bad influence to the reaction, for example, water, acetone, dioxane, acetonitrile, chloroform, methylenechloride, ethanedichloride, tetrahydrofuran, ethyl acetate, dimethylformamide, pyridine, etc., and a hydrophilic solvent mentioned above can be used as a mixed solvent with water.

The present acylating reaction can be carried out in the presence of a base such as inorganic base (e.g., alkali metal bicarbonate, etc.) and organic base (e.g., trialkylamine, N,N-dialkylamine, N,N-dialkylbenzylamine, pyridine, 1,5-diazabicyclo[4,3,0]non-5-ene, 1,4-diazabicyclo[2,2,2]octane, 1,8-diazabicyclo[5,4,0]undecene-7, etc.).

In the present reaction, a liquid base or liquid condensing agent can be used as a solvent.

There is no limitation to the present reaction, and the present reaction can be carried out under cooling or at room temperature.

The present invention includes the case that the protected carboxy is changed into the other protected carboxy group or into the free carboxy group in the present reaction of post-treating in the present reaction.

The compound (IV), wherein Z is halogen, can be prepared by reacting the compound (II) or (III) with a hydrogen halide or a metal halide. Suitable hydrogen halide used in the present reaction includes, for example, hydrogen chloride, hydrogen bromide, hydrogen iodide, etc., and suitable metal halide includes mercuric chloride, cupric chloride, zinc chloride, etc.

The present reaction is usually carried out in a solvent which does not give bad influence to the reaction, for example, lower alcohol, chloroform, acetic acid, methylenchloride, acetone, acetonitrile, etc. There is no particular limitation to the present reaction temperature, and the reaction temperature may be suitably selected in accordance with the kinds of the compound (II) or (III), hydrogen halide or metal halide, etc.

The present invention includes the case that the protected carboxy group is changed into the other protected carboxy or onto the free carboxy group in the present reaction or post-treating in the present invention.

The compound (V), wherein Z is halogen, can be prepared by subjecting the compound (IV), wherein Z is halogen, to rearrangement reaction. The present rearrangement reaction can be carried out by leaving or warming or heating the reaction mixture obtained by reacting the compound (II) or (III) with a hydrogen halide or a metal halide, or by leaving or warming or heating the compound (IV), wherein Z is halogen, isolated from said reaction mixture with or without solvent, or by subjecting the compound (IV), wherein Z is halogen, to column chromatography on silica gel.

Suitable solvent in the present reaction includes any solvent which does not give bad influence to the reaction, for example, water, acetone, methylenechloride, acetonitrile, chloroform, tetrahydrofuran, tertiary butanol, isopropanol, benzene, dioxane, dimethylformamide, dimethylsulfoxide, pyridine, and the like.

The present reaction may be preferably carried out in the presence of Lewis acid or Lewis base.

The present invention includes the case that the protected carboxy group is changed into the other protected carboxy or into the free carboxy group in the present reaction or post-treating in the present reaction.

The compound (II) can be prepared by reacting the compound (XV) with a thiol compound or a salt thereof.

Suitable thiol compound used in the present reaction includes a substituted or unsubstituted, aliphatic thiol, aromatic thiol or heterocyclic thiol.

Suitable aliphatic thiol includes, for example, lower alkane thiol (e.g., methanethiol, ethanethiol, propanethiol, isopropanethiol, butanethiol, isobutanethiol, etc.), lower alkenethiol (e.g., 1-isopropenethiol, 3-butenethiol, etc.), etc.

Suitable substituted aliphatic thiol includes, for example, lower alkyloxy(lower)alkanethiol (e.g., methoxymethanethiol, ethoxyethanethiol, etc.), ar(lower)alkanethiol (e.g., phenylmethanethiol, phenylethanethiol, xylylmethanethiol, etc.), halophenyl(lower)alkanethil (e.g., 4-chlorophenylmethanethiol, 4-bromophenylmethanethiol, etc.), nitrophenyl(lower)alkanethiol (e.g., 4-nitrophenylethanethiol, etc.), mono (or di)-lower alkoxyphenyl(lower)alkanethiol (e.g., 4-methoxyphenylmethanethiol, 2,4-dimethoxyphenylmethanethiol, etc.), halogen and lower alkoxy substitued phenyl(lower)alkanethiol (e.g., 2-chloro-4-methoxyphenylmethanethiol, etc.), etc.

Suitable aromatic thiol includes arenethiol (e.g., benzenethiol, xylenethiol, toluenethiol, naphthalenethiol, etc.).

Suitable substituted aromatic thiol includes, for example, mono(or di) halobenzenethiol (e.g., chlorobenzenethiol, bromobenzenethiol, dichlorobenzenethiol, etc.), nitrobenzenethiol, mono(or di)-lower alkxoybenzenethiol (e.g., methoxybenzenethiol, dimethoxybenzenethiol, etc.), halogen and nitro substituted benzenethiol (e.g., chloronitrobenzenethiol, etc.), etc.

Suitable heterocyclic in the heterocyclic thiol may contain at least one hetero-atom such as an oxygen, nitrogen, sulfur atom and the like. Suitable heterocyclic includes, for example, unsaturated 3 to 8-membered heteromonocyclic containing a sulfur atom (e.g., thiophene, etc.), unsaturated 3 to 8-membered heteromonocyclic containing an oxygen atom (e.g., furan, etc.), unsaturated 3 to 8-membered heteromonocyclic containing 1 to 4 nitrogen atom(s) (e.g., pyrrole, pyridine, imidazole, triazole, tetrazole, etc.), saturated 3 to 8-membered heteromonocyclic containing 1 to 2 nitrogen atom(s) (e.g., pyrrolidine, piperazine, piperizine, homopiperizine, etc.), unsaturated condensed-heterocyclic containing 1 to 3 nitrogen atom(s) (e.g., quinoline, isoquinoline, benzimidazole, etc.), unsaturated 3 to 8-membered heteromonocyclic containing an oxygen atom and 1 to 3 nitrogen atom(s) (e.g., oxazole, oxadiazole, oxatriazole, etc.), unsaturated 3 to 8-membered heteromonocyclic containing a sulfur and 1 to 3 nitrogen atom(s) (e.g., thiazole, thiadiazole, thiatriazole, etc.), unsaturated condensed heterocyclic containing an oxygen and nitrogen atom (e.g., benzoxazole, etc.), unsaturated condensed-heterocyclic containing a sulfur and nitrogen atom (e.g., benzothiazole, etc.); and suitable substituted heterocyclic in the substituted heterocyclic thio includes, for example, the above mentioned heterocyclic are substituted with 1 to 6 appropriate substituent(s) such as lower alkyl (e.g., methyl, ethyl, etc.), a lower alkoxy (e.g., methoxy, ethoxy, etc.), a halogen atom (e.g., fluroine, chlorine, bromine, etc.), a nitro, an aryl (e.g., phenyl, tolyl, xylyl, etc.), a substituted aryl (e.g., chlorophenyl, nitrophenyl, etc.), an ar(lower) alkyl (e.g., benzyl, phenethyl, etc.) or the like.

Suitable salt of the thiol compound includes metal salt such as sodium salt, potassium salt, and the like. When the compound (XV) wherein X is halogen is used in the present reaction, the present reaction is preferably carried out in the presence of a removing agent of halogen, for example, base. When a liquid thiol compound is used in the present reaction, the liquid thiol compound can be used as a solvent.

The present reaction is usually carried out in a solvent which does not give bad influence to the reaction.

Suitable solvent includes, for example, acetone, water, dioxane, tetrahydrofuran, methylenchloride, chloroform, phosphate buffer, etc.

The present invention includes, within its scope, the case that the compound (II) wherein $R^4$ is a group of the formula:

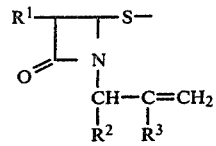

which is derived from the compound (XV) other than the thiol compound, may be also obtained in the present reaction.

There is no limitation to the reaction temperature, and the present reaction can be carried out under room temperature.

The present invention includes the case that the protected carboxy group is changed into the other protected carboxy or into the free carboxy group in the present reaction or post-treating in the present reaction.

The compound (XII) in the present invention can be prepared by subjecting the compound (XI) to elimination reaction of the protective group of carboxy and the compound (XIV) in the present invention can be prepared by subjecting the compound (XIII) to elimination reaction of the protective group of carboxy. In the present elimination reaction, all conventional methods used in the elimination reaction, all conventional methods used in the elimination reaction of the protected carboxy, for example, reduction, hydrolysis, etc. can be applicable. When the protected group is an active ester, active amide, acid halide or acid azide, those can be eliminated by hydrolysis, usually eliminated under mild hydrolysis conditions such as by contacting with water. The reduction can be applicable for, for example, 2-iodoethyl ester, 2,2,2-trichloroethyl ester, benzyl ester, etc. The elimination reaction with an acid can be applicable for the protected groups such as p-methoxybenzyl ester, tert-butyl ester, tert-pentyl ester, trityl ester, diphenylmethyl ester, bis(methoxyphenyl)methyl ester, 3,4-dimethoxybenzyl ester, 1-cyclopropylethyl ester, and the like. The elimination reaction with an anhydrous basic catalyst can be applicable for the protective groups such as ethynyl ester, 4-hydroxy-3,5-di(tert-butyl)benzyl ester, and the like. The reduction applicable for the elimination reaction of the present invention may include, for example, reduction using a metal (e.g., zinc, zinc amalgam, etc.) or a chromous salt compound (e.g., chromous chloride, chromous acetate and an organic or inorganic acid (e.g., acetic acid, propionic acid, hydrochloric acid, etc.), and reduction in the presence of a metalic catalytic reduction. The metalic catalysts for catalytic reduction include, for example, platinum catalyst (e.g., platinum wire, spongy platinum, platinum black, platinum colloid, etc.), palladium catalyst (e.g., palladium spongy, palladium black, palladium oxide, palladium on barium sulfate, palladium on barium carbonate, palladium on charcoal, palladium on silica gel, palladium colloid, etc.), nickel catalyst (e.g., reduced nickel, nickel oxide, Raney nickel, Urushibara nickel, etc.), etc. Suitable acid used for the elimination reaction includes, for example, formic acid, trihaloacetic acid (e.g., trichloroacetic acid, trifluoroacetic acid, etc.), hydrochloric acid, hydrofluoric acid, p-toluenesulfonic acid, trifluoromethanesulfonic acid, mixed acid or hydrochloric acid and acetic acid, etc.), etc.

Suitable anhydrous basic catalyst for the elimination reaction includes, for example, sodium thiophenophenate, $(CH_3)_2LiCu$, etc. When the protective group is eliminated by treating with water or a liquid acid in the reaction, the present reaction can be carried out without solvent. When a solvent is used in the present reaction, any solvent which does not give bad influence to the present reaction, for example, dimethylformamide, methylenchloride, chloroform, tetrahydrofuran, acetone, and the like can be used in the present reaction.

There is no particular limitation to the reaction temperature, and it may be suitably selected according to the starting compound and an elimination method to be practically applied. The present invention includes the case that a protected carboxy, hydroxy, mercapto or amino group contained in the starting compound is changed into the corresponding carboxy, hydroxy, mercapto or amino group respectively in the present reaction or post-treating in the present reaction. Thus obtained the compound (XII) or (XIV) can be converted to a desirable metal (e.g., sodium, potassium, etc.) salt or organic base salt thereof, if necessary.

Having now generally described the invention, a further understanding can be attained by reference to certain specific examples which are provided herein for purposes of illustration only and are not intended to be construed as limiting unless otherwise so indicated.

Reaction of:

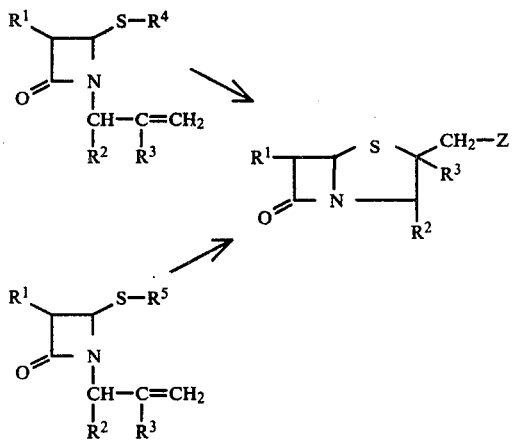

EXAMPEL 1

2,2,2-Trichloroethyl 2-oxo-3-(2-phenoxyacetamido)-4-(benzothiazol-2-yl)dithio-α-isopropenyl-1-azetidineacetate (0.65 g) was dissolved in chloroform (15 ml). To this solution was added cupric chloride (0.16 g) and then the mixture was stirred for 8 hours at room temperature. Precipitates were filtered off and the filtrate was washed with a saturated sodium bicarbonate aqueous solution and then with water and thereafter dried over magnesium sulfate. The solvent was distilled off to give oily 2,2,2-trichloroethyl 2-chloromethyl-2-methyl-6-(2-phenoxyacetamido) penam-3-carboxylate (0.56 g).

Infrared Absorption Spectrum (Film): 3350, 1785, 1760, 1685 cm$^{-1}$

EXAMPLE 2

2,2,2-Trichloroethyl 2-oxo-3-(2-phenylacetamido)-4-(benzothiazol-2-yl)dithio-α-isopropenyl-1-azetidineacetate (0.63 g) was dissolved in chloroform (15 ml). To this solution was added cupric chloride (0.16 g) and then the mixture was stirred for 8 hours at room temperature. Precipitates were filtered off and the filtrate was washed with a saturated sodium bicarbonate aqueous solution and then with water and thereafter dried over magnesium sulfate. The crystals obtained by distilling off the solvent were washed with ether to give 2,2,2-trichloroethyl 2-chloromethyl-2-methyl-6-(2-phenylacetamido)penam-3-carboxylate (0.45 g), mp 108° to 109° C.

Infrared Absorption Spectrum (Nujol): 3300, 1785, 1763, 1656 cm$^{-1}$.

EXAMPLE 3

2,2,2-Trichloroethyl 2-oxo-3-(2-phenylacetamido)-4-(benzothiazol-2-yl)dithio-α-isopropenyl-1-azetidineacetate (0.63 g) was dissolved in acetonitrile (12 ml). To this solution was added mercuric chloride (0.44 g) and then the mixture was stirred for 24 hours at room temperature. After the reaction, precipitates were filtered off and the filtrate was concentrated under reduced pressure and the obtained residue was dissolved in ethyl acetate. The ethyl acetate layer was washed with water, dried and the solvent was distilled off. The obtained residue was purified by chromatography on silica gel to give colorless needles of 2,2,2-trichloroethyl 2-chloromethyl-2-methyl-6-(2-phenylacetamido)penam-3-carboxylate (190 mg), mp 104° to 105° C., from the third and fourth fractions of fractions each of which was separated into 50 ml.

Infrared Absorption Spectrum (Nujol): 3300, 1785, 1763, 1656 cm$^{-1}$.

EXAMPLE 4

To a solution of methyl 2-oxo-3-(2-phenoxyacetamido)-4-anilinothio-α-isopropenyl-1-azetidineacetate (0.12 g), in dried methylene chloride (5 ml) was added 5% methanolic hydrochloric acid (0.8 ml) and the mixture was stirred for 10 hours at room temperature. After the reaction, methylene chloride was distilled off under reduced pressure from the reaction mixture. The residue was extracted with ethyl acetate and the extract was washed with water and dried. The solvent was distilled off to give oily methyl 2-chloromethyl-2-methyl-6-(2-phenoxyacetamido)-penam-3-carboxylate (0.085 g).

Infrared Absorption Spectrum (Chloroform): 3400, 1790, 1760, 1680 cm$^{-1}$.

EXAMPLE 5

There was obtained oily methyl 2-chloromethyl-2-methyl-6-(2-phenoxyacetamido)-penam-3-carboxylate (0.36 g) by treating in the similar manner as described in Example 4 using methyl 2-oxo-3-(2-phenoxyacetamido)-4-propylaminothio-α-isopropenyl-1-azetidineacetate (0.43 g).

The following compounds were obtained by using the same procedures as those of the Example (1) 2,2,2-Trichloroethyl 2-bromomethyl-2-methyl-6-(2-phenylacetamido)penam-3-carboxylate mp 90° to 93° C. (dec.).

(2) 2,2,2-Trichloroethyl 2-bromomethyl-2-methyl-6-[N-(2,2,2-trichloroethoxy)-carbonylphenylglycyl-]aminopenam-3-carboxylate (powder)

(3) 2,2,2-Trichloroethyl 2-bromomethyl-2-methyl-6-(2-phenoxyacetamido)-penam-3-carboxylate (gummy).

(4) 1-Cyclopropylethyl 2-bromomethyl-2-methyl-6-(2-phenylacetamido)-penam-3-carboxylate (oil).
(5) 2,2,2-Trichloroethyl 2-bromomethyl-2-methyl-6-[2-(sydnon-3-yl)acetamido]penam-3-carboxylate (amorphous).
(6) 2,2,2-Trichloroethyl 2-bromomethyl-2-methyl-6-[2-(4-hydroxyphenyl)-2-(1-cyclopropylethoxy)carbonylaminoacetamido]penam-3-carboxylate (powder).
(7) 2,2,2-Trichloroethyl 2-bromomethyl-2-methyl-6-[2-(2-thienyl)acetamido]-penam-3-carboxylate (oil).
(8) 3,5-Di-tert.-butyl-4-hydroxybenzyl-2-bromomethyl-2-methyl-6-(2-phenylacetamido)penam-3-carboxylate (white crystalline powder).
(9) 2,2,2-Trichloroethyl 2-bromomethyl-2-methyl-6-[N-(1-cyclopropylethoxy)-carbonylphenylglycyl]aminopenam-3-carboxylate (mp 130° to 135° C.).
(10) 2,2,2-Trichloroethyl 2-bromomethyl-2-methyl-6-(2-cyanoacetamido)-penam-3-carboxylate (amorphous).

Reaction of:

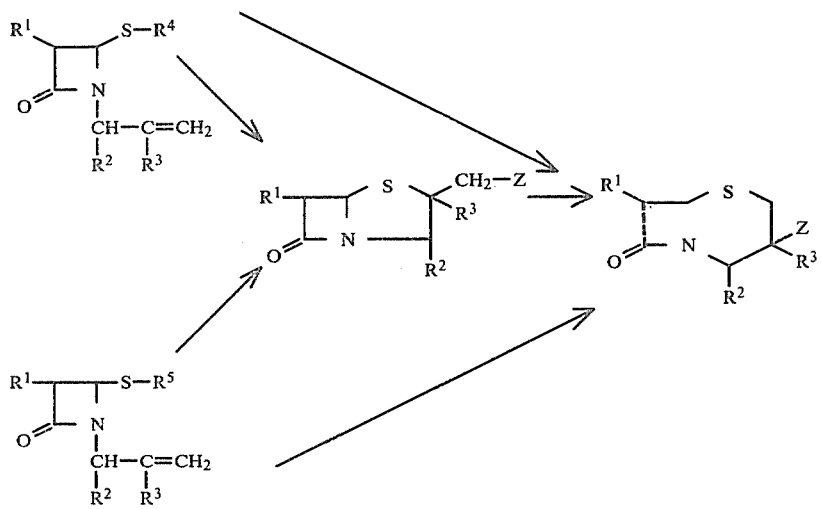

EXAMPLE 1

2,2,2-Trichloroethyl 2-oxo-3-(2-phenylacetamido)-4-(benzothiazol-2-yl)dithio-α-isopropenylazetidine-1-acetate (0.63 g) was dissolved in acetonitrile (12 ml). To this solution was added mercuric chloride (0.44 g) and the mixture was stirred for 24 hours at room temperature. After the reaction, precipitates were filtered off and the filtrate was concentrated under reduced pressure. The obtained residue was dissolved in ethyl acetate and the ethyl acetate layer was washed with water and then dried. The solvent was distilled off and the obtained residue was purified by column chromatography on silica gel to give powdery 2,2,2-trichloroethyl 3-chloro-3-methyl-7-(2-phenylacetamido)cepham-4-carboxylate (70 mg) from the fifth and sixth fractions of fractions each of which was separated into 50 ml.

Infrared Absorption Spectrum (Nujol): 3400, 1775, 1760, 1675 cm$^{-1}$.

EXAMPLE 2

2,2,2-Trichloroethyl 2-oxo-3-(2-phenyl-acetamido)-4-(benzothiazol-2-yl)-dithio-α-isopropenylazetidine-1-acetate (1.26 g) was dissolved in methylene chloride (15 ml). To this solution was added dried zinc chloride (0.40 g) and the mixture was stirred for 2 days at room temperature. After the reaction, the reaction mixture was filtered and the filtrate was washed with sodium bicarbonate aqueous solution and then with water. The residue was subjected to column chromatography on silica gel (20 g) and eluted with chloroform. The third fraction of the fractions each of which was separated in about 30 ml was separated and the solvent was distilled off to give powdery 2,2,2-trichloroethyl 3-chloro-3-methyl-7-(2-phenylacetamido)cepham-4-carboxylate.

EXAMPLE 3

Methyl 2-oxo-3-(2-phenoxyacetamido)-4-anilinothio-α-isopropenylazetidine-1-acetate (0.12 g) was dissolved in dry methylene chloride (5 ml). To this solution was added 5% methanolic hydrochloric acid (0.8 ml) and the mixture was stirred for 10 hours at room temperature. After the reaction, the reaction mixture was concentrated under reduced pressure and the residue was extracted with ethyl acetate. The extract was washed with water and dried. The solvent was distilled off and the residue was subjected to column chromatography on silica gel using chloroform as developing solvent to give oily methyl 3-chloro-3-methyl-7-(2-phenoxyacetamido)cepham-4-carboxylate (0.07 g).

Infrared Absorption Spectrum (Chloroform): 3410, 1775, 1742, 1690 cm$^{-1}$.

EXAMPLE 4

Methyl 2-oxo-3-(2-phenoxyacetamido)-4-propylaminothio-α-isopropenylazetidine-1-acetate (0.43 g) was dissolved in dried methylene chloride. To this solution was added 5% methanolic hydrochloric acid (2 ml) and the mixture was stirred for 10 hours at room temperature. After the reaction, the reaction mixture was concentrated under reduced pressure and the residue was extracted with ethyl acetate. The extract was washed with water and dried. The solvent was distilled off and the residue was subjected to column chromatography on silica gel using chloroform as developing solvent to give oily methyl 3-chloro-3-methyl-7-(2-phenoxyacetamido)cepham-4-carboxylate (310 mg).

The following compounds were obtained by using the same procedures as those of the Examples 1 to 4.

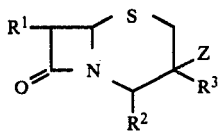

| No. | R¹ | R² | R³ | Z | Property of the product |
|---|---|---|---|---|---|
| 1 | [phenyl]-OCH₂CONH— | —COOCH₃ | —CH₃ | —Br | amorphous |
| 2 | [phenyl]-OCH₂CONH— | —COOCH₃ | —CH₃ | —I | oil |
| 3 | [phenyl]-OCH₂CONH— | —COOH | —CH₃ | —Br | amorphous |
| 4 | [phenyl]-CH₂CONH— | —COOCH₂CCl₃ | —CH₃ | —Br | mp 90° to 93° C. (dec.) |
| 5 | NC—CH₂CONH— | —COOCH₂CCl₃ | —CH₃ | —Br | amorphous |
| 6 | [thiophene]-CH₂CONH— | —COOCH₂CCl₃ | —CH₃ | —Br | oil |

Reaction of:

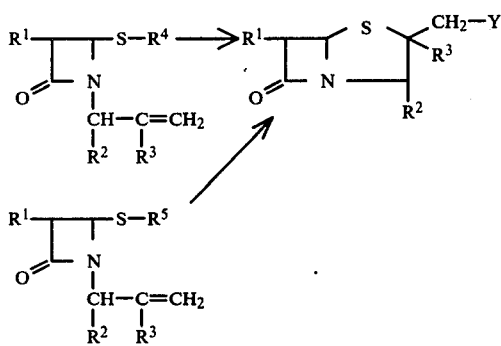

EXAMPLE 1

Methyl 2-oxo-3-(2-phenoxyacetamido)-4-(benzothiazol-2-yl)dithio-α-isopropenyl-1-azetidine-acetate (1.06 g) and silver acetate (0.34 g) were suspended in tert-butanol and the mixture was refluxed for 48 hours. After the reaction, precipitates were filtered off and the filtrate was concentrated under reduced pressure. The residue was extracted with ethyl acetate. The ethyl acetate layer was washed with water, dried and the solvent was distilled off. The obtained residue was purified by column chromatography on silica gel using chloroform as developing solvent to give pale yellow oil of methyl 2-acetoxymethyl-2-methyl-6-(2-phenoxyacetamido)-penam-3-carboxylate (490 mg).

Infrared Absorption Spectrum (CHCl₃): 3410, 1792, 1745, 1740, 1690 cm⁻¹.

EXAMPLE 2

2,2,2-Trichloromethyl 2-oxo-3-(2-phenylacetamido)-4-(benzothiazol-2-yl)-dithio-α-isopropenyl-1-azetidine-acetate (0.63 g) was dissolved in chloroform (10 ml). To this solution was added lead tetraacetate (1.77 g) and the mixture was refluxed for 24 hours. To the reaction mixture was added water and precipitates were filtered off. The filtrate was separated into chloroform layer and aqueous layer and the aqueous layer was extracted with chloroform. The chloroform layer was combined, dried over magnesium sulfate and then the solvent was distilled off. The residue was prufied by column chromatography on silica gel using chloroform as developing solvent to give 2,2,2-trichloroethyl 2-acetoxymethyl-2-methyl-6-(2-phenylacetamido)-penam-3-carboxylate (0.11 g), mp 122° to 123° C.

EXAMPLE 3

2,2,2-Trichloroethyl 2-oxo-6-(2-phenylacetamido)-4-(benzothiazol-2-yl)dithio-α-isopropenyl-1-azetidineacetate (1.26 g) was dissolved in a mixture of chloroform (10 ml) and acetic acid (10 ml). To this solution was added lead tetraacetate (1.80 g) and the mixture was stirred for 7 hours at room temperature. Lead tetraacetate (1.80 g) was further added to this solution and the solution was stirred for 8 hours at 50° C. To the reaction mixture was added chloroform, and the solution was washed with a saturated sodium bicarbonate aqueous solution and then with water and thereafter dried over magnesium sulfate. The residue obtained by distilling off the solvent was purified by column chromatography on silica gel using chloroform as developing solvent to give 2,2,2-trichloroethyl 2-acetoxymethyl-2-methyl-6-(2-phenylacetamido)penam-3-carboxylate (0.26 g).

Infrared Absorption Spectrum (Nujol): 3280, 1792, 1748, 1660 cm⁻¹.

EXAMPLE 4

2,2,2-Trichloroethyl 2-oxo-3-[N-(1-cyclopropylethoxy)carbonylphenylglycyl]-amino-4-(benzothiazol-2-yl)dithio-α-isopropenyl-1-azetidinoacetate (1.52 g) was dissolved in dry methylene chloride (15 ml) under ice-cooling. To this solution was dropwise added a solution of thiocyanogen (1 m mole) in methylene chloride (10 ml) and the mixture was stirred for 24 hours at the same temperature. Precipitates were filtered off and the filtrate was washed with a saturated sodium bicarbonate aqueous solution and then with water. After drying over magnesium sulfate, the solvent was distilled off under reduced pressure to give oily 2,2,2-trichloroethyl 2-thiocyanatomethyl-2-methyl-6-[N-(1-cyclopropylethoxy)carbonylphenylglycyl]aminopenam-3-carboxylate (1.3 g).

Infrared Absorption Spectrum (Film): 1780, 1765, 1680 cm$^{-1}$.

EXAMPLE 5

2,2,2-Trichloroethyl 2-oxo-3-(2-phenoxyacetamido)-4-(benzothiazol-2-yl)dithio-α-isopropenyl-1-azotidineacetate (0.63 g) was dissolved in dried methylene chloride (10 ml) under ice-cooling. To this solution was dropwise added a solution of thiocyanogen (0.6 m mole) in methylene chloride (5 ml). After the mixture was stirred for 24 hours at the same temperature, precipitates were filtered off. The filtrate was concentrated under reduced pressure and the residue was dissolved in ethyl acetate (10 ml). The ethyl acetate layer was washed with a saturated sodium bicarbonate aqueous solution and then with water and thereafter dried over magnesium sulfate. After the solvent was distilled off, the residue was crystallized by adding a small amount of ether. The crystals were filtered off and the filtrate was concentrated to give oily 2,2,2-trichloroethyl 2-thiocyanatomethyl-2-methyl-6-(2-phenoxyacetamido)penam-3-carboxylate (0.49 g).

Infrared Absorption Spectrum (Film): 1785, 1760, 1690 cm$^{-1}$.

EXAMPLE 6

2,2,2-Trichloroethyl 2-oxo-3-(2-phenylacetamido)-4-(benzothiazol-2-yl)dithio-α-isopropenyl-1-azetidineacetate (5.04 g) was dissolved in dried methylene chloride (20 ml). To this solution was dropwise added a solution of thiocyanogen (4.5 m mole) in methylene chloride for 5 minutes under ice-cooling. After stirring for 7 hours at the same temperature, precipitates were filtered off. The filtrate was washed with a saturated sodium bicarbonate aqueous solution and then with water and thereafter dried over magnesium sulfate. After distilling off the solvent under reduced pressure, the residue was crystallized by adding a small amount of ether to give 2,2,2-trichloroethyl 2-thiocyanatomethyl-2-methyl-6-(2-phenylacetamido)penam-3-carboxylate (3.58 g), mp 137° to 140° C.

EXAMPLE 7

2,2,2-Trichloroethyl 2-oxo-3-(2-phenylacetamido)-4-(benzothiazol-2-yl)dithio-α-isopropenyl-1-azetidineacetate (0.63 g) and potassium thiocyanate (150 mg) were dissolved in dried acetone (10 ml). To this solution was added p-toluenesulfonic acid monohydrate (0.19 g) and the mixture was stirred for 24 hours at room temperature. Precipitates were filtered off and the filtrate was concentrated under reduced pressure and then the residue was dissolved in ethyl acetate. The ethyl acetate layer was washed with a saturated sodium bicarbonate aqueous solution and then with water and thereafter dried over magnesium sulfate. The residue obtained by distilling off the solvent was crystallized by adding a small amount of ether to give 2,2,2-trichloroethyl 2-thiocyanatomethyl-2-methyl-6-(2-phenylacetamido)penam-3-carboxylate (330 mg).

EXAMPLE 8

2,2,2-Trichloroethyl 2-oxo-3-[3-(2-chlorophenyl)-5-methyl-isoxazol-4-carboxamido]-4-(benzothiazol-2-yl)dithio-α-isopropenyl-1-azetidineacetate (0.70 g) was dissolved in dried methylene chloride (10 ml) under ice-cooling. To this solution was dropwise added a solution of thiocyanogen (0.5 m mole) in methylene chloride (5 ml) and the mixture was stirred for 24 hours at the same temperature. Precipitates were filtered off and the filtrate was washed with a saturated sodium bicarbonate aqueous solution and then with water and thereafter dried. The solvent was distilled off and the residue was pulverized by adding petroleum ether (about 10 ml) to give 2,2,2-trichloroethyl 2-thiocyanatomethyl-2-methyl-6-[3-(2-chlorophenyl)-5-methylisoxazol-4-carboxamido]-penam-3-carboxylate (500 mg).

Infrared Absorption Spectrum (Nujol): 1785, 1770, 1670 cm$^{-1}$.

EXAMPLE 9

Acetic acid (5 ml) was added to a solution of 2,2,2-trichloroethyl 2-oxo-3-(2-phenylacetamido)-4-(benzothiazol-2-yl)dithio-α-isopropenyl-1-azetidineacetate (1.26 g) in ethyl acetate (15 ml) To this solution was added silver acetate (0.68 g) under stirring at room temperature and the mixture was stirred for 4 hours at the same temperature. After the reaction, precipitates were filtered off from the reaction mixture and the filtrate was washed with water, with 5% sodium bicarbonate aqueous solution and then filtered. The filtrate was washed with water, dried and the solvent was distilled off. The oily residue (0.87 g) was purified by thin layer chromatography and recrystallized from ether to give colorless needles of 2,2,2-trichloroethyl 2-acetoxymethyl-2-methyl-6-(2-phenylacetamido)penam-3-carboxylate, mp 116° to 118° C.

EXAMPLE 10

Methyl 2-oxo-3-(2-phenoxyacetamido)-4-anilinothio-α-isopropenyl-1-azetidineacetate (454 mg) was dissolved in methylene chloride (20 ml). To this solution were added methanol (5 ml) and then boron trifluoride etherate (0.124 g) under cooling at 0° C. The mixture was stirred for 3 hours at the same temperature and further stirred for 2 hours at 5° to 10° C. After the reaction, the reaction mixture was washed with 5% sodium bicarbonate aqueous solution and then with water, dried and the solvent was distilled off. The oily residue (25 g) was subjected to column chromatography on silica gel and eluted with chloroform. The eluate was separated into each 50 ml fraction and the seventh and eighth fractions were combined. The solvent was distilled off to give oily methyl 2-methoxymethyl-2-methyl-6-(2-phenoxyacetamido)penam-3-carboxylate.

Infrared Absorption Spectrum (CHCl$_3$): 3370, 1787, 1742, 1685 cm$^{-1}$.

The following compounds were obtained by using the same procedures as those of the Examples 1 to 10.

| | | | | |
|---|---|---|---|---|
| | | | $\begin{array}{c} \quad\quad S\quad CH_2-Y \\ R^1\diagup\!\!\!\diagdown\!\!\!\diagup\!\!\!\diagdown R^3 \\ \quad|\quad\quad|\quad\quad \\ O\!=\!\!\diagdown\!\!\!\diagup N\!\!\!\diagdown R^2 \end{array}$ | |

| No. | R¹ | R² | R³ | Y | Property of the product |
|---|---|---|---|---|---|
| 1 | C₆H₅—CH₂CONH— | —COOCH₂CCl₃ | —CH₃ | —N₃ | mp 105° to 106° C. |
| 2 | C₆H₅—CH₂CONH— | —COOCH₂CCl₃ | CH₃ | 5-methyl-1,3,4-thiadiazol-2-ylthio | Oil. Infrared Absorption Spectrum (CHCl₃) 3320, 1790, 1765, 1680 cm⁻¹. |
| 3 | C₆H₅—CH₂CONH— | —COOCH₂CCl₃ | —CH₃ | benzothiazol-2-ylthio | Oil. Infrared Absorption Spectrum (CHCl₃) 3400, 1790, 1765, 1680 cm⁻¹. |
| 4 | C₆H₅—CH₂CONH— | —COOCH₂CCl₃ | —CH₃ | 1-methyl-1H-tetrazol-5-ylthio | Oil. Infrared Absorption Spectrum (CHCl₃) 3300, 1790, 1765, 1680 cm⁻¹. |
| 5 | C₆H₅—CH₂CONH— | —COOCH₂CCl₃ | —CH₃ | —S—COCH₃ | Oil. Infrared Absorption Spectrum (CHCl₃) 3390, 1790, 1765, 1680-1690 cm⁻¹. |
| 6 | C₆H₅—CH₂CONH— | —COOCH₂CCl₃ | —CH₃ | —S—CS—N(piperidinyl) | Oil. Infrared Absorption Spectrum (CHCl₃) 3300, 1788, 1764, 1675 cm⁻¹. |
| 7 | C₆H₅—CH₂CONH— | —COOCH₂CCl₃ | —CH₃ | 1-methylimidazol-2-ylthio | Oil. Infrared Absorption Spectrum (CHCl₃) 3200, 1790, 1770, 1678 cm⁻¹ |
| 8 | C₆H₅—CH₂CONH— | —COOCH₂CCl₃ | —CH₃ | pyridin-4-ylthio | Oil. Infrared Absorption Spectrum (Film) 3250, 1780, 1765, 1665 cm⁻¹ |
| 9 | C₆H₅—OCH₂CONH— | —COOCH₃ | —CH₃ | 5-methyl-1,3,4-thiadiazol-2-ylthio | Infrared Absorption Spectrum (Film) 3300, 1785, 1745, 1690 cm⁻¹ |
| 10 | C₆H₅—CH(NH—COOCH(CH₃)—cyclopropyl)CONH— | —COOCH₂CCl₃ | —CH₃ | 1-methyl-1H-tetrazol-5-ylthio | Oil. Infrared Absorption Spectrum (Film) 3270, 1780, 1760, 1710, 1680 cm⁻¹ |
| 11 | C₆H₅—CH(NH—COOCH(CH₃)—cyclopropyl)CONH— | —COOCH₂CCl₃ | —CH₃ | 5-methyl-1,3,4-thiadiazol-2-ylthio | Oil. Infrared Absorption Spectrum (Film) 3270, 1760, 1710, 1680 cm⁻¹ |
| 12 | C₆H₅—CH₂CONH— | —COOCH₂CCl₃ | —CH₃ | —OCH₃ | Oil. Infrared Absorption Spectrum (CHCl₃) 3360, 1785, 1757, 1666 cm⁻¹ |
| 13 | C₆H₅—OCH₂CONH— | —COOCH₃ | —CH₃ | —NH—C₆H₅ | Oil. Infrared Absorption Spectrum (CHCl₃) 3410, 1785, 1748, 1690 cm⁻¹ |

|  | $R^1$ | $R^2$ | $R^3$ | Y | Property of the product |
|---|---|---|---|---|---|
| 14 | 1H-1,2,4-triazol-1-yl-CH₂CONH— | —COOCH₂CCl₃ | —CH₃ | —S-(1-methyl-1H-tetrazol-5-yl) | Amorphous<br>Infrared Absorption Spectrum (Nujol) 3220, 1780, 1760, 1700 cm⁻¹ |
| 15 | 3-(2-chlorophenyl)-5-methylisoxazol-4-yl-CONH— | —COOCH₂CCl₃ | —CH₃ | —S-(1-methyl-1H-tetrazol-5-yl) | Amorphous<br>Infrared Absorption Spectrum (Nujol) 3300, 1780, 1770, 1665 cm⁻¹ |
| 16 | H₂N— | —COOCH₂CCl₃ | —CH₃ | —SCN | toluenesulfonate<br>mp 182° to 185° C. (dec.) |
| 17 | C₆H₅CH₂CONH— | —COOH | —CH₃ | —SCOCH₃ | N,N'-dibenzylethylenediamine salt<br>mp 105° to 107° C. |
| 18 | C₆H₅CH₂CONH— | —COOH | —CH₃ | —S—CS—N(piperidyl) | N,N'-dibenzylethylenediamine salt<br>mp 100° C.(dec.) |
| 19 | C₆H₅CH₂CONH— | —COOH | —CH₃ | —NH—C₆H₅ | mp 120° C. |
| 20 | 3-(2-chlorophenyl)-5-methylisoxazol-4-yl-CONH— | —COOH | —CH₃ | —S-(1-methyl-1H-tetrazol-5-yl) | N,N'-dibenzylethylenediamine salt<br>mp 117° to 119° C.(dec.) |
| 21 | 1H-1,2,4-triazol-1-yl-CH₂CONH— | —COOH | —CH₃ | —S-(1-methyl-1H-tetrazol-5-yl) | mp 152° to 154° C. |
| 22 | C₆H₅CH₂CONH— | —COOH | —CH₃ | —S-(1-methyl-1H-tetrazol-5-yl) | N,N'-dibenzylethylenediamine salt<br>mp 150° to 152° C.(dec.) |
| 23 | C₆H₅CH₂CONH— | —COOH | —CH₃ | —S-(benzothiazol-2-yl) | Sodium salt<br>mp 200°C.(dec.) |
| 24 | C₆H₅CH₂CONH— | —COOH | —CH₃ | —S-(5-methyl-1,3,4-thiadiazol-2-yl) | Sodium salt<br>mp 185° to 186° C.(dec.) |

Reaction of:

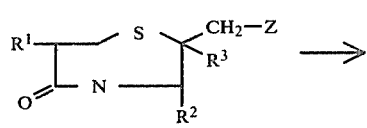 → 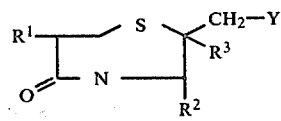

EXAMPLE 1

Potassium thiocyanate (1.17 g) was dissolved in a mixture of water (20 ml) and acetone (100 ml). To this solution was added 2,2,2-trichloroethyl 2-bromoethyl-2-methyl-6-(2-phenyl-acetamido)penam-3-carboxylate (5.45 g) at room temperature and the mixture was stirred for 5.5 hours at room temperature. After removing acetone under reduced pressure at room temperature, precipitates were collected by filtration, washed with ether and further washed with ethanol to give 2,2,2-trichloroethyl 2-thiocyanatomethyl-2-methyl-6-(2-phenylacetamido)penam-3-carboxylate (4.10 g). This substance was recrystallized from isopropylether containing 5% acetone to give pure compound, mp 133° to 135° C.

Analysis for $C_{19}H_{18}N_3O_4S_2Cl_3$: Calc'd. C43.64, H3.47, N8.04, S12.27, Cl20.34; Found: C43.84, H3.26, N7.99, S12.31, Cl20.31

EXAMPLE 2

A mixture of 2,2,2-trichloroethyl 2-bromomethyl-2-methyl-6-(2-phenylacetamido)penam-3-carboxylate (1.08 g), sodium azide (0.26 g), acetone (20 ml) and water (4 ml) was stirred for 4 hours at room temperature. After removing acetone under reduced pressure, the residue was extracted with ethyl acetate. The ethyl acetate layer was washed with water, with a saturated sodium bicarbonate queous solution and further with water and then dried over magnesium sulfate. The solvent was distilled off under reduced pressure and a small amount of ether was added to the residue. Precipitated crystals were filtered off and the solvent was distilled off from the filtrate. The crystalline residue was purified by column chromatography on silica gel using chloroform as developing solvent to give 2,2,2-trichloroethyl 2-azidomethyl-2-methyl-6-(2-phenylacetamido)penam-3-carboxylate (150 mg). This substance was crystallized by adding a small amount of a mixture of ether and petroleum ether and the crystals were recrystallized from ether to give pure compound, mp 105° to 106° C.

Analysis for $C_{18}H_{18}N_5O_4SCl_3$: Calc'd: C42.66, H3.58, N13.82, S6.33, Cl20.99. Found: C42.66, H3.40, N13.69, S6.79, Cl20.74.

EXAMPLE 3

5-Methyl-1,3,4-thiadiazole-2-thiol (0.16 g) was dissolved in a mixture of pH 6.5 phosphate buffer (5 ml) and acetone (10 ml). To this solution was added 2,2,2-trichloroethyl 2-bromomethyl-2-methyl-6-(2-phenylacetamido)penam-3-carboxylate (0.54 g) and the mixture was stirred for 3 hours at room temperature. The reaction mixture was concentrated under reduced pressure and acetone was distilled off and thereafter the residue was extracted with ethyl acetate. The ethyl acetate layer was washed with sodium bicarbonate aqueous solution and then with water and thereafter dried over magnesium sulfate. The solvent was distilled off and the residue was purified by column chromatography on silica gel using chloroform as developing solvent to give oily 2,2,2-trichloroethyl 2-(5-methyl-1,3,4-thiadiazol-2-yl)thiomethyl-2-methyl-6-(2-phenylacetamido)-penam-3-carboxylate (0.09 g) from the second and third fractions each of which was separated into about 30 ml.

Infrared Absorption Spectrum (CHCl$_3$): 3320, 1790, 1765, 1680 cm$^{-1}$.

EXAMPLE 4

5-Methyl-1,3,4-thiadiazole-2-thiol (0.20 g) and sodium bicarbonate (0.85 g) were dissolved in formamide (7 ml). To this solution was added 2,2,2-trichloroethyl 2-bromomethyl-2-methyl-6-(2-phenylacetamido)-penam-3-carboxylate (0.54 g), and the mixture was stirred for 5 hours at room temperature. To the reaction mixture was added water, and the mixture was extracted with ethyl acetate. The ethyl acetate layer was washed with a saturated sodium bicarbonate aqueous solution and then with water and thereafter dried over magnesium sulfate. The residue obtained by distilling off the solvent was purified by column chromatography on silica gel using chloroform as developing solvent to give oily 2,2,2-trichloroethyl 2-(5-methyl-1,3,4-thiadiazol-2-yl)thiomethyl-2-methyl-6-(2-phenylacetamido)penam-3-carboxylate (0.20 g) from the third fraction of fractions each of which was separated into about 30 ml.

EXAMPLE 5

Benzothiazole-2-thiol (0.20 g) was dissolved in a mixture of pH 6.7 phosphate buffer (15 ml) and dioxane (15 ml). To this solution was added 2,2,2-trichloroethyl 2-bromomethyl-2-methyl-6-(2-phenylacetamido)penam-3-carboxylate (0.54 g) and the mixture was stirred for 7 hours at room temperature. After the reaction was completed, dioxane was distilled off and the residue was extracted with ethyl acetate. The ethyl acetate layer was washed with a 2% potassium carbonate aqueous solution and then with water and thereafter dried over magnesium sulfate. The residue obtained by distilling off the solvent was purified by column chromatography on silica gel using chloroform as developing solvent to give oily 2,2,2-trichloroethyl 2-(benzothiazol-2-yl)thiomethyl-2-methyl-6-(2-phenylacetamido)penam-3-carboxylate (0.15 g) from the second fraction of fractions each of which was separated into 30 ml.

Infrared Absorption Spectrum (CHCl$_3$): 3400, 1790, 1765, 1680 cm$^{-1}$.

EXAMPLE 6

To a solution of 1-methyl-1H-tetrazole-5-thiol (0.23 g) in a mixture of pH 6.9 phosphate buffer (15 ml) and acetone (20 ml) was added 2,2,2-trichloroethyl 2-bromomethyl-2-methyl-6-(2-phenylacetamido)penam-3-carboxylate (0.54 g), and the mixture was stirred for 5 hours at room temperature. Acetone was distilled off from the reaction mixture. The aqueous layer was extracted with ethyl acetate and the extract was washed with sodium bicarbonate aqueous solution and then with a saturated sodium chloride aqueous solution. After the extract was dried over magnesium sulfate, the solvent was distilled off. The residue was purified by column chromatography on silica gel to give oily 2,2,2-trichloroethyl 2-(1-methyl-1H-tetrazol-5-yl)-thiomethyl-2-methyl-6-(2-phenylacetamido)penam-3-carboxylate (0.27 g).

Infrared Absorption Spectrum (CHCl$_3$): 3300, 1790, 1765, 1680 cm$^{-1}$.

EXAMPLE 7

Acetone (20 ml) and thioacetic acid (0.12 g) were added to pH 6.7 phosphate buffer (20 ml). To a mixture was added 2,2,2-trichloroethyl 2-bromomethyl-2-methyl-6-(2-phenylacetamido)penam-3-carboxylate (0.54 g) under stirring. After stirring for 5 hours at room temperature, the reaction mixture was post-treated in the similar manner as described in Example 6 to give oily 2,2,2-trichloroethyl 2-acetylthiomethyl-2-methyl-6-(2-phenylacetamido)penam-3-carboxylate (0.173 g).

Infrared Absorption Spectrum (CH Cl$_3$): 3390, 1790, 1965, 1690–1685 cm$^{-1}$.

EXAMPLE 8

Sodium piperidine-1-dithiocarboxylate (0.37 g) was dissolved in a mixture of pH 6.7 phosphate buffer (20 ml) and acetone (25 ml) and then to this solution was added 2,2,2-trichloroethyl 2-bromomethyl-2-methyl-6-(2-phenylacetamido)penam-3-carboxylate (0.54 g). After stirring for 3 hours at room temperature, the reaction mixture was post-treated in the similar manner as described in Example 6 to give oily 2,2,2-trichloroethyl 2-piperidinothiocarbonyl-thiomethyl-2-methyl-6-(2-phenylacetamido)penam-3-carboxylate (0.11 g).

Infrared Absorption Spectrum (CHCl$_3$): 3300, 1788, 1764, 1675 cm$^{-1}$.

EXAMPLE 9

Acetone (25 ml) was added to a solution of 1-methylimidazole-2-thiol (0.23 g) in pH 6.9 phosphate buffer (20 ml). To this solution was added 2,2,2-trichloroethyl 2-bromomethyl-2-methyl-6-(2-phenylacetamido)penam-3-carboxylate (0.54 g), and the mixture was stirred for 3 hours at room temperature.

The reaction mixture was post-treated in the similar manner as described in Example 6 to give oily 2,2,2-trichloroethyl 2-(1-methylimidazol-2-yl)thiomethyl-2-methyl-6-(2-phenylacetamido)penam-3-carboxylate (0.29 g).

Infrared Absorption Spectrum (CHCl$_3$): 3200, 1790, 1770, 1678 cm$^{-1}$.

EXAMPLE 10

Acetone (25 ml) was added to a solution of pyridine-4-thiol (0.22 g) in pH 6.8 phosphate buffer (20 ml). To this solution was added 2,2,2-trichloroethyl 2-bromomethyl-2-methyl-6-(2-phenylacetamido)penam-3-carboxylate (0.54 g), and the mixture was stirred for 3 hours at room temperature.

The reaction mixture was post-treated in the similar manner as described in Example 6 to give oily 2,2,2-trichloroethyl 2-(4-pyridyl)-thiomethyl-2-methyl-6-(2-phenylacetamido)penam-3-carboxylate (0.15 g).

Infrared Absorption Spectrum (Film): 3250, 1780, 1765, 1665 cm$^{-1}$.

EXAMPLE 11

5-Methyl-1,3,4-thiadiazole-2-thiol (0.4 g) was dissolved in a mixture of pH 7.3 phosphate buffer (20 ml) and acetone (20 ml). To this solution was added a solution of methyl 2-bromomethyl-2-methyl-6-(2-phenoxyacetamido)penam-3-carboxylate (0.80 g) in acetone (10 ml) and the mixture was stirred for 4 hours at room temperature. After the reaction was completed, acetone was distilled off from the reaction mixture and the residue was extracted with ethyl acetate. The extract was washed with sodium bicarbonate aqueous solution and then with water and thereafter dried over magnesium sulfate. The solvent was distilled off and the residue was subjected to column chromatography on silica gel (60 g) and eluted with chloroform. The eluate was separated into fractions of each about 30 ml to give methyl 2-(5-methyl-1,3,4-thiadiazol-2-yl)thiomethyl-2-methyl-6-(2-phenoxyacetamido)penam-3-carboxylate (0.28 g) from the fourth to seventh fractions.

Infrared Absorption Spectrum (Film): 3300, 1785, 1745, 1690 cm$^{-1}$.

EXAMPLE 12

Acetic acid (2 ml) was added to a solution of 2,2,2-trichloroethyl 2-bromomethyl-2-methyl-6-(2-phenylacetamido)penam-3-carboxylate (0.54 g) in methylene chloride (10 ml). And to this solution was added silver acetate (0.34 g) under stirring at room temperature and then the mixture was stirred for 2.5 hours. After the reaction was completed, the reaction mixture was filtered under reduced pressure and the filtrate was washed with 5% hydrochloric acid and then filtered again. The oily residue was crystallized by treating with ether and the crystals were collected by filtration and then dried to give colorless needles of 2,2,2-trichloroethyl 2-acetoxymethyl-2-methyl-6-(2-phenylacetamido)-penam-3-carboxylate (0.21 g), mp 116° to 118° C.

EXAMPLE 13

A solution of 2,2,2-trichloroethyl 2-bromomethyl-2-methyl-6-[N-(1-cyclopropylethoxy)carbonylphenyl-glycyl]-aminopenam-3-carboxylate (6.75 g) in acetone (50 ml) was added to a solution of 1-methyl-IH-tetrazole-5-thiol (2.6 g) in a mixture of phosphate buffer (200 ml) and acetone (200 ml), under cooling at 5° C., and the mixture was stirred for 5 hours at the same temperature. After the reaction was completed, acetone was distilled off from the reaction mixture under reduced pressure and the residue was extracted with ethyl acetate. The extract was washed with 5% sodium bicarbonate aqueous solution and then with water, dried. The solvent was distilled off. The oily residue was subjected to column chromatography on silica gel (180 g) and eluted with chloroform. The eluate was separated into fractions of each 50 ml and after collecting the fractions of the eleventh to sixteenth, the solvent was distilled off to give oily 2,2,2-trichloroethyl 2-(1-methyl-1H-tetrazol-5-yl)thiomethyl-2-methyl-6-[N-(1-cyclopropylethoxy)carbonylphenylglycyl]aminopenam-3-carboxylate (3.15 g).

Infrared Absorption Spectrum (Film): 3270, 1780, 1760, 1710, 1680 cm$^{-1}$.

EXAMPLE 14

By treating in the similar manner as described in Example 13 using 2,2,2-trichloroethyl 2-bromomethyl-2-methyl-6-[N-(1-cyclopropylethoxy)carbonylphenyl-glycyl]aminopenam-3-carboxylate (6.72 g), 5-methyl-1,3,4-thiadiazole-2-thiol (1.98 g), pH 6.8 phosphate buffer (200 ml) and acetone (250 ml), there was obtained oily 2,2,2-trichloroethyl 2-(5-methyl-1,3,4-thiadiazol-2-yl)-thiomethyl-2-methyl-6-[N-(1-cyclopropylethoxy)-carbonylphenylglycyl]aminopenam-3-carboxylate (1.16 g).

Infrared Absorption Spectrum (CHCl$_3$): 3420, 1790, 1770, 1708, 1687 cm$^{-1}$.

EXAMPLE 15

A solution of 2,2,2-trichloroethyl 2-bromomethyl-2-methyl-6-[N-(1-cyclopropylethoxy)carbonylphenyl-glycyl]aminopenam-3-carboxylate (3.6 g) in formamide (40 ml) was added to a solution of sodium bicarbonate (0.66 g) and 5-methyl-1,3,4-thiadiazole-2-thiol (1.1 g) in formamide (60 ml) under ice-cooling, after which the mixture was stirred for 4.5 hours at the same temperature. After the reaction was completed, the reaction mixture was poured into water and extracted with ethyl acetate. The extract was washed with 5% sodium bicarbonate aqueous solution and then with water, dried, after which the solvent was distilled off. The oily residue was subjected to column chromatography on silica gel (110 g) and eluted with chloroform. The eluate was separated into fractions of each 50 ml and after collecting the fractions of the fifteenth and sixteenth, the solvent was distilled off to give oily 2,2,2-trichloroethyl 2-(5-methyl-1,3,4-thiadiazol-2-yl)thiomethyl-2-methyl-6-[N-(1-cyclopropylethoxy)carbonylphenylglycyl]aminopenam-3-carboxylate (0.42 g).

EXAMPLE 16

2,2,2-Trichloroethyl 2-bromomethyl-2-methyl-6-(2-phenylacetamido)penam-3-carboxylate (1.10 g) dissolved in methylene chloride (15 ml). To this solution was added aniline (0.28 g) under cooling at $-10°$ C. and then silver fluoroborate (0.43 g), after which the mixture was stirred for 2 hours. After the reaction was completed, the reaction mixture was washed with a dilute phosphoric acid aqueous solution and then with water, dried over magnesium sulfate, after which the solvent was distilled off. The residue was subjected to column chromatography on silica gel (20 g) and eluted with chloroform. The eluate was separated into fractions of each about 20 ml. The second to seventh fractions were collected and the solvent was distilled off to give 2,2,2-trichloroethyl 2-anilinomethyl-2-methyl-6-(2-phenylacetamido)-penam-3-carboxylate (0.64 g), mp 148° to 149° C.

Infrared Absorption Spectrum (CHCl$_3$): 3400, 1780, 1765, 1680 cm$^{-1}$.

EXAMPLE 17

By treating in the similar manner as described in Example 16 using methyl 2-bromomethyl-2-methyl-6-(2-phenoxyacetamido)penam-3-carboxylate (0.88 g), aniline (0.28 g), silver fluoroborate (0.43 g) and methylene chloride (15 ml), there was obtained oily methyl 2-anilinomethyl-2-methyl-6-(2-phenoxyacetamido)-penam-3-carboxylate (0.41 g) from the fractions of the third to seventh.

Infrared Absorption Spectrum (CHCl$_3$): 3410, 1785, 1748, 1690 cm$^{-1}$.

EXAMPLE 18

2,2,2-Trichloroethyl 2-bromomethyl-2-methyl-6-(2-phenylacetamido)-penam-3-carboxylate (1.10 g) was dissolved in methylene chloride (12 ml) and to this solution was added methanol (3 ml). And to the solution was added silver fluoroborate (0.45 g) under stirring under cooling at $-10°$ C. and the mixture was stirred for 2 hours at the same temperature. After the reaction was completed, the reaction mixture was filtered and the filtrate was washed with sodium bicarbonate aqueous solution and then with water, dried over magnesium sulfate and thereafter concentrated. The residue was subjected to column chromatography on silica gel (25 g) and eluted with chloroform. The eluate was separated into fractions of about 20 ml and the first and second fractions were collected. After distilling off the solvent, the residue was dried to give oily 2,2,2-trichloroethyl-2-methoxymethyl-2-methyl-6-(2-phenylacetamido)penam-3-carboxylate.

Infrared Absorption Spectrum (CHCl$_3$): 3360, 1785, 1757, 1666 cm$^{-1}$.

EXAMPLE 19

By treating in the similar manner as described in Example 18 using methyl 2-bromomethyl-2-methyl-6-(2-phenoxyacetamido)penam-3-carboxylate instead of 2,2,2-trichloroethyl 2-bromomethyl-2-methyl-6-(2-phenylacetamido)penam-3-carboxylate, there was obtained oily methyl 2-methoxymethyl-2-methyl-6-(2-phenoxyacetamido)penam-3-carboxylate.

Infrared Absorption Spectrum (CHCl$_3$): 3370, 1787, 1742, 1685 cm$^{-1}$.

EXAMPLE 20

By treating in the similar manner as described in Example 11 using 2,2,2-trichloroethyl 2-bromomethyl-2-methyl-6-[3-(2-chlorophenyl)-5-methylisoxazole-4-carboxamido]penam-3-carboxylate and 1-methyl-IH-tetrazole-5-thiol in a mixture of pH 6.85 phosphate buffer and acetone, there was obtained amorphous 2,2,2-trichloroethyl 2-(1-methyl-IH-tetrazol-5-yl)thiomethyl-2-methyl-6-[3-(2-chlorophenyl)-5-methylisoxazole-4-carboxamido]penam-3-carboxylate.

Infrared Absorption Spectrum (Nujol): 3300, 1780, 1770, 1665 cm$^{-1}$.

EXAMPLE 21

By treating in the similar manner as described in Example 11 using 2,2,2-trichloroethyl 2-bromomethyl-2-methyl-6-[2-(1H-tetrazol-1-yl)-acetamido]penam-3-carboxylate and 1-methyl-1H-tetrazole-5-thiol in a mixture of pH 6.85 phosphate buffer and acetone, there was obtained amorphous 2,2,2-trichloroethyl 2-(1-methyl-1H-tetrazol-5-yl)thiomethyl-2-methyl-6-[2-(1H-tetrazol-1-yl)acetamido]penam-3-carboxylate.

Infrared Absorption Spectrum (Nujol): 3220, 1780, 1760, 1700 cm$^{-1}$.

The following compounds were obtained by using the same procedures as those of the Example 1 to 21.

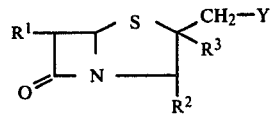

| No. | R$^1$ | R$^2$ | R$^3$ | Y | Property of the Products |
|-----|-------|-------|-------|---|--------------------------|
| 1 | ⌬—OCH$_2$CONH— | —COOCH$_2$CCl$_3$ | —CH$_3$ | —SCN | Oil<br>Infrared Absorption Spectrum (Film)<br>1785, 1760, 1690 cm$^{-1}$. |

-continued $$\begin{array}{c} R^1 \\ \diagdown \\ O \end{array} \begin{array}{c} S \\ \diagup \\ N \end{array} \begin{array}{c} CH_2-Y \\ R^3 \\ R^2 \end{array}$$

| No. | R¹ | R² | R³ | Y | Property of the Products |
|-----|-----|-----|-----|-----|-----|
| 2 | ![Ph-CH(CONH-)-NHOOCHCH₃ with cyclopropyl] C₆H₅-CH(CONH-)-NHOOCCH(CH₃)-(cyclopropyl CH₂-CH₂) | —COOCH₂CCl₃ | —CH₃ | —SCN | Oil<br>Infrared Absorption Spectrum (Film)<br>1780, 1765, 1680 cm⁻¹. |
| 3 | 2-Cl-C₆H₄-C(=NO-)-C(CH₃)=... -CONH- (isoxazole) | —COOCH₂CCl₃ | —CH₃ | —SCN | Powder<br>Infrared Absorption Spectrum (Nujol)<br>1785, 1770, 1670 cm⁻¹. |
| 4 | H₂N— | —COOCH₂CCl₃ | —CH₃ | —SCN | toluenesulfanate<br>mp 182° to 185° C.(dec.) |
| 5 | C₆H₅—CH₂CONH— | —COOH | —CH₃ | —SCOCH₃ | N,N'-dibenzylethylenediamine salt<br>mp 105° to 107° C. |
| 6 | C₆H₅—CH₂CONH— | —COOH | —CH₃ | —S—CS—N(piperidinyl) | N,N'-dibenzylethylenediamine salt<br>mp 100° C.(dec.) |
| 7 | C₆H₅—CH₂CONH— | —COOH | —CH₃ | —NH—C₆H₅ | mp 120° C. |
| 8 | 2-Cl-C₆H₄-C(=NO-)-C(CH₃)=...-CONH— (isoxazole) | —COOH | —CH₃ | —S—(1-methyl-tetrazol-5-yl) | N,N'-dibenzylethylenediamine salt<br>mp 117° to 119° C.(dec.) |
| 9 | (1H-tetrazol-1-yl)CH₂—CONH— | —COOH | —CH₃ | —S—(1-methyl-tetrazol-5-yl) | mp 152° to 154° C. |
| 10 | C₆H₅—CH₂CONH— | —COOH | —CH₃ | —S—(1-methyl-tetrazol-5-yl) | N,N'-dibenzylethylenediamine salt<br>mp 130° to 152° (dec.) |
| 11 | C₆H₅—CH₂CONH— | —COOH | —CH₃ | —S—(benzothiazol-2-yl) | Sodium salt<br>mp 200° C. (dec.) |
| 12 | C₆H₅—CH₂CONH— | —COOH | —CH₃ | —S—(5-methyl-1,3,4-thiadiazol-2-yl) | Sodium salt<br>mp 185° to 186° C. (dec.) |

Reaction of:

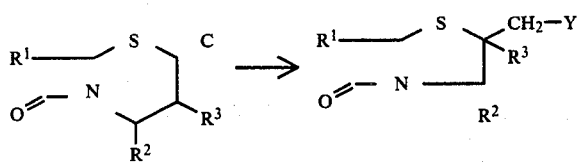

EXAMPLE 1

2,2,2-Trichloroethyl 3-bromo-3-methyl-7-(2-phenylacetamido)cepham-4-carboxylate (1.10 g) was dissolved in methylene chloride (15 ml) and to this solution was added aniline (0.28 g). And to the solution was added silver fluoroborate (0.5 g) under stirring under ice-cooling and the mixture was stirred for 4 hours at the same temperature. After the reaction was completed, the reaction mixture was filtered. The filtrate was washed with a dilute aqueour solution of phosphoric acid and then with water, dried over magnesium sulfate and concentrated. The residue was subjected to column chromatography on silica gel (25 g) and eluted with chloroform. The eluate was separated into fractions of each about 20 ml and the second to eighth fractions were collected and then the solvent was distilled off to give 2,2,2-trichloroethyl 2-anilinomethyl-2-methyl-6-(2-phenylacetamido)penam-3-carboxylate (0.54 g), mp 148° to 149° C.

Infrared Absorption Spectrum (CHCl₃): 3400, 1780, 1765, 1680 cm⁻¹.

The following compounds were obtained by using the same procedure as that of the Example 1.

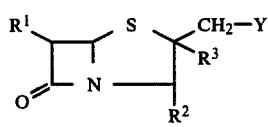

| No. | $R^1$ | $R^2$ | $R^3$ | Y | Property of the product |
|---|---|---|---|---|---|
| 1 | ⌬—CH₂CONH— | —COOCH₂CCl₃ | —CH₃ | —N₃ | mp 105 to 106° C. |
| 2 | ⌬—CH₂CONH— | —COOCH₂CCl₃ | —CH₃ | —S—(thiadiazolyl)—CH₃ | Oil<br>Infrared Absorption Spectrum (CHCl₃)<br>3320, 1790, 1765, 1680 cm⁻¹ |
| 3 | ⌬—CH₂CONH— | —COOCH₂CCl₃ | —CH₃ | —S—(benzothiazolyl) | Oil<br>Infrared Absorption Spectrum (CHCl₃)<br>3400, 1790, 1765, 1680 cm⁻¹ |
| 4 | ⌬—CH₂CONH— | —COOCH₂CCl₃ | —CH₃ | —S—(1-methyltetrazolyl) | Oil<br>Infrared Absorption Spectrum (CHCl₃)<br>3300, 1790, 1765, 1680 cm⁻¹ |
| 5 | ⌬—CH₂CONH— | —COOCH₂CCl₃ | —CH₃ | —S—COCH₃ | Oil<br>Infrared Absorption Spectrum (CHCl₃)<br>3390, 1790, 1765, 1690–1680 cm⁻¹ |
| 6 | ⌬—CH₂CONH— | —COOCH₂CCl₃ | —CH₃ | —S—CS—N(piperidino) | Oil<br>Infrared Absorption Spectrum (CHCl₃)<br>3300, 1788, 1764, 1675 cm⁻¹ |
| 7 | ⌬—CH₂CONH— | —COOCH₂CCl₃ | —CH₃ | —S—(1-methylimidazolyl) | Oil<br>Infrared Absorption Spectrum (CHCl₃)<br>3200, 1790, 1770, 1678 cm⁻¹ |
| 8 | ⌬—CH₂CONH— | —COOCH₂CCl₃ | —CH₃ | —S—(pyridyl) | Oil<br>Infrared Absorption Spectrum (Film)<br>3250, 1780, 1765, 1665 cm⁻¹ |
| 9 | ⌬—OCH₂CONH— | —COOCH₃ | —CH₃ | —S—(thiadiazolyl)—CH₃ | Infrared Absorption Spectrum (Film)<br>3300, 1785, 1745, 1690 cm⁻¹ |

-continued $$\begin{array}{c} R^1 \phantom{xxx} S \phantom{xx} CH_2-Y \\ \diagup\phantom{xx}\diagdown\phantom{xx}\diagup R^3 \\ O=\phantom{x}N\phantom{xx}R^2 \end{array}$$

| No. | R¹ | R² | R³ | Y | Property of the product |
|---|---|---|---|---|---|
| 10 | Ph-CH(NH-COOCH(CH₃)-CH(CH₂-CH₂ cyclopropyl))-CONH— | —COOCH₂CCl₃ | —CH₃ | -S-C(=N-N(CH₃)-N=)- (thiadiazole-methyl) | Oil<br>Infrared Absorption Spectrum (Film)<br>3270, 1780, 1760, 1710, 1680 cm⁻¹ |
| 11 | Ph-CH(NH-COOCH(CH₃)-CH(CH₂-CH₂ cyclopropyl))-CONH— | —COOCH₂CCl₃ | —CH₃ | -S-(1,3,4-thiadiazol-2-yl)-CH₃ | Oil<br>Infrared Absorption Spectrum (Film)<br>3270, 1760, 1710, 1680 cm⁻¹ |
| 12 | Ph-CH₂CONH— | —COOCH₂CCl₃ | —CH₃ | —OCH₃ | Oil<br>Infrared Absorption Spectrum (CHCl₃)<br>3360, 1785, 1757, 1666 cm⁻¹ |
| 13 | Ph-OCH₂CONH— | —COOCH₃ | —CH₃ | —NH-Ph | Oil<br>Infrared Absorption Spectrum (CHCl₃)<br>3410, 1785, 1748, 1690 cm⁻¹ |
| 14 | (tetrazol-1-yl)CH₂CONH— | —COOCH₂CCl₃ | —CH₃ | -S-(1-methyl-tetrazol-5-yl) | Amorphous<br>Infrared Absorption Spectrum (Nujol)<br>3220, 1780, 1760, 1700 cm⁻¹ |
| 15 | (2-chlorophenyl)-5-methyl-isoxazol-4-yl-CONH— | —COOCH₂CCl₃ | —CH₃ | -S-(1-methyl-tetrazol-5-yl) | Amorphous<br>Infrared Absorption Spectrum (Nujol)<br>3300, 1780, 1770, 1665 cm⁻¹ |
| 16 | Ph-OCH₂CONH— | —COOCH₃ | —CH₃ | —OCH₃ | Oil<br>Infrared Absorption Spectrum (CHCl₃)<br>3370, 1787, 1742, 1685 cm⁻¹ |
| 17 | Ph-OCH₂CONH— | —COOCH₂CCl₃ | —CH₃ | —SCN | Oil<br>Infrared Absorption Spectrum (Film)<br>1785, 1760, 1690 cm⁻¹ |
| 18 | Ph-CH(NHCOCH(CH₃)-CH(CH₂-CH₃ cyclopropyl))-CONH— | —COOCH₂CCl₃ | —CH₃ | —SCN | Oil<br>Infrared Absorption Spectrum (Film)<br>1780, 1765, 1680 cm⁻¹ |
| 19 | (2-chlorophenyl)-5-methyl-isoxazol-4-yl-CONH— | —COOCH₂CCl₃ | —CH₃ | —SCN | Powder<br>Infrared Absorption Spectrum (Nujol)<br>1785, 1770, 1670 cm⁻¹ |
| 20 | Ph-CH₂CONH— | —COOCH₂CCl₃ | —CH₃ | —SCN | mp 137 to 140° C. |
| 21 | H₂N— | —COOCH₂CCl₃ | —CH₃ | —SCN | toluenesulfonate<br>mp 182 to 185° C. (dec.) |

-continued

Structure header: R¹-substituted penam with CH₂-Y, R³ at C-2 and R² (-COOH) at C-3:

$$\text{R}^1-\underset{O}{\overset{}{\square}}-N-\text{penam}-CH_2-Y,\ R^3,\ R^2$$

| No. | R¹ | R² | R³ | Y | Property of the product |
|---|---|---|---|---|---|
| 22 | C₆H₅-CH₂CONH- | -COOH | -CH₃ | -SCOCH₃ | N,N'-dibenzylethylenediamine salt mp 105 to 107° C. |
| 23 | C₆H₅-CH₂CONH- | -COOH | -CH₃ | -S-CS-N(piperidine) | N,N'dibenzylethylenediamine salt mp 100° C. (dec.) |
| 24 | C₆H₅-CH₂CONH- | -COOH | -CH₃ | -NH-C₆H₅ | mp 120° C. |
| 25 | 2-Cl-C₆H₄-C(=NOCH₃)-CONH- | -COOH | -CH₃ | -S-(1-methyltetrazol-5-yl) | N,N'-dibenzylethylenediamine salt m 117 to 119° C. (dec.) |
| 26 | (tetrazol-1-yl)CH₂-CONH- | -COOH | -CH₃ | -S-(1-methyltetrazol-5-yl) | mp 152 to 154° C. |
| 27 | C₆H₅-CH₂CONH- | -COOH | -CH₃ | -S-(1-methyltetrazol-5-yl) | N,N'-dibenzylethylenediamine salt mp 150 to 152° C. (dec.) |
| 28 | C₆H₅-CH₂CONH- | -COOH | -CH₃ | -S-(benzothiazol-2-yl) | Sodium salt mp 200° C. (dec.) |
| 29 | C₆H₅-CH₂CONH- | -COOH | -CH₃ | -S-(5-methyl-1,3,4-thiadiazol-2-yl) | Sodium salt mp 185 to 186° C. (dec.) |

Reaction of:

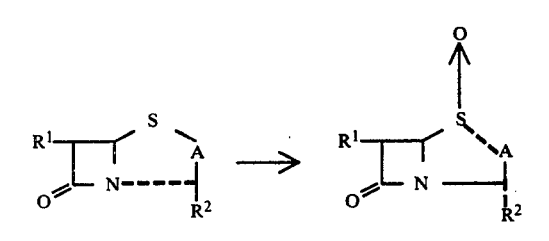

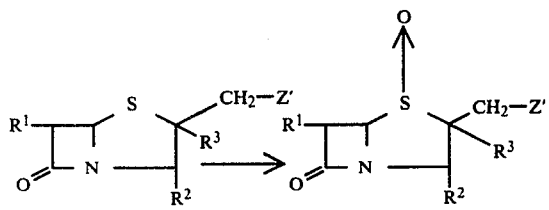

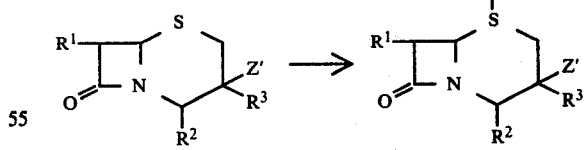

EXAMPLE 1

A solution of m-chloroperbenzoic acid (1.39 g) in chloroform (15 ml) was added to a solution of 2,2,2-trichloroethyl 2-bromomethyl-2-methyl-6-(2-phenylacetamido)penam-3-carboxylate (3.74 g) in chloroform (35 ml) under ice-cooling. The mixture was stirred under ice-cooling for 1 hour, and precipitates were filtered off. The filtrate was washed with a saturated sodium bicarbonate aqueous solution and water in turn and dried over magnesium sulfate. After the solvent was removed under reduced pressure, the residue was crystallized by adding a little of ether. The Crystals were filtered to give colorless crystals of 2,2,2-trichloroethyl 2-bromomethyl-2-methyl-6-(2-phenylacetamido)penam-3-carboxylate-1-β-oxide (3.15 g), mp 114°–115° C. (dec.).

Analysis $C_{18}H_{18}O_5N_2SCl_3Br$: Calcd. C 38.55, H 3.24, N 4.99; Found C 38.40, H 3.12, N 4.68

EXAMPLE 2

2,2,2-trichloroethyl 2-bromomethyl-2-methyl-6-(2-phenylacetamido)penam-3-carboxylate (540 mg) was suspended in a mixed solution of pyridine (10 ml) and water (1 ml) at $-35°$– $-40°$ C. To the suspension was dropwise added isocyanuroyl chloride (110 mg). The mixture was stirred for an hour and twenty minutes and then the mixture was poured into a mixed solution of 20% aqueous phosphoric acid (50 ml) and ethyl acetate (20 ml) under ice-cooling. The ethyl acetate fraction was separated. After the water layer was extracted with ethyl acetate, the ethyl acetate extract was combined with the above-obtained ethyl acetate layer. The extract was washed with 5% phosphoric acid, water, saturated sodium bicarbonate aqueous solution and water in turn, and then dried over magnesium sulfate. After the solvent was removed, the residue was subjected to column chromatography on silica gel with chloroform. The 3rd fraction was concentrated to give 2,2,2-trichloroethyl 2-bromomethyl-2-methyl-6-(2-phenylacetamido)penam-3-carboxylate-1-β-oxide (130 mg). The 5th fraction was concentrated to give 2,2,2-trichloroethyl 2-bromomethyl-2-methyl-6-(2-phenylacetamido)-penam-3-carboxylate-1-α-oxide (170 mg).

Infrared Absorption Spectrum (CHCl$_3$) of the α-oxide compound: 3420, 1795, 1770, 1665 cm$^{-1}$.

EXAMPLE 3 m-Chloroperbenzoic acid (210 mg) was dropwise added to a solution of 2,2,2-trichloroethyl 2-thiocyanatomethyl-2-methyl-6-(2-phenylacetamido)penam-3-carboxylate (522 mg) in chloroform (10 ml) under ice-cooling. The mixture was stirred under ice-cooling for 1 hour and the solid was filtered off. The filtrate was washed with a saturated sodium bicarbonate aqueous solution and water, in turn, and then dried over magnesium sulfate. The solvent was removed to give colorless powder of 2,2,2-trichloroethyl 2-thiocyanatomethyl-2-methyl-6-(2-phenylacetamido)penam-3-carboxylate-1-β-oxide (540 mg).

Infrared Absorption Spectrum (Nujol): 3330, 2130, 1797, 1778 (sh.), 1677 cm$^{-1}$.

EXAMPLE 4

2,2,2-Trichloroethyl 2-thiocyanatomethyl-2-methyl-6-(2-phenylacetamido)penam-3-carboxylate (522 mg) was suspended in a mixed solution of pyridine (10 ml) and water (1 ml) at $-35°$– $-40°$ C. To the suspension was dropwise added isocyanuroyl chloride (110 mg) at $-35°$– $-40°$ C. The mixture was stirred at $-35°$– $-40°$ C. for 1 hour, and then poured into a mixed solution of ice-cooled 20% phosphoric acid (50 ml) and ethyl acetate (20 ml), and then the ethyl acetate layer was separated. After the water layer was extracted with ethyl acetate, the extract was combined with the above-obtained ethyl acetate layer. The extract was washed with 5% phosphoric acid, water, saturated sodium bicarbonate aqueous solution and water, in turn, and dried over magnesium sulfate. After the solvent was distilled off, the residue was purified by column chromatography on silica gel with chloroform to give 2,2,2-trichloroethyl 2-thiocyanatomethyl-2-methyl-6-(2-phenylacetamido)penam-3-carboxylate-1-β-oxide (140 mg).

EXAMPLE 5

2,2,2-trichloroethyl 2-thiocyanatomethyl-2-methyl-6-(2-phenylacetamido)penam-3-carboxylate (522 mg) was suspended in a mixed solution of pyridine (12 ml) and water (12 ml) at $-25°$– $-35°$ C. To the suspension was added phenyliododichloride (550 mg). And the mixture was stirred at $-25°$– $-35°$ C. for 3 hours, phenyliododichloride (550 mg) was further added to the mixture. After stirring for 1 hour, phenyliododichloride (550 mg) was added to the mixture again. The reaction mixture was stirred for additional one hour, poured into a mixed solution of 20% phosphoric acid (50 ml) and ethyl acetate (20 ml), and then the ethyl acetate layer was separated. The aqueous layer was extracted with ethyl acetate, which was combined with the above-obtained ethyl acetate layer. The combined ethyl acetate layer was washed with 9% phosphoric acid, water, saturated sodium bicarbonate aqueous solution and water, in turn, and then dried over magnesium sulfate. After the solvent was removed under reduced pressure, the residue was subjected to column chromatography on silica gel with a mixed solution of benzene (2 parts) and ethyl acetate (1 part). The 3rd to 7th fractions were concentrated to give 2,2,2-trichloroethyl 2-thiocyanatomethyl-2-methyl-6-(2-phenylacetamido)penam-3-carboxylate-1-β-oxide (250 mg).

EXAMPLE 6

A solution of m-chloroperbenzoic acid (2.03 g) in chloroform (30 ml) was added dropwise to a solution of 2,2,2-trichloroethyl-2-chloromethyl-2-methyl-6-(2-phenylacetamido)penam-3-carboxylate (5.0 g) in chloroform (40 ml) at $-10°$– $-5°$ C. under stirring, and then the mixture was stirred at $-10°$– $-5°$ C. for 1 hour. After the solid was filtered off, the filtrate was washed with a saturated sodium becarbonate aqueous solution and water, in turn, and then dried over magnesium sulfate. After removal of solvent, the residue was crystallized by adding ethanol. The crystal was filtered and recrystallized from ethanol to give 2,2,2-trichloroethyl 2-chloromethyl-2-methyl-6-(2-phenylacetamido)penam-3-carboxylate-1-oxide (4.10 g), mp 130°–131° C.

Analysis $C_{18}H_{18}O_5N_2SCl_4$: Calcd. C 41.87, H 3.51, M 5.43, S 6.21. Found C 41.80, H 3.45, N 5.50, S 6.44.

EXAMPLE 7

Sodium tungstate (0.02 g) was added to a solution of 2-bromomethyl-2-methyl-6-(2-phenoxyacetamido)penam-3-carboxylic acid (3.1 g) in acetic acid (8 ml) at 7°–10° C. under stirring and then to the mixture was added 30% aqueous hydrogen peroxide (1.2 ml). The mixture was stirred at 7°–10° C. for 1 hour. After the reaction, ice-water (50 ml) was added to the reaction mixture and then extracted with ethyl acetate. The extract was washed with water and back-extracted with 5% sodium bicarbonate aqueous solution. The aqueous layer was washed with ethyl acetate twice, acidified with 5% hydrochloric acid to pH2 and then extracted with ethyl acetate. The extract was washed with water, dried and concentrated to give powder of 2-bromomethyl-2-methyl-6-(2-phenoxyacetamido)penam-3-carboxylic acid-1-oxide (2 g).

Infrared Absorption Spectrum (CHCl₃): 3350, 1795, 1740, 1688 cm⁻¹.

EXAMPLE 8

A solution of m-chloroperbenzoic acid (0.445 g) in chloroform (5 ml) was added to a solution of 2,2,2-trichloroethyl 3-bromo-3-methyl-7-(2-phenylacetamido)-cepham-4-carboxylate (1.21 g) under stirring at −5° to −10° C., and the mixture was stirred for an hour at the same temperature. After the reaction, the reaction mixture was washed with 5% sodium bicarbonate aqueous solution and with water in turn and then dried. After the solvent was distilled off, the residue was crystallized by adding ether. Thus obtained crystals were recrystallized from ethanol to give 2,2,2-trichloroethyl 3-bromo-3-methyl-7-(2-phenylacetamido)cepham-4-carboxylate-1-oxide (1.10 g), mp 159° to 161° C.

Reaction of:

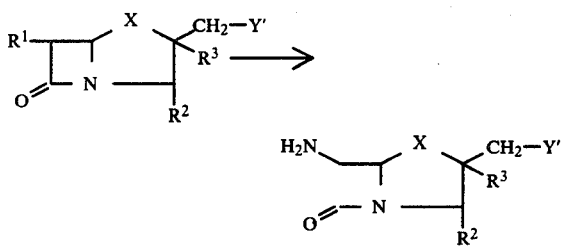

EXAMPLE 3

2,2,2-Trichloroethyl 2-bromomethyl-2-methyl-6-(2-phenylacetamido)-penam-3-carboxylate-1-oxide (1.12 g) was dissolved in dried methylene chloride (10 ml). To this solution were added dimethyl aniline (0.36 g) under cooling at −15° C. and then phosphorus pentachloride (0.6 g), and the mixture was stirred for 3 hours. To the solution was added anhydrous methanol (0.7 g) under cooling at −40° C. and the solution was stirred for 2 hours and further stirred for 1 hour at −15° C. After the reaction, precipitated crystals were collected by filtration, washed with a small amount of methylene chloride and then dried to give 2,2,2-trichloroethyl 2-bromomethyl-2-methyl-6-aminopenam-3-carboxylate-1-oxide hydrochloride (0.70 g), mp 147° to 154° C. (dec.).

Infrared Absorption Spectrum (Nujol): 1820, 1800, 1760 cm⁻¹

EXAMPLE 2

2,2,2-Trichloroethyl 2-bromomethyl-2-methyl-6-(2-phenylacetamido)penam-3-carboxylate (10.8 g) was dissolved in dried methylene chloride (300 ml). To this solution were added under cooling at −35° C. dried dimethylaniline (3.6 g) and then phosphorus pentachloride (6.4 g) and the mixture was stirred for 2.5 hours at the same temperature. To the solution was added dropwise anhydrous methanol (6.4 g) at the same temperature and the mixture was stirred for 1 hour at −15° C. Water (6.5 ml) as added to the solution and the solution as vigorously stirred for 30 minutes. After the reaction, precipitates were collected by filtration, washed with methylene chloride and further with ether and then dried to give powdery 2,2,2-trichloroethyl 2-bromomethyl-2-methyl-6-aminopenam-3-carboxylate hydrochloride (7.8 g).

Infrared Absorption Spectrum (Nujol): 3350—3400, 1790, 1770 cm⁻¹.

EXAMPLE 3

2,2,2-Trichloroethyl 2-thioyanatomethyl-2-methyl-6-(2-phenylacetamido)-penam-3-carboxylate (0.53 g) was dissolved in dried methylene chloride (10 ml). To this solution were added under cooling at −20° to −30° C. dimethylaniline (0.43 g) and then phosphorus pentachloride (0.23 g) and the mixture was stirred for 1.5 hours. Further, to the solution was added dropwise anhydrous methanol (0.34 g) and the solution was stirred for 5 hours. Water (7 ml) was added to the solution at 0° C. and the mixture was stirred for 10 minutes. Aqueous layer was separated from the mixture. The aqueous layer was adjusted to pH9 by adding 1N-sodium hydroxide aqueous solution and extracted with ethyl acetate (10 ml). The extract was dried over magnesium sulfate and the solvent was distilled off. The residue was dissolved in a small amount of ethyl acetate and to the solution were added toluene-sulfonic acid monohydrate (0.1 g) and ethyl acetate (5 ml). The mixture was cooled and precipitated crystals were collected by filtration to give 2,2,2-trichloroethyl 2-thiocyanatomethyl-2-methyl-6-aminopenam-3-carboxylate toluenesulfonae (0.06 g), mp 182° to 185° C. (dec.).

Infraed Absorption Spectrum (Najol): 2150, 1795, 1750 cm⁻¹.

Reaction of:

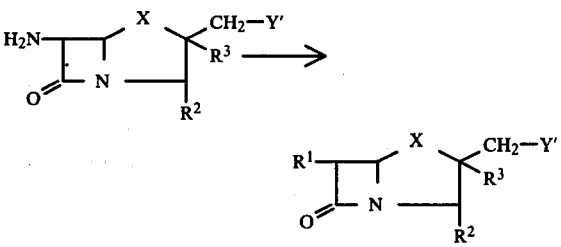

EXAMPLE 1

To a sodium of ethyl chlorocarbonate (1.94 g) in dried methylene chloride (120 ml) was added dropwise under cooling −5° C. a solution of N-(1-cyclopropyle-thoxy)carbonylphenylglycine (4.74 g) and triethylamine (1.83 g) in dried methylene chloride (50 ml). The solution containing a mixed anhydride of N-(1-cyclopropylethoxy)carbonylphenylglycine and ethyl chlorocarbonate prepared by stirring the above mixture for 1 hour at the same temperature was cooled at −30° to −35° C. To this solution were added dropwise a solution of 2,2,2-trichloroethyl 2-bromomethyl-2-methyl-6-aminopenam-3-carboxylate hydrochloride (6.95 g) and triethylamine (3.0 g) in dried methylene chloride (100 ml), and the mixture was stirred for 3 hours. After the reaction was completed, the reaction mixture was washed with 5% hydrochloric acid, water, 5% sodium bicarbonate aqueous solution and water in turn and then dried. The solvent was distilled off to give amorphous, 2,2,2-trichloroethyl 2-bromomethyl-2-methyl-6-[N-(1-cyclopropylethoxy)-phenylglycyl]aminopenam-3-carboxylate (9.7 g).

Infrared Absorption Spectrum (CHCl₃): 3410, 1785, 1765, 1690 cm⁻¹.

EXAMPLE 2

To a solution of pivaloyl chloride (1.4 g) in dried methylene chloride (100 ml) was added dropwise under cooling at −5° C. a solution of 1H-tetrazol-1-acetic acid (1.81 g) and triethylamine (1.4 g) in dried methylene chloride (30 ml), and the mixture was stirred for 2 hours at the same temperature. The solution containing a mixed anhydride of 1H-tetrazole-1-acetic acid and pivalic acid prepared above was cooled at −35° C. and to the solution were added dropwise a solution of 2,2,2-trichloroethyl 2-bromomethyl-2-methyl-6-aminopenam-3-carboxylate hydrochloride (4.0 g) and triethlamino (2.0 g) in dried methylene chloride (80 ml), after which the mixture was stirred for 4 hours at the same temperature. After the reaction was completed, the reaction mixture was post-treated in the similar manner as described in Example 1 to give oily 2,2,2-trichloroethyl 2-bromomethyl-2-methyl-6-[2-(1H-tetrazol-1-yl)acetamido]penam-3-carbodylate (3.85 g).

Infrared Absorption Spectrum (Film): 3250, 1783, 1765, 1685 cm$^{-1}$.

EXAMPLE 3

A solution of 2,2,2-trichloroethyl 2-bromomethyl-2-methyl-6-aminopenam-3-carboxylate hydrochloride (6.95 g) and triethylamine (3.0 g) in dried methylene chloride (100 ml) was cooled at −25° C. To this solution was added dropwise a solution of 3-(2-chlorophenyl)-5-methylisoxazole-4-carbonyl chrolide (4.5 g) in dried methylene chloride (30 ml), and the mixture was stirred for 3 hours at the same temperature. After the reaction was completed, the reaction mixture was post-treated in the similar manner as described in Example 1 to give oily 2,2,2-trichloroethyl 2-bromomethyl-2-methyl-6-[3-(2-chlorophenyl)-5-methylisoxazole-4-carboxamido]penam-3-carboxylate (6.75 g).

Infrared Absorption Spectrum (Film): 3370, 1790, 1765, 1670 cm$^{-1}$.

The following compounds were obtained by using the same procedures as those of the Examples 1 to 3.

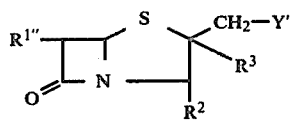

| No. | R$^{1''}$ | R$^2$ | R$^3$ | Y' | X | Property of the product |
|---|---|---|---|---|---|---|
| 1 | ⟨phenyl⟩—CH$_2$CONH— | —COOCH$_2$CCl$_3$ | —CH$_3$ | —N$_3$ | —S— | mp. 105° to 106° C. |
| 2 | ⟨phenyl⟩—CH$_2$CONH— | —COOCH$_2$CCl$_3$ | —CH$_3$ | —S—(thiadiazole)—CH$_3$ | —S— | Oil Infrared Absorption Spectrum(CHCl$_3$) 3320, 1790, 1765, 1680 cm$^{-1}$ |
| 3 | ⟨phenyl⟩—CH$_2$CONH— | —COOCH$_2$CCl$_3$ | —CH$_3$ | —S—(benzothiazole) | —S— | Oil Infrared Absorption Spectrum(CHCl$_3$) 3400, 1790, 1765, 1680 cm$^{-1}$ |
| 4 | ⟨phenyl⟩—CH$_2$CONH— | —COOCH$_2$CCl$_3$ | —CH$_3$ | —S—(N-methyltetrazole) | —S— | Oil Infrared Absorption Spectrum(CHCl$_3$) 3300, 1790, 1765, 1680 cm$^{-1}$ |
| 5 | ⟨phenyl⟩—CH$_2$CONH— | —COOCH$_2$CCl$_3$ | —CH$_3$ | —S—COCH$_3$ | —S— | Oil Infrared Absorption Spectrum(CHCl$_3$) 3390, 1790, 1765, 1600 to 1680 cm$^{-1}$ |
| 6 | ⟨phenyl⟩—CH$_2$CONH— | —COOCH$_2$CCl$_3$ | —CH$_3$ | —S—CS—N(piperidine) | —S— | Oil Infrared Absorption Spectrum(CHCl$_3$) 3300, 1788, 1764, 1675 cm$^{-1}$ |
| 7 | ⟨phenyl⟩—CH$_2$CONH— | —COOCH$_2$CCl$_3$ | —CH$_3$ | —S—(N-methylimidazole) | —S— | Oil Infrared Absorption Spectrum(CHCl$_3$) 3200, 1790, 1770, 1678 cm$^{-1}$ |
| 8 | ⟨phenyl⟩—CH$_2$CONH— | —COOCH$_2$CCl$_3$ | —CH$_3$ | —S—(pyridine) | —S— | Oil Infrared Absorption Spectrum(Film) 3250, 1780, 1765, 1665 cm$^{-1}$ |

-continued

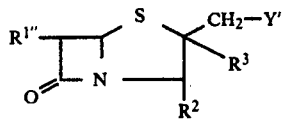

| No. | R¹″ | R² | R³ | Y′ | X | Property of the product |
|---|---|---|---|---|---|---|
| 9 | Ph-OCH₂CONH- | -COOCH₃ | -CH₃ | -S-(thiadiazole-CH₃) | -S- | Oil<br>Infrared Absorption Spectrum(Film) 3300, 1785, 1745, 1690 cm⁻¹ |
| 10 | Ph-CH(CONH-)(NH-COOCHCH₃-cyclopropyl) | -COOCH₂CCl₃ | -CH₃ | -S-(tetrazole-N-CH₃) | -S- | Oil<br>Infrared Absorption Spectrum(Film) 3270, 1780, 1760, 1710, 1680 Cm⁻¹ |
| 11 | Ph-CH(CONH-)(NH-COOCHCH₃-cyclopropyl) | -COOCH₂CCl₃ | -CH₃ | -S-(thiadiazole-CH₃) | -S- | Oil<br>Infrared Absorption Spectrum(Film) 3270, 1760, 1710, 1680 cm⁻¹ |
| 12 | Ph-CH₂CONH- | -COOCH₂CCl₃ | -CH₃ | -OCH₃ | -S- | Oil<br>Infrared Absorption Spectrum(CHCl₃) 3360, 1785, 1757, 1666 cm⁻¹ |
| 13 | Ph-OCH₂CONH- | -COOCH₃ | -CH₃ | -NH-Ph | -S- | Oil<br>Infrared Absorption Spectrum(CHCl₃) 3410, 1785, 1748, 1690 cm⁻¹ |
| 14 | (triazole-N-CH₂CONH-) | -COOCH₂CCl₃ | -CH₃ | -S-(tetrazole-N-CH₃) | -S- | Amorphous |
| 15 | (2-Cl-phenyl-5-methyl-isoxazole-4-CONH-) | -COOCH₂CCl₃ | -CH₃ | -S-(tetrazole-N-CH₃) | -S- | Amorphous<br>Infrared Absorption Spectrum(Nujol) 3300, 1780, 1770, 1665 cm⁻¹ |
| 16 | Ph-OCH₂CONH- | -COOCH₃ | -CH₃ | -OCH₃ | -S- | Oil<br>Infrared Absorption Spectrum(CHCl₃) 3370, 1787, 1742, 1685 cm⁻¹ |
| 17 | Ph-CH₂CONH- | -COOCH₂CCl₃ | -CH₃ | -NH-Ph | -S- | mp 148° to 149° C. |
| 18 | Ph-OCH₂CONH- | -COOCH₂CCl₃ | -CH₃ | -SCH | -S- | Oil<br>Infrared Absorption Spectrum(Film) 1785, 1760, 1690 cm⁻¹ |
| 19 | Ph-CH(CONH-)(NHCOCHCH₃-cyclopropyl) | -COOCH₂CCl₃ | -CH₃ | -SCN | -S- | Oil<br>Infrared Absorption Spectrum(Film) 1780, 1765, 1680 cm⁻¹ |

-continued

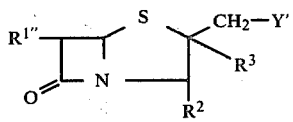

| No. | R[1"] | R[2] | R[3] | Y' | X | Property of the product |
|---|---|---|---|---|---|---|
| 20 | 2-Cl-phenyl-C(=N-O-)-C(CH₃)=...CONH— (isoxazole methyl) | —COOCH₂CCl₃ | —CH₃ | —SCN | —S— | Powder Infrared Absorption Spectrum(Nujol) 1785, 1770, 1670 cm⁻¹ |
| 21 | C₆H₅—CH₂CONH— | —COOCH₂CCl₃ | —CH₃ | —SCN | —S— | mp 137° to 140° C. |
| 22 | C₆H₅—CH₂CONH— | —COOH | —CH₃ | —SCOCH₃ | —S— | N,N'-dibenzylethylenediamine salt mp 105° to 107° C. |
| 23 | C₆H₅—CH₂CONH— | —COOH | —CH₃ | —S—CS—N(piperidine) | —S— | N,N'-dibenzylethylenediamine salt mp 100° C. (dec.) |
| 24 | C₆H₅—CH₂CONH— | —COOH | —CH₃ | —NH—C₆H₅ | —S— | mp 120° C. |
| 25 | 2-Cl-phenyl-C(=N-O-)-C(CH₃)=...CONH— | —COOH | —CH₃ | —S-(1-methyltetrazol-5-yl) | —S— | N,N'-dibenzylethylenediamine salt mp 117° to 119° C. (dec.) |
| 26 | (1H-tetrazol-1-yl)CH₂CONH— | —COOH | —CH₃ | —S-(1-methyltetrazol-5-yl) | —S— | mp 152° to 154° C. |
| 27 | C₆H₅—CH₂CONH— | —COOH | —CH₃ | —S-(1-methyltetrazol-5-yl) | —S— | N,N'-dibenzylethylenediamine salt mp 150° to 152° C. (dec.) |
| 28 | C₆H₅—CH₂CONH— | —COOH | —CH₃ | —S-(benzothiazol-2-yl) | —S— | Sodium salt mp 200° C. (dec.) |
| 29 | C₆H₅—CH₂CONH— | —COOH | —CH₃ | —S-(5-methyl-1,3,4-thiadiazol-2-yl) | —S— | Sodium salt mp 185° to 186° C. (dec.) |
| 30 | C₆H₅—CH₂CONH— | —COOCH₂CCl₃ | —CH₃ | —SCN | —S(=O)— | Colourless powder |
| 31 | C₆H₅—CH₂CONH— | —COOCH₂CCl₃ | —CH₃ | —Br | —S(=O)— | mp 114° to 115° C. (dec.) |

-continued

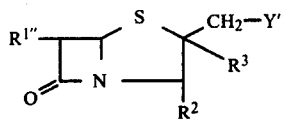

| No. | R¹″ | R² | R³ | Y′ | X | Property of the product |
|---|---|---|---|---|---|---|
| 32 | Ph—CH$_2$CONH— | —COOCH$_2$CCl$_3$ | —CH$_3$ | —Br | —S— α-oxide (S→O) | Amorphous |
| 33 | Ph—CH$_2$CONH— | —COOCH$_2$CCl$_3$ | —CH$_3$ | —Br | —S— | mp 90° to 93° C. |
| 34 | Ph—CH$_2$CONH— | —COOCH$_2$CCl$_3$ | —CH$_3$ | —Cl | —S— | mp 104° to 105° C. |
| 35 | Ph—CH$_2$CONH— | —COOH | —CH$_3$ | —Br | —S— | mp 164.5° to 165.5° C. |
| 36 | Ph—CH(NHCOOCH$_2$CCl$_3$)CONH— | —COOCH$_2$CCl$_3$ | —CH$_3$ | —Br | —S— | Powder |
| 37 | Ph—OCH$_2$CONH— | —COOCH$_3$ | —CH$_3$ | —Br | —S— | Oil; Infrared Absorption Spectrum 3350, 1785, 1748, 1690 cm$^{-1}$ |
| 38 | Ph—CH$_2$CONH— | —COOCH(CH$_3$)—cyclopropyl (—COOCH—CH$_3$ with CH<CH$_2$—CH$_2$) | —CH$_3$ | —Br | —S— | Oil |
| 39 | isoxazolyl-CH$_2$CONH— (N—N—CH$_2$CONH— / O-C(=O)—CH ring) | —COOCH$_2$CCl$_3$ | —CH$_3$ | —Br | —S— | Amorphous |
| 40 | Ph—CH$_2$CONH— | —COOCH$_2$—(3,5-di-t-butyl-4-hydroxyphenyl) | —CH$_3$ | —Br | —S— | White crystalline powder |
| 41 | HO—C$_6$H$_4$—CH(NHCOOCH(cyclopropyl))CONH— | —COOCH$_2$CCl$_3$ | —CH$_3$ | —Br | —S— | Powder |
| 42 | CH$_3$SCH$_2$CONH— | —COOCH$_2$CCl$_3$ | —CH$_3$ | —Br | —S→O | mp 71° to 73° C. (dec.) |
| 43 | (1,2,5-thiadiazol-3-yl)-CH$_2$CONH— | —COOCH$_2$CCl$_3$ | —CH$_3$ | —Br | —S→O | mp 115° to 116° C. (dec.) |
| 44 | Ph—CH$_2$CONH— | —COOCH$_2$CCl$_3$ | —CH$_3$ | Cl | —S→O | mp 130° to 131° C. |

Reaction of:

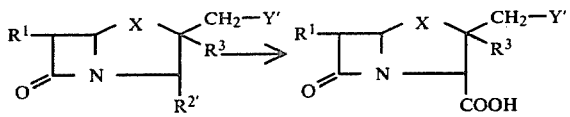

EXAMPLE 1

Acetic acid (1 ml) and zinc powder (0.75 g) were added to a solution of 2,2,2-trichloroethyl 2-acetylthiomethyl-2-methyl-6-(2-phenylacetamido) penam-3-carboxylate (0.65 g) in dimethylformamide (3 ml) under ice-cooling and the mixture was stirred for 2 hours at the same temperature. After the reaction, the reaction mixture was filtered and the filtrate was poured into 5% hydrochloric acid (20 ml) and then extracted with ethy acetate. The extract was washed with water, dried and the solvent was distilled off to give oil (0.365 g). After dissolving the oil in acetone (0.7 ml), to this solution was added a solution of N,N'-dibenzylethylenediamine diacetate (0.142 g) in water (5 ml) and precipitated powder was filtered. The powder was purified by reprecipitation method from a mixture of methanol and water to give N,N'-dibenzyl-ethylenediamine 2-acetylthiomethyl-2-methyl-6-(2-phenylacetamido)penam-3-carboxylate (0.211 g) mp. 105° to 107° C.

Analysis for $C_{18}H_{19}N_2O_5$ $S_2.\frac{1}{2}$ $C_{16}H_{22}N_2.H_2O$: Calc'd: C 57.19, H 5.87, N 7.69; Found: C 57.18, H 5.58, N 7.44

Infrared Absorption Spectrum (Nujol): 3300, 1772, 1690, 1670 cm$^{-1}$

EXAMPLE 2

Acetic acid (1 ml) and zinc powder (0.80 g) were added to a solution of 2,2,2-trichloroethyl 2-piperidinothiocarbonylthiomethyl-2-methyl-6-(2-phenylacetamido)penam-3-carboxylate (0.95 g) in dimethylformamide (5 ml) under ice-cooling and the mixture was stirred for 1 hour and 40 minutes. After the reaction, zinc powder was filtered off and the filtrate was poured into ethyl acetate. The solution was washed with 3% hydrochloric acid and then with water (four times) and dried over magnesium sulfate. After drying, the solvent was distilled off and the residue was dissolved in a small amount of methanol. To this solution was added an aqueous solution of N,N'-dibenzylethylenediamine diacetate and precipitates were collected by filtration, washed with water to give N,N'-dibenzylethylenediamine 2-piperidinothiocarbonylthiomethyl-2-methyl-6-(2-phenylacetamido)penam-3-carboxylate (0.30 g), mp. 100° C. (dec.).

Analysis for $C_{22}H_{26}O_4N_3S_3.\frac{1}{2}$ $C_{16}H_{22}$: Calc'd: C 57.03, H 6.22, N 8.87 Found: C 57.00, H 5.87, N 8.60

Infrared Absorption Spectrum (Nujol): 3280, 1777, 1660 cm$^{-1}$

EXAMPLE 3

2,2,2-Trichloroethyl 2-anilinomethyl-2-methyl-6-(2-phenylacetamido)penam-3-carboxylate (1.00 g) was dissolved in dimethylformamide (5 ml). To this solution were added acetic acid (0.5 ml) and then zinc powder under cooling at −15° C. and the mixture was stirred for 6 hours. After the reaction, zinc powder was filtered off and the filtrate was poured into ethyl acetate. The solution was washed 4 times with water and dried over magnesium sulfate. After drying, the solvent was distilled off and the residue was dissolved in a small amount of methanol and then pulverized by adding water to the solution. The powder was collected by filtration, washed with water and dried to give 2-anilinomethyl-2-methyl-6-(2-phenylacetamido)-penam-3-carboxylic acid (0.50 g), mp. 120° C.

Analysis for $C_{22}H_{23}O_4N_3S.\frac{1}{2}$ $H_2O$: Calc'd: C 60.81, H 5.56, N 9.67; Found: C 60.49, H 5.40, N 9.44

Infrared Absorption Spectrum (Nujol): 3400, 1780, 1745 cm$^{-1}$

EXAMPLE 4

2,2,2-Trichloroethyl 2-(1-methyl-1H-tetrazol-5-yl)thiomethyl-2-methyl-6-[3-(2-chlorophenyl)-5-methylisoxazole-4-carboxamido]penam-3-carboxylate (0.67 g) was dissolved in dimethylformamide (5 ml). To this solution were added acetic acid (0.8 ml) and zinc powder (0.7 g) under cooling at −15° C. and the mixture was stirred for 2 hours at the same temperature. After the reaction, zinc powder was filtered off and the filtrate was poured into 5% hydrochloric acid (20 ml) and then extraxted with ethyl acetate. The extract was washed with water, dried and the solvent was distilled off. The residue was dissolved in methanol (0.8 ml) and to this solution was added a solution of N,N'-dibenzylethylenediamine diacetate (0.18 g) in water (5 ml) and precipitates were collected by filtration, washed with water and dried to give N,N'-dibenzylethylenediamine 2-(1-methyl-1H-tetrazol-5-yl)thiomethyl-2-methyl-6-[3-(2-chlorophenyl)-5-methylisoxazole-4-carboxamido]penam-3-carboxylate (0.24 g), mp. 117° to 119° C. (dec.).

Infrared Absorption Spectrum (Nujol): 3400, 1778, 1665 cm$^{-1}$

EXAMPLE 5

2,2,2-Trichloroethyl 2-(1-methyl-1H-tetrazol-5-yl)thiomethyl-2-methyl-6-[2-(1H-tetrazol-1-yl)acetamido]-penam-3-carboxylate (0.6 g) was dissolved in dimethylformamide (5 ml). To this solution were added acetic acid (0.9 ml) and zinc powder (0.8 g) under cooling at −15° C. and the mixture was stirred for 1.5 hours at the same temperature. After the reaction, zinc powder was filtered off and the filtrate was poured into 5% hydrochloric acid (20 ml) and then extracted with ethyl acetate. The extract was washed with water, dried and the solvent was distilled off. The residue was crystallized from ether to give 2-(1-methyl-1H-tetrazol-5-yl)thiomethyl-2-methyl-6-[2-(1H-tetrazol-1-yl)acetamido]penam-3-carboxylic acid (0.25 g), mp. 152° to 154° C.

Infrared Absorption Spectrum (Nujol): 3230, 1780, 1738, 1692 cm$^{-1}$

EXAMPLE 6

2,2,2-Trichloroethyl 2-(1-methyl-1H-tetrazol-5-yl)thiomethyl-2-methyl-6-(2-phenylacetamido)penam-3-carboxylate (0.94 g) was dissolved in dimethylformamide (5 ml). To this solution were added under ice-cooling acetic acid (0.7 ml) and then zinc powder (0.80 g) under stirring and the mixture was stirred for 2.5 hours. After the reaction, zinc powder was filtered off and the filtrate was dissolved in ethyl acetate. The solution was washed with 3% hydrochloric acid, 3 times with water and dried over magnesium sulfate. After drying, the solvent was distilled off and the residue dissolved in a small amount of methanol and then crystallized by adding an aqueous solution of N,N'-dibenzylethylenediamine diacetate (0.36 g). Crystals were collected by filtration and washed with a mixture of ethanol and water and then dried to give N,N'-dibenzylethylenediamine 2-(1-methyl-1H-tetrazol-5-yl) thiomethyl-2-methyl-6-(2-phenylacetamido)penam-3-carboxylate (0.50 g), mp. 150° to 152° C. (dec.).

Analysis for $C_{18}H_{18}O_4N_6S_2 \cdot \frac{1}{2} \ C_{16}H_{22}N_2 \cdot \frac{1}{2} \ H_2O$: Calc'd: C 54.48, H 5.28, N 17.17; Found: C 54.45, H 5.29, N 17.00

Infrared Absorption Spectrum (Nujol): 3370, 1763, 1674 cm$^{-1}$

EXAMPLE 7

2,2,2-Trichloroethyl 2-chloromethyl-2-methyl-6-(2-phenylacetamido)penam-3-carboxylate (1.5 g) was dissolved in dried dimethylformamide (8 ml) and to this solution were added formic acid (1.5 ml) and then zinc powder (1.5 g) under stirring while ice-cooling. After stirring for 2 hours at the same temperature, zinc powder was filtered off and washed with dimethylformamide (5 ml). The filtrate and the washings were added to a mixed cool solution of ethylacetate (30 ml) and 5% hydrochloric acid (15 ml). After extracting with ethyl acetate, the extract was washed with water and dried over magnesium sulfate. The gummy substance (1.16 g) obtained by distilling off the solvent under reduced pressure was crystallized from a mixed solvent of ethyl acetate and isopropyl ether to give 2-chloromethyl-2-methyl-6-(2-phenylacetamido)penam-3-carboxylic acid (660 mg) mp. 110° to 112° C. (dec.).

Analysis for $C_{16}H_{17}N_2O_4SCl$: Calc'd: 52.10, H 4.65, N 7.60, S 8.69, Cl 9.61; Found: C 51.90, H 4.73, N 7.46, S 8.67, Cl 9.84

Infrared Absorption Spectrum (Nujol): 3325, 1788, 1730, 1635 cm$^{-1}$

EXAMPLE 8

2,2,2-Trichloroethyl 2-(benzothiazol-2-yl)thiomethyl-2-methyl-6-(2-phenylacetamido)penam-3-carboxylate (0.90 g) was dissolved in dimethylformamide (5 ml). To this solution were added acetic acid (0.7 ml) under ice-cooling and then zinc powder (0.80 g) under stirring, and then the mixture was stirred for 2 hours. After zinc powder was filtered off, the filtrate was dissolved in ethyl acetate and the solution was washed with 3% hydrochloric acid and then 3 times with water and thereafter dried over magnesium sulfate. The residue obtained by distilling off the solvent was dissolved in a small amount of acetone. To this solution was added a solution of sodium 2-ethylhexanoate (250 mg) in acetone (5 ml) and the solution was again concentrated. The residue was crystallized by adding ethanol and the crystals were collected by filtration, washed with a small amount of ethanol and dried to give sodium 2-(benzothizol-2-yl)thiomethyl-2-methyl-6-(2-phenylacetamido)penam-3-carboxylate (0.50 g), mp. 200° C. (dec.).

Infrared Absorption Spectrum (Nujol): 3400, 1760, 1670, 1600 cm$^{-1}$

EXAMPLE 9

2,2,2-trichloroethyl 2-(5-methyl-1,3,4-thiadiazol-2-yl)thiomethyl-2-methyl-6-(2-phenylacetamido)-penam-3-carboxylate (0.80 g) was dissolved in dimethylformamide (5 ml). To this solution were added acetic acid (0.5 ml) and then zinc powder (0.80 g) under ice-cooling and the mixture was stirred for 2 hours. Zinc powder was filtered off and the filtrate was dissolved in ethyl acetate. The solution was washed with 5% hydrochloric acid and then 4 times with water and thereafter dried over magnesium sulfate. The residue obtained by distilling off the solvent was dissolved in a small amount of ethyl acetate and to the solution was added a solution of sodium 2-ethylhexanoate (250 mg) in acetone (5 ml), and then the solution was concentrated. The residue was pulverized from ethyl acetate and further the powder was crystallized from ethanol. The crystals were collected by filtration, washed with ethanol and dried to give sodium 2-(5-methyl-1,3,4-thiadiazol-2-yl)thiomethyl-2-methyl-6-(2-phenylacetamido)penam-3-carboxylate (0.28 g), mp. 185° to 186° C. (dec.).

Infrared Absorption Spectrum (Nujol): 3200, 1757, 1670, 1625 cm$^{-1}$

In the similar manner, the following compound was obtained. (1) 2-Bromomethyl-2-methyl-6-(2-phenoxyacetamido)penam-3-carboxylic acid (mp. 164.5° to 165.5° C.).

Reaction of:

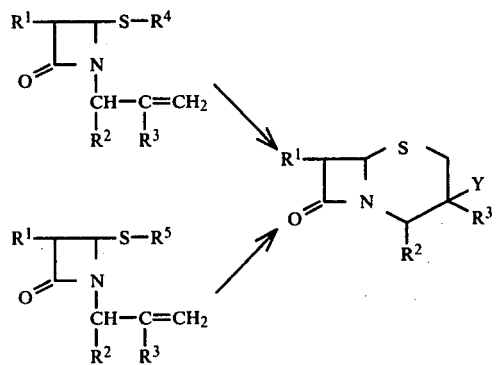

EXAMPLE 1

Methyl 2-oxo-3-(2-phenoxyacetamido)-4-(benzothiazol-2-yl)-dithio-α-isopropenyl-1-azetidineacetate (454 mg) was dissolved in methylene chloride (20 ml). To this solution was added methanol (5 ml) and thereafter added boron trifluoride etherate (0.124 g) at 0° C. The mixture was stirred for 3 hours at the same temperature and further stirred for 2 hours at 5° to 10° C. After the reaction, the mixture was washed with 5% sodium bicarbonate aqueous solution and with water. After drying the mixture, the mixture was concentrated and the oily residue (250 mg) was purified by column chromatography on silica gel to give oily methyl 3-methyl-3-methoxy-7-(2-phenoxyacetamido)-cepham-4-carboxylate.

Infrared Absorption Spectrum (CHCl$_3$): 3400, 1772, 1739, 1688 cm$^{-1}$

EXAMPLE 2

Methyl 2-oxo-3-(2-phenoxyacetamido)-4-(benzothiazol-2-yl)dithio-α-isopropenyl-1-azetidineacetate (1.06 g) was dissolved in methylene chloride (20 ml). To this solution were added aniline (0.28 g) and then silver fluoroborate (0.80 g) and thereafter the mixture was stirred for 2 days at room temperature. After the reaction, the reaction mixture was filtered and the filtrate was washed with a dilute phosphoric acid aqueous solution andd then with water. After drying the mixture, the mixture was concentrated and the residue was purified by column chromatography on silica gel (25 g) to give methyl 3-methyl-3-anilino-7-(2-phenoxyacetamido)-cepham-4-carboxylate (0.38 g), mp. 129° to 130° C.

EXAMPLE 3

2,2,2-Trichloroethyl 2-oxo-3-(2-phenylacetamido)-4-(benzothiazol-2-yl)dithio-α-isopropenyl-1-azetidineacetate (1.26 g) was dissolved in ethyl acetate (15 ml). To this solution was added acetic acid (5 ml) and then silver acetate (0.68 g) under stirring at room temperature. The mixture was stirred for 4 hours at the same temperature. After the reaction, the reaction mixture was filtered and the filtrate was washed with water and then with 5% sodium bicarbonate aqueous solution. The solution was filtered again and the filtrate was washed with water and then dried. The solvent was distilled off and the residue was purified by thin layer chromatography using a mixture of acetone: benzene (1:9) to give amorphous 2,2,2-trichloroethyl 3-acetoxy-3-methyl-7-(2-phenylacetamido)cepham-4-carboxylate.

Infrared Absorption Spectrum (CHCl$_3$): 3425, 1780, 1750, 1680 cm$^{-1}$

EXAMPLE 4

Methyl 2-oxo-3-(2-phenoxyacetamido)-4-benzothiazol-2-yl)dithio-α-isopropenyl-1-azetidineacetate (2.12 g) was dissolved in methanol (80 ml). To this solution was added silver nitrate (0.68 g) and the mixture was refluxed for 28 hours. After the reaction, precipitates were filtered and the filtrate was concentrated. The obtained residue was extracted with ethyl acetate and the extract was washed with water and then dried. The solvent was distilled off and the obtained residue was purified by column chromatography on silica gel using chloroform as developing solvent to give pale yellow oil of methyl 3-methoxy-3-methyl-7-(2-phenoxyacetamido)cepham-4-carboxylate (620 mg.).

Infrared Absorption Spectrum (CHCl$_3$): 3400, 1772, 1739, 1688 cm$^{-1}$

Similar result was obtained using methylene chloride as solvent and silver fluoroborate instead of silver nitrate.

EXAMPLE 5

Methyl 2-oxo-3-(2-phenoxyacetamido)-4-(benzothiazol-2-yl)dithio-α-isopropenyl-1-azetidineacetate (0.53 g) was dissolved in methanol (20 ml). To this solution was added silver acetate (0.17 g) and the mixture was refluxed for 39 hours. After the reaction, the reaction mixture was post-treated in the similar manner as described in Example 1 to give oily methyl 3-methyl-3-methoxy-7-(2-phenoxyacetamido)-cepham-4-carboxylate (200 mg).

EXAMPLE 6

A mixture of methyl 2-oxo-3-(2-phenoxyacetamido)-4-(benzothiazol-2-yl)-dithio-α-isopropenyl-1-azetidineacetate (0.53 g), mercuric acetate (0.3 g) and methanol (20 ml) were refluxed for 48 hours. After the reaction, the reaction mixture was post-treated in the similar manner as described in Example 1 to give oily methyl 3-methyl-3-methoxy-7-(2-phenoxyacetamido)cepham-4-carboxylate (180 mg).

EXAMPLE 7

Methyl 2-oxo-3-(2-phenoxyacetamido)-4-(benzothiazol-2-yl)dithio-α-isopropenyl-1-azetidineacetate (0.53 g) was dissolved in methanol (20 ml). To this solution was added mercuric chloride (0.27 g) and the mixture was refluxed for 24 hours. After the reaction, the reaction mixture was post-treated in the similar manner as described in Example 1 to give oily methyl 3-methyl-3-methoxy-7-(2-phenoxyacetamido)cepham-4-carboxylate (220 mg).

EXAMPLE 8

Methyl 2-oxo-3-(2-phenoxyacetamido)-4-(benzothiazol-2-yl)-dithio-α-isopropenyl-1-azetidineacetate (0.53 g) was dissolved in methanol (20 ml). To this solution was added cupric oxide (0.15 g), and the mixture was refluxed for 72 hours. After the reaction, the reaction mixture was post-treated in the similar manner as described in Example 1 to give oily methyl 3-methyl-3-methoxy-7-(2-phenoxyacetamido)cepham-4-carboxylate (50 mg).

EXAMPLE 9

2,2,2-Trichloroethyl 2-oxo-3-(2-phenylacetamido)-4-(benzothiazol-2-yl)dithio-α-isopropenyl-1-azetidineacetate (0.63 g) and p-toluenesulfonic acid monohydrate (0.19 g) were dissolved in a mixture of methanol (15 ml) and methylene chloride (5 ml). The mixture was stirred for 4.5 hours at 50° C. After the reaction, methanol and methylene chloride were distilled off and the residue was dissolved in ethyl acetate (10 ml). To ethyl acetate layer was washed with a saturated sodium bicarbonate aqueous solution and then with water and thereafter dried over magnesium sulfate. The residue obtained by removing the solvent was purified by column chromatography on silica gel using chloroform as developing solvent to give 2,2,2-trichloroethyl 3-methyl-3-methoxy-7-(2-phenylacetamido)-cepham-4-carboxylate (120 mg), mp. 132° to 133° C.

The following compounds were obtained by using the same procedures as those of the Examples 1 to 9.

(1) 2,2,2-Trichloroethyl 3-methyl-3-azido-7-(2-phenylacetamido)cepham-4-carboxylate (mp. 136° to 140° C.).

(2) 2,2,2-Trichloroethyl 3-methyl-3-hydroxy-7-(2-phenylacetamido)cepham-4-carboxylate (mp. 169° to 171° C.).

(3) 2,2,2-Trichloroethyl 3-methyl-3-isopropoxy-7-(2-phenylacetamido)cepham-4-carboxylate (oil).

(4) 1-Cyclopropylethyl 3-methyl-3-anilino-7-(2-phenylacetamido)cepham-4-carboxylate (colorless oil).

(5) 2,2,2-Trichloroethyl 3-methyl-3-anilino-7-(2-phenylacetamido)cepham-4-carboxylate (oil).

(6) 3-anilino-3-methyl-7-(2-phenoxyacetamido)cepham-4-carboxylic acid (mp. 119° to 123° C. (dec).

Reaction of:

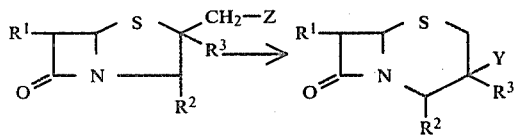

EXAMPLE 1

A mixture of 2,2,2-trichloroethyl 2-bromomethyl-2-methyl-6-(2-phenylacetamido)penam-3-carboxylate (1.08 g), sodium azide (0.26 g), acetone (20 ml) and water (4 ml) was stirred for 4 hours at room temperature. After acetone was distilled off under reduced pressure, the residue was extracted with ethyl acetate. The ethyl acetate layer was washed with water, with saturated sodium bicarbonate aqueous solution and further with water and then dried over magnesium sulfate. The solvent was distilled off under reduced pressure and a small quantity of ether was added to the residue to give colorless crystals of 2,2,2-trichloroethyl 3-azido-3-methyl-7-(2-phenylacetamido)cepham-4-carboxylate (170 mg). This substance was recrystallized from carbon tetrachloride to give crystals melting at 136° to 140° C.

Infrared Absorption Spectrum (Nujol): 3310, 2110, 1770, 1746, 1658 cm$^{-1}$

EXAMPLE 2

2,2,2-Trichloroethyl 2-bromomethyl-2-methyl-6-(2-phenylacetamido)penam-3-carboxylate (0.54 g) was dissolved in absolute dimethylsulfoxide (5 ml). To this solution was added silver fluoroborate (0.20 g) and then the mixture was stirred under shielding from light for 3 hours at room temperature. To the solution was added a solution of triethylamine (0.1 g) in dimethylsulfoxide (0.5 ml) and the solution was further stirred for 5 hours and then allowed to stand overnight at room temperature. Precipitates were filtered off and the filtrate was poured into ice-water and then extracted with ethyl acetate. The extract was washed with water and dried. The residue obtained by distilling off the solvent under reduced pressure was crystallized by a small amount of ether to give colorless crystals of 2,2,2-trichloroethyl 3-hydroxy-3-methyl-7-(2-phenylacetamido)cepham-4-carboxylate (280 mg) (58%). This substance was recrystallized from a mixed solvent of benzene-n-hexane to give colorless needles melting at 169° to 171° C.

Analysis for $C_{18}H_{19}N_2O_5SCl_3$: Calc'd: C 44.87, H 3.97, N 5.81, S 6.66, Cl 22.08; Found: C 45.08, H 3.93, N 5.75, S 6.45, Cl 21.96

EXAMPLE 3

2,2,2-Trichloroethyl 2-bromomethyl-2-methyl-6-(2-phenylacetamido)penam-3-carboxylate (0.55 g) was dissolved in a mixture of tetrahydrofuran (5 ml) and methanol (5 ml). To this solution was added silver fluoroborate (0.24 g) under cooling and then the mixture was stirred for 1 hour. The reaction mixture was concentrated and the obtained residue was dissolved in chloroform. This solution was washed with a saturated sodium bicarbonate aqueous solution and with water and dried over magnesium sulfate. The residue obtained by distilling off the solvent was subjected to chromatography on silica gel using chloroform as developing solvent. The obtained crystals were recrystallized from carbon tetrachloride to give 2,2,2-trichloroethyl 3-methyl-3-methoxy-7-(2-phenylacetamido)-cepham-4-carboxylate (0.27 g), mp. 132° to 133° C.

The similar result was obtained using methylene chloride instead of tetrahydrofuran in the above example.

Infrared Absorption Spectrum (Nujol): 3300, 1780, 1760, 1683 cm$^{-1}$

EXAMPLE 4

2,2,2-Trichloroethyl 2-bromomethyl-2-methyl-6-(2-phenylacetamido)penam-3-carboxylate (0.55 g) was dissolved in a mixture of tetrahydrofuran (5 ml) and isopropanol (5 ml). To this solution was added silver fluoroborate (0.24 g) under ice-cooling and the mixture was stirred for 1 hour. The reaction mixture was concentrated and the obtained residue was dissolved in chloroform. This solution was washed with a saturated sodium bicarbonate aqueous solution and with water and then dried over magnesium sulfate. The residue obtained by distilling off the solvent was purified by chromatography on silica gel using chloroform as developing solvent to give oily 2,2,2-trichloroethyl 3-methyl-3-isopropoxy-7-(2-phenylacetamido)-cepham-4-carboxylate (0.10 g).

Infrared Absorption Spectrum (Film): 3300, 1760, 1750, 1670 cm$^{-1}$

EXAMPLE 5

Methyl 2-bromomethyl-2-methyl-6-(2-phenoxyacetamido)penam-3-carboxylate (0.88 g) was dissolved in methylene chloride (13 ml) containing methanol. To the solution was added silver fluoroborate (0.45 g), and the mixture was stirred for 2 hours. After the reaction, the reaction mixture was filtered and the filtrate was washed with a dilute sodium bicarbonate aqueous solution and then with water. The solution was dried over magnesium sulfate and concentrated. The residue was subjected to column chromatography on silica gel (25 g) and eluted with chloroform. The elute was separated into fractions of each about 20 ml and the seventh to tenth fractions were collected. The solvent was distilled off to give Methyl 3-methoxy-3-methyl-7-(2-phenoxyacetamido)cepham-4-carboxylate (0.60 g).

Infrared Absorption Spectrum (CHCl$_3$): 3400, 1772, 1739, 1688 cm$^{-1}$

The following compounds were obtained by using the same procedures as those of the Examples 1 to 5.

(1) Methyl 3-anilino-3-methyl-7-(2-phenoxyacetamido)-cepham-4-carboxylate (mp. 129° to 130° C.).

(2) 1-Cyclopropylethyl 3-anilino-3-methyl-7-(2-phenoxyacetamido)cepham-4-carboxylate (colorless oil).

(3) 2,2,2-Trichloroethyl 3-anilino-3-methyl-7-(2-phenoxyacetamido)cepham-4-carboxylate (oil).

(4) 3-anilino-3-methyl-7-(2-phenoxyacetamido)-cepham-4-carboxylic acid.

Reaction of:

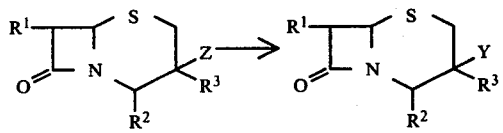

EXAMPLE 1

Aniline (0.28 g) was added to a solution of 2,2,2-trichloroethyl 3-bromo-3-methyl-7-(2-phenylacetamido)-cepham-4-carboxylate (1.10 g) in methylene chloride (15 ml). To the solution was added silver fluoroborate 0.45 g under ice-cooling under stirring and stirred at the same temperature for 4 hours. After the reaction, the mixture was filtered and the filtrate was washed with dilute phosphoric acid aqueous solution and water in turn. The solution was dried over magnesium sulphate and concentrated. The residue was subjected to column chromatography on silica gel (25 g) using chloroform. The 12th to 13th fractions of fractions, each of which was separated into 20 cc, were concentrated to give oily 2,2,2-trichlocoethyl 3-anilino-3-methyl-7-(2-phenylacetamido) cepham-4-carboxylate.

Infrared Absorption Spectrum (CHCl$_3$): 3420, 1772, 1750, 1680 cm$^{-1}$

The following compounds were obtained by using the same procedure as that of the Example 1.

| No. | R¹ | R² | R³ | Y | Property of the product |
|---|---|---|---|---|---|
| 1 | C₆H₅—CH₂CONH— | —COOCH₂CCl₃ | —CH₃ | —N₃ | mp. 136°–140° C. |
| 2 | C₆H₅—CH₂CONH— | —COOCH₂CCl₃ | —CH₃ | —OH | mp. 169°–171° C. |
| 3 | C₆H₅—CH₂CONH— | —COOCH₂CCl₃ | —CH₃ | —OCH₃ | mp. 132°–133° C. |
| 4 | C₆H₅—CH₂CONH— | —COOCH₂CCl₃ | —CH₃ | —OCH(CH₃)₂ (—OCH(CH₃)CH₃) | oily |
| 5 | C₆H₅—CH₂CONH— | —COOCH₃ | —CH₃ | —OCH₃ | oily |
| 6 | C₆H₅—CH₂CONH | —COOCH₃ | —CH₃ | —NH—C₆H₅ | mp. 129°–130° C. |
| 7 | C₆H₅—CH₂CONH | —COOCH(CH)(CH₂—CH₂) (cyclopropyl) | —CH₃ | —NH—C₆H₅ | colorless oily |
| 8 | C₆H₅—OCH₂CONH— | —COOH | —CH₃ | —NH—C₆H₅ | mp. 119°–123° C. (dec) |

Reaction of:

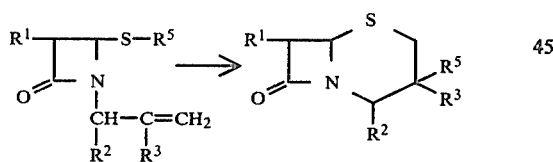

EXAMPLE 1

1-cyclopropylethyl 2-oxo-3-(2-phenoxyacetamido)-4-anilinothio-α-isopropenyl-1-azetidineacetate (0.4 g) was dissolved in dried methylene chloride (10 ml). To this solution was added dropwise a solution of boron trifluoride etherate (50 mg) in dried methylene chloride (3 ml) at 0° C. and the mixture was stirred for 5 hours at the same temperature. After the reaction, the reaction mixture was washed with 5% sodium bicarbonate aqueous solution and several times with water and then dried. The oil obtained by distilling off the solvent was purified by column chromatography on silica gel using chloroform as developing solvent to give colorless oil of 1-cyclopropylethyl 3-anilino-3-methyl-7-(2-phenoxyacetamido)cepham-4-carboxylate (198 mg.).

Infrared Absorption Spectrum (Film): 3300, 1777, 1740, 1690 cm⁻¹

EXAMPLE 2

Methyl 2-oxo-3-(2-phenoxyacetamido)-4-anilinothio-α-isopropenyl-1-azetidineacetate (170 mg) was disolved in dried methylene chloride (4 ml). To this solution was added dropwise a solution of boron trifluoride etherate (25 mg) in dried methylene chloride (2 ml) under ice-cooling and the mixture was stirred for 1 hour at the same temperature. After reaction, the reaction mixture was washed with 5% sodium bicarbonate aqueous solution and with water and then dried. The oil obtained by distilling off the solvent was subjected to column chromatography on silica gel using chloroform as developing solvent to give methyl 3-anilino-3-methyl-7-(2-phenoxyacetamido)-cepham-4-carboxylate (80 mg), mp 129° to 130° C., from the fifth to eighth fractions of fractions each of which was separated into 50 ml.

Infrared Absorption Spectrum (CHCl₃): 3420, 1775, 1736, 1691 cm⁻¹

In the similar manner, the following compound was obtained.

(1) 3-anilino-3-methyl-7-(2-phenoxyacetamido)cepham-4-carboxylic acid (mp 119° to 123° C. (dec))

Reaction of:

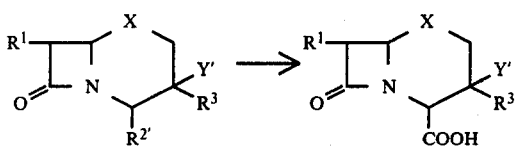

EXAMPLE 1

1-Cyclopropylethyl 3-anilino-3-methyl-7-(2-phenoxyacetamido)cepham-4-carboxylate (142 mg) was dissolved in ice-cooled trifluoroacetic acid (1.5 ml) and the mixture was stirred for 1 hour under ice-cooling. After the reaction, the reaction mixture was concentrated under reduced pressure. The residue was dissolved by adding ethyl acetate and extracted with 5% sodium bicarbonate aqueous solution. The extract was adjusted to pH2 with 5% hydrochloric acid and back-extracted with ethyl acetate. The extract was washed with water, dried and the solvent was distilled off. The residue (amorphous) was dissolved in methanol and to this solution was added water little by little. Precifitates were collected by filtration and dried to give powder of 3-anilino-3-methyl-7-(2-phenoxy-acetamido)cepham-4-carboxylic acid (62 mg), mp 119° to 123° C. (dec.).

Analysis for $C_{22}H_{23}O_5N_3S$. 3/2 $H_2O$: Calc'd C 56.40, H 4.95, N 8.97; Found C 56.57, H 5.05, N 8.97

IP spectrum (Nujol): 3300, 1770, 1735, 1665 cm$^{-1}$

In the similar manner, the following compound was obtained.

(1) 3-bromo-3-methyl-7-(2-phenoxy-acetamido)cepham-4-carboxylic acid (amorphous).

Reaction of:

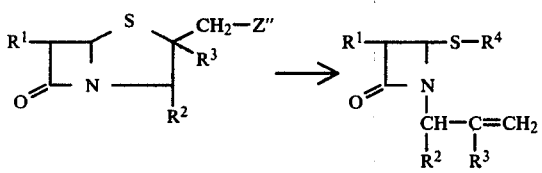

EXAMPLE 1

5-Methyl-1,3,4-thiodiazole-2-thiol (0.16 g) was dissolved in a mixture of pH 6.5 phosphate buffer (5 ml) and acetone (10 ml). To the solution was added 2,2,2-trichloroethyl 2L-bromomethyl-2-methyl-6-(2-phenylacetamido)penam-3-carboxylate (0.54 g) and the mixture was stirred for 3 hours at room temperature. The reaction mixture was extracted with ethyl acetate and the ethyl acetate layer was washed with sodium bicarbonate aqueous solution and with water and then dried over magnesium sulfate. The solvent was distilled off from the extract and the residue was purified by column chromatography on silica gel using chloroform as developing solvent to give 2,2,2-trichloroethyl 2-oxo-3-(2-phenylacetamido)-4-(5-methyl-1,3,4-thiadiazol-2-yl)dithio-α-propenyl-1-azetidineacetate (0.24 g), mp 108° to 109° C., from the fifth to ninth fractions of fractions each of which was separated into 30 ml.

Infrared Absorption Spectrum (Nujol): 3280, 1788, 1760, 1654 cm$^{-1}$

EXAMPLE 2

2-Mercaptobenzothiazole (0.20 g) was dissolved in a mixture of pH 6.7 phosphate buffer (15 ml) and dioxane (15 ml). To the solution was added 2,2,2-trichloroethyl 2-bromomethyl-2-methyl-6-(2-phenylacetamido)penam-3-carboxylate (0.54 g) and the mixture was stirred for 7 hours at room temperature. Dioxane was distilled off from the mixture and the residue was extracted with ethyl acetate. The ethyl acetate layer was washed with 2% potassium carbonate aqueous solution and with water and then dried over magnesium sulfate. The residue obtained by distilling off the solvent was purified by column chromatography on silica gel using chloroform as developing solvent to give 2,2,2-trichloroethyl 2-oxo-3-(2-phenylacetamido)-4-(benzethiazol-2-yl)dithio-α-propenyl-1-azetidineacetate (0.10 g), mp 140° to 141° C., from the fourth to sixth fractions of fractions each of which was separated into 30 ml.

EXAMPLE 3

5-Methyl-1,3,4-thiadiazole-2-thiol (0.4 g) was dissolved in a mixture of pH 7.3 phosphate buffer (20 ml) and acetone (20 ml). To the solution was added a solution of methyl 2-bromomethyl 2-methyl-6-(2-phenoxyacetamido)penam-3-carboxylate (0.80 g) in acetone (10 ml) and the mixture was stirred for 4 hours at room temperature. After the reaction was completed, acetone was distilled off from the reaction mixture and the residue was extracted with ethyl acetate. The extract was washed with sodium bicarbonate aqueous solution and with water, dried over magnesium sulfate and then the solvent was distilled off. The residue was subjected to column chromatography on silica gel (60 g) and eluted with chloroform. The eluate was separated into about 30 ml fraction to give oily methyl 2-oxo-3-(2-phenoxyacetamido)-4-(5-methyl-1,3,4-thiadiazol-2-yl)dithio-α-propenyl-1-azetidineacetate (0.22 g) from the eleventh to thirteenth fractions.

Infrared Absorption Spectrum (Chloroform): 3430, 1779, 1742, 1692 cm$^{-1}$

Further, oily 4,4-dithiobis[methyl-2-oxo-3-(2-phenoxyacetamido)-α-propenyl-1-azetidineacetate] (0.30 g) was obtained from the eighth to tenth fractions of the above fractions.

Infrared Absorption Spectrum (Film): 3280, 1770, 1740, 1680 cm$^{-1}$

The following compounds were obtained by using the same procedures as those of the Examples 1 to 3.

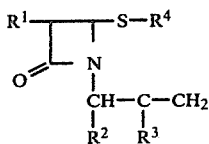

| No. | R¹ | R² | R³ | R⁴ | Property of the product |
|---|---|---|---|---|---|
| 1 | C₆H₅—OCH₂CONH— | —COOH | —CH₃ | -S-[5-methyl-1,3,4-thiadiazol-2-yl] | mp 142° to 144° C. |
| 2 | C₆H₅—CH₂CONH— | —COOCH₂CCl₃ | " | " | mp 108° to 109° C. |
| 3 | C₆H₅—OCH₂CONH— | —COOCH₃ | " | -S-[benzothiazol-2-yl] | mp 146° to 147° C. |
| 4 | " | —COOH | " | " | mp 146° to 148° C. (dec.) |
| 5 | " | —COOCH₂CCl₃ | " | " | mp 171° to 174.5° C. |
| 6 | C₆H₅—CH(NHCOOCH₂CCl₃)CONH— | —COOCH₂CCl₃ | " | " | mp 159° to 161° C. |
| 7 | C₆H₅—OCH₂CONH— | —COON=C(CH₃)₂ | " | " | Oil |
| 8 | C₆H₅—CH₂CONH— | —COOH | " | " | mp 76° to 80° C. |
| 9 | " | —COOCH(CH₃)—CH(cyclopropyl) | " | " | mp 114° to 117° C. |
| 10 | C₆H₅—CH(NHCOOC(CH₃)₃)CONH— | —COOCH₂CCl₃ | " | " | Amorphous |
| 11 | C₂H₅OCOCH=C(CH₃)—NH— | " | " | " | Oil |
| 12 | [4,5-dihydro-1,3-dioxa-2-N,N-pyrazolidinyl]—CH₂CONH— | " | " | " | Amorphous |
| 13 | [thien-2-yl]—CH₂CONH— | " | " | " | mp 136° to 137° C. |
| 14 | C₆H₅—CH(NHCOOCH(CH₃)—CH(cyclopropyl))CONH— | " | " | " | mp 164° to 165° C. |
| 15 | NOCH₂CONH— | " | " | " | mp 117° to 119° C. |
| 16 | C₆H₅—CH₂CONH— | —COOCH₂—[3,5-di-t-C₄H₉-4-OH-phenyl] | " | " | mp 149° to 152° C. |

-continued

| No. | R¹ | R² | R³ | R⁴ | Property of the product |
|---|---|---|---|---|---|
| 17 | HO—⌬—CH(NH—COOCH(CH₃)—CH<CH₂/CH₂)CONH— | —COOCH₂CCl₃ | " | " | mp 175° to 176° C. |
| 18 | ⌬—OCH₂CONH— | —COOCH(CH₃)—CH<CH₂/CH₂ | " | " | mp 127° to 129° C. |
| 19 | " | —COOCH₃ | " | —S—CH₂—⌬ | Oil |
| 20 | " | " | " | —S—COCH₃ | Oil |
| 21 | " | " | " | —S—⌬ | Oil |
| 22 | " | " | " |  | Oil |
| 23 | " | " | " |  | Oil |
| 24 | ⌬—CH₂CONH— | —COOCH₂CCl₃ | " |  | Oil |

What is claimed is:

1. A compound of the general formula:

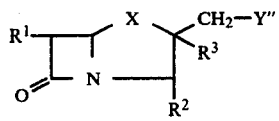

wherein R¹ is a conventional, pharmaceutically acceptable acylamino, R² is carboxy or a conventionally protected carboxy, X is —S— or $$-\overset{O}{\underset{\|}{S}}-,$$

R³ is lower alkyl and Y″ is azido.

2. The compound according to claim 1, in which R¹ is phenyl (lower) alkanoylamino, phenoxy(lower)alkanoylamino, N-lower alkyoxycarbonylphenylglycylamino or 3-halophenyl-5-(lower)alkylisoxazol-4-ylcarboxamido, R² is carboxy, lower alkoxycarbonyl, trihalo(lower)alkoxycarbonyl or carboxy salt, R³ is lower alkyl, X is —S— or $$-\overset{O}{\underset{\|}{S}}-$$

and Y″ is azido.

3. The compound according to claim 2, in which R¹ is phenylacetamido, phenoxyacetamido, N-(1-cyclopropylethoxy)carbonylphenylglycylamino or 3-(2-chlorophenyl)-5-methylisoxazol-4-ylcarboxamido, R² is carboxy, methoxycarbonyl, 2,2,2-trichloroethoxycarbonyl or a carboxy salt with N,N'-dibenzylethylenediamine, R³ is a methyl, X is —S— or $$-\overset{O}{\underset{\|}{S}}-$$

and Y″ is azido.

4. The compound according to claim 3, which is 2,2,2-trichloroethyl 2-azidomethyl-2-methyl-6-(2-phenylacetamido)-penam-3-carboxylate.

* * * * *